(12) United States Patent
Rappuoli et al.

(10) Patent No.: US 8,039,007 B2
(45) Date of Patent: Oct. 18, 2011

(54) **POLYPEPTIDES FROM *NEISSERIA MENINGITIDIS***

(75) Inventors: Rino Rappuoli, Castelnuovo Berardenga (IT); Claire Fraser, Clarksville, MD (US); Mariagrazia Pizza, Siena (IT); Maria Scarselli, Siena (IT); Davide Serruto, Siena (IT); Hervé Tettelin, Ellicott City, MD (US)

(73) Assignees: J. Craig Venter Institute, Inc., Rockville, MD (US); Novartis AG, Basel (CH)

( * ) Notice: Subject to any disclaimer, the term of this patent is extended or adjusted under 35 U.S.C. 154(b) by 0 days.

(21) Appl. No.: 12/306,920

(22) PCT Filed: Jun. 29, 2007

(86) PCT No.: PCT/IB2007/002838
§ 371 (c)(1),
(2), (4) Date: Sep. 21, 2009

(87) PCT Pub. No.: WO2008/001224
PCT Pub. Date: Jan. 3, 2008

(65) Prior Publication Data
US 2010/0015151 A1    Jan. 21, 2010

Related U.S. Application Data

(60) Provisional application No. 60/817,950, filed on Jun. 29, 2006.

(51) Int. Cl.
*A61K 39/095* (2006.01)
*C07H 21/04* (2006.01)
*C07K 14/22* (2006.01)

(52) U.S. Cl. ............ 424/250.1; 424/184.1; 530/350; 536/23.7

(58) Field of Classification Search .............. None
See application file for complete search history.

(56) References Cited

U.S. PATENT DOCUMENTS 7,504,111 B2 *   3/2009   Fontana et al. ............ 424/249.1
2002/0082206 A1 *   6/2002   Leach et al. ................ 514/12

FOREIGN PATENT DOCUMENTS

WO    WO0279243 A2 *   10/2002

OTHER PUBLICATIONS

Houghten et al. (Vaccines, 1986, Edited by Fred Brown: Cold Spring Harbor Laboratory).*
Holmes, Exp. Opin.Invest. Drugs, 2001, 10(3):511-519).*
Greenspan et al (Nature Biotechnology, 1999, 7:936-937).*
Database Geneseq [Online]. "Protein encoded by Prokaryotic essential gene #23450." XP002467933, retrieved from EBI accession No. GSP:ABU37923, from patent application WO200277, 2007.
Database Geneseq [Online]. "Prokaryotic essential gene #23450." XP002467934, retrieved from EBI accession No. GSN:ACA41793, from patent application WO200277183, 2007.
Pizza, M. et al. "Identification of vaccine candidates against serogroup B meningococcus by whole-genome sequencing." Science, 287(5459): 1816-1820 (2000).
Tettelin, H. et al. "Complete genome sequence of *Neisseria meningitidis* serogroup B strain MC58." Science, 287(5459): 1809-1815 (2000).
Parkhill, J. et al. "Complete DNA sequence of a serogroup A strain of *Neisseria meningitidis* Z2491." Nature, 404(6777): 502-506 (2000).

* cited by examiner

*Primary Examiner* — Gary Nickol
*Assistant Examiner* — Padma Baskar
(74) *Attorney, Agent, or Firm* — Morrison & Foerster LLP

(57) ABSTRACT

Various specific meningococcal proteins are disclosed. The invention provides related polypeptides, nucleic acids, antibodies and methods. These can all be used in medicine for treating or preventing disease and/or infection caused by meningococcus, such as bacterial meningitis.

6 Claims, No Drawings

POLYPEPTIDES FROM *NEISSERIA MENINGITIDIS*

All documents cited herein are incorporated by reference in their entirety.

TECHNICAL FIELD

This invention is in the field of *Neisseria meningitidis*.

BACKGROUND ART

*Neisseria meningitidis* (meningococcus) is a non-motile Gram negative diplococcus that is pathogenic in humans. It colonises the pharynx and causes meningitis (and, occasionally, septicaemia in the absence of meningitis).

All pathogenic meningococci have a polysaccharide capsule. These polysaccharides form the basis of available vaccines against meningococcus serogroups A, C, W135 and Y, but they are inappropriate for use against serogroup B. There has thus been a great deal of research into identifying alternative antigens for immunising against serogroup B. Such alternatives have included proteins, the lipopolysaccharide, and outer membrane vesicles.

References 1 to 7 disclose various polypeptides derived from the genome sequence of a serogroup B meningococcus, and they select specific sequences for use in vaccines. Genome sequence for a serogroup A strain is disclosed in reference 8.

It is an object of the invention to provide further polypeptides for use in the development of vaccines for preventing and/or treating meningococcal infections. In particular, it is an object to provide polypeptides for use in improved vaccines for preventing and/or treating meningococcal meningitis. The polypeptides may also be useful for diagnostic purposes, and as targets for antibiotics.

DISCLOSURE OF THE INVENTION

Polypeptides

The invention provides polypeptides comprising the meningococcal amino acid sequences disclosed in the examples. These amino acid sequences are the even SEQ ID NOs between 2 and 78. There are thus 39 amino acid sequences, and these are referred to as B269_nn, where nn is a number between 01 and 50 (there are eleven B269_nn numbers that have no sequence: 02, 03, 04, 05, 06, 07, 08, 09, 10, 12 & 40). Two preferred sequences are B269_32 and B269_37.

The invention also provides polypeptides comprising amino acid sequences that have sequence identity to the meningococcal amino acid sequences disclosed in the examples. Depending on the particular sequence, the degree of sequence identity is preferably greater than 50% (e.g. 60%, 70%, 75%, 80%, 85%, 90%, 91%, 92%, 93%, 94%, 95%, 96%, 97%, 98%, 99% or more). These polypeptides include homologs, orthologs, allelic variants and functional mutants. Typically, 50% identity or more between two polypeptide sequences is considered to be an indication of functional equivalence. For any particular SEQ ID, the degree of sequence identity is preferably greater than both of the values in columns (B) and (A) of Table II herein, and is more preferably greater than all of the values in columns (C), (B) and (A) for that SEQ ID.

These polypeptide may, compared to the meningococcal sequences of the examples, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cystine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may also include one or more (e.g. 1, 2, 3, 4, 5, 6, 7, 8, 9, 10, etc.) single amino acid deletions relative to the meningococcal sequences of the examples. The polypeptides may also include one or more (e.g. 1, 2, 3, 4, 5, 6, 7, 8, 9, 10, etc.) insertions (e.g. each of 1, 2, 3, 4 or 5 amino acids) relative to the meningococcal sequences of the examples.

The invention further provides polypeptides comprising fragments of the meningococcal amino acid sequences disclosed in the examples. The fragments should comprise at least n consecutive amino acids from the sequences and, depending on the particular sequence, n is 7 or more (e.g. 8, 10, 12, 14, 16, 18, 20, 22, 24, 26, 28, 30, 35, 40, 45, 50, 60, 70, 80, 90, 100 or more).

The fragment may comprise at least one T-cell or, preferably, a B-cell epitope of the sequence. T- and B-cell epitopes can be identified empirically (e.g. using PEPSCAN [9,10] or similar methods), or they can be predicted (e.g. using the Jameson-Wolf antigenic index [11], matrix-based approaches [12], TEPITOPE [13], neural networks [14], OptiMer & EpiMer [15, 16], ADEPT [17], Tsites [18], hydrophilicity [19], antigenic index [20] or the methods disclosed in reference 21 etc.). Other preferred fragments are (a) the N-terminal signal peptides of the meningococcal polypeptides of the invention, (b) the meningococcal polypeptides, but without their N-terminal signal peptides, (c) the meningococcal polypeptides, but without their N-terminal amino acid residue.

Polypeptides of the invention can be prepared in many ways e.g. by chemical synthesis (in whole or in part), by digesting longer polypeptides using proteases, by translation from RNA, by purification from cell culture (e.g. from recombinant expression), from the organism itself (e.g. after bacterial culture, or direct from patients), etc. A preferred method for production of peptides <40 amino acids long involves in vitro chemical synthesis [22,23]. Solid-phase peptide synthesis is particularly preferred, such as methods based on tBoc or Fmoc [24] chemistry. Enzymatic synthesis [25] may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [26]. Where D-amino acids are included, however, it is preferred to use chemical synthesis. Polypeptides of the invention may have covalent modifications at the C-terminus and/or N-terminus.

Polypeptides of the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides of the invention are preferably provided in purified or substantially purified form i.e. substantially free from other polypeptides (e.g. free from naturally-occurring polypeptides), particularly from other meningococcal or host cell polypeptides, and are generally at least about 50% pure (by weight), and usually at least about 90% pure i.e. less than about 50%, and more preferably less than about 10% (e.g. 5%) of a composition is made up of other expressed polypeptides. Polypeptides of the invention are preferably meningococcal polypeptides. Polypeptides of the invention preferably have the function indicated in Table I for the relevant sequence.

Polypeptides of the invention may be attached to a solid support. Polypeptides of the invention may comprise a detectable label (e.g. a radioactive or fluorescent label, or a biotin label).

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains. Polypeptides of the invention can be naturally or non-naturally glycosylated (i.e. the polypeptide has a glycosylation pattern that differs from the glycosylation pattern found in the corresponding naturally occurring polypeptide).

The invention provides polypeptides comprising a sequence —X—Y— or —Y—X—, wherein: —X— is an amino acid sequence as defined above and —Y— is not a sequence as defined above i.e. the invention provides fusion proteins. Where the N-terminus codon of a polypeptide-coding sequence is not ATG then that codon will be translated as the standard amino acid for that codon rather than as a Met, which occurs when the codon is a start codon.

The invention provides a process for producing polypeptides of the invention, comprising the step of culturing a host cell of to the invention under conditions which induce polypeptide expression.

The invention provides a process for producing a polypeptide of the invention, wherein the polypeptide is synthesised in part or in whole using chemical means.

The invention provides a composition comprising two or more polypeptides of the invention.

The invention also provides a hybrid polypeptide represented by the formula $NH_2$-A-[-X-L-]$_n$-B—COOH, wherein X is a polypeptide of the invention as defined above, L is an optional linker amino acid sequence, A is an optional N-terminal amino acid sequence, B is an optional C-terminal amino acid sequence, and n is an integer greater than 1. The value of n is between 2 and x, and the value of x is typically 3, 4, 5, 6, 7, 8, 9 or 10. Preferably n is 2, 3 or 4; it is more preferably 2 or 3; most preferably, n=2. For each n instances, —X— may be the same or different. For each n instances of [—X-L-], linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s)-L- will typically be short (e.g. 20 or fewer amino acids i.e. 19, 18, 17, 16, 15, 14, 13, 12, 11, 10, 9, 8, 7, 6, 5, 4, 3, 2, 1). Examples include short peptide sequences which facilitate cloning, poly-glycine linkers (i.e. Gly$_n$, where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. -A- and —B— are optional sequences which will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct polypeptide trafficking, or short peptide sequences which facilitate cloning or purification (e.g. histidine tags i.e. His$_n$ where n=3, 4, 5, 6, 7, 8, 9, 10 or more). Other suitable N-terminal and C-terminal amino acid sequences will be apparent to those skilled in the art.

Various tests can be used to assess the in vivo immunogenicity of polypeptides of the invention. For example, polypeptides can be expressed recombinantly and used to screen patient sera by immunoblot. A positive reaction between the polypeptide and patient serum indicates that the patient has previously mounted an immune response to the protein in question i.e. the protein is an immunogen. This method can also be used to identify immunodominant proteins.

Antibodies

The invention provides antibodies that bind to polypeptides of the invention. These may be polyclonal or monoclonal and may be produced by any suitable means (e.g. by recombinant expression). To increase compatibility with the human immune system, the antibodies may be chimeric or humanised (e.g. refs. 27 & 28), or fully human antibodies may be used. The antibodies may include a detectable label (e.g. for diagnostic assays). Antibodies of the invention may be attached to a solid support. Antibodies of the invention are preferably neutralising antibodies.

Monoclonal antibodies are particularly useful in identification and purification of the individual polypeptides against which they are directed. Monoclonal antibodies of the invention may also be employed as reagents in immunoassays, radioimmunoassays (RIA) or enzyme-linked immunosorbent assays (ELISA), etc. In these applications, the antibodies can be labelled with an analytically-detectable reagent such as a radioisotope, a fluorescent molecule or an enzyme. The monoclonal antibodies produced by the above method may also be used for the molecular identification and characterization (epitope mapping) of polypeptides of the invention.

Antibodies of the invention are preferably provided in purified or substantially purified form. Typically, the antibody will be present in a composition that is substantially free of other polypeptides e.g. where less than 90% (by weight), usually less than 60% and more usually less than 50% of the composition is made up of other polypeptides.

Antibodies of the invention can be of any isotype (e.g. IgA, IgG, IgM i.e. but will generally be IgG. Within the IgG isotype, antibodies may be IgG1, IgG2, IgG3 or IgG4 subclass. Antibodies of the invention Antibodies of the invention can take various forms, including whole antibodies, antibody fragments such as F(ab')2 and F(ab) fragments, Fv fragments (non-covalent heterodimers), single-chain antibodies such as single chain Fv molecules (scFv), minibodies, oligobodies, etc. The term "antibody" does not imply any particular origin, and includes antibodies obtained through non-conventional processes, such as phage display.

The invention provides a process for detecting polypeptides of the invention, comprising the steps of: (a) contacting an antibody of the invention with a biological sample under conditions suitable for the formation of an antibody-antigen complexes; and (b) detecting said complexes.

The invention provides a process for detecting antibodies of the invention, comprising the steps of: (a) contacting a polypeptide of the invention with a biological sample (e.g. a blood or serum sample) under conditions suitable for the formation of an antibody-antigen complexes; and (b) detecting said complexes.

Nucleic Acids

The invention provides nucleic acid comprising the meningococcal nucleotide sequences disclosed in the examples. These nucleic acid sequences are the odd SEQ ID NOs between 1 and 77.

The invention also provides nucleic acid comprising nucleotide sequences having sequence identity to the meningococcal nucleotide sequences disclosed in the examples.

The invention also provides nucleic acid which can hybridize to the meningococcal nucleic acid disclosed in the examples. Hybridization reactions can be performed under conditions of different "stringency". Conditions that increase stringency of a hybridization reaction of widely known and published in the art [e.g. page 7.52 of reference 29]. Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art [e.g. see references 29-32, etc.].

In some embodiments, nucleic acid of the invention hybridizes to a target of the invention under low stringency conditions; in other embodiments it hybridizes under intermediate stringency conditions; in preferred embodiments, it hybridizes under high stringency conditions. An exemplary set of low stringency hybridization conditions is 50° C. and 10×SSC. An exemplary set of intermediate stringency hybridization conditions is 55° C. and 1×SSC. An exemplary set of high stringency hybridization conditions is 68° C. and 0.1×SSC.

Nucleic acid comprising fragments of these sequences are also provided. These should comprise at least n consecutive nucleotides from the meningococcal sequences and, depending on the particular sequence, n is 10 or more (e.g. 12, 14, 15, 18, 20, 25, 30, 35, 40, 50, 60, 70, 80, 90, 100, 150, 200 or more).

The invention provides nucleic acid of formula 5'-X—Y—Z-3', wherein: —X— is a nucleotide sequence consisting of x nucleotides; —Z— is a nucleotide sequence consisting of z nucleotides; —Y— is a nucleotide sequence consisting of either (a) a fragment of one of the odd-numbered SEQ ID NOS: 1 to 77, or (b) the complement of (a); and said nucleic acid 5'—X—Y—Z-3' is neither (i) a fragment of one of the odd-numbered SEQ ID NOS: 1 to 77 nor (ii) the complement of (i). The —X— and/or —Z— moieties may comprise a promoter sequence (or its complement).

The invention also provides nucleic acid encoding the polypeptides and polypeptide fragments of the invention.

The invention includes nucleic acid comprising sequences complementary to the sequences disclosed in the sequence listing (e.g. for antisense or probing, or for use as primers), as well as the sequences in the orientation actually shown.

Nucleic acids of the invention can be used in hybridisation reactions (e.g. Northern or Southern blots, or in nucleic acid microarrays or 'gene chips') and amplification reactions (e.g. PCR, SDA, SSSR, LCR, TMA, NASBA, etc.) and other nucleic acid techniques.

Nucleic acid according to the invention can take various forms (e.g. single-stranded, double-stranded, vectors, primers, probes, labelled etc.). Nucleic acids of the invention may be circular or branched, but will generally be linear. Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids of the invention are preferably provided in purified or substantially purified form i.e. substantially free from other nucleic acids (e.g. free from naturally-occurring nucleic acids), particularly from other *Haemophilus* or host cell nucleic acids, generally being at least about 50% pure (by weight), and usually at least about 90% pure. Nucleic acids of the invention are preferably *H. influenzae* nucleic acids.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acid of the invention may be attached to a solid support (e.g. a bead, plate, filter, film, slide, microarray support, resin, etc.). Nucleic acid of the invention may be labelled e.g. with a radioactive or fluorescent label, or a biotin label. This is particularly useful where the nucleic acid is to be used in detection techniques e.g. where the nucleic acid is a primer or as a probe.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids of the invention comprise meningococcal sequences as defined above, but they may also comprise non-meningococcal sequences (e.g. in nucleic acids of formula 5'-X—Y—Z-3', as defined above). This is particularly useful for primers, which may thus comprise a first sequence complementary to a PCAV nucleic acid target and a second sequence which is not complementary to the nucleic acid target. Any such non-complementary sequences in the primer are preferably 5' to the complementary sequences. Typical non-complementary sequences comprise restriction sites or promoter sequences.

Nucleic acids of the invention can be prepared in many ways e.g. by chemical synthesis (at least in part), by digesting longer nucleic acids using nucleases (e.g. restriction enzymes), by joining shorter nucleic acids (e.g. using ligases or polymerases), from genomic or cDNA libraries, etc.

Nucleic acids of the invention may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which is designed to result in the production of a recombinant virus or virus-like particle, or "shuttle vectors", which comprise the attributes of more than one type of vector. Preferred vectors are plasmids. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention.

Where a nucleic acid is DNA, it will be appreciated that "U" in a RNA sequence will be replaced by "T" in the DNA. Similarly, where a nucleic acid is RNA, it will be appreciated that "T" in a DNA sequence will be replaced by "U" in the RNA.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T). The terms also imply a direction—the complement of 5'-ACAGT-3' is 5'-ACTGT-3' rather than 5'-TGTCA-3'.

Nucleic acids of the invention can be used, for example: to produce polypeptides; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid of the invention, wherein the nucleic acid is synthesised in part or in whole using chemical means.

The invention provides vectors comprising nucleotide sequences of the invention (e.g. cloning or expression vectors) and host cells transformed with such vectors.

The invention also provides a kit comprising primers (e.g. PCR primers) for amplifying a template sequence contained within a meningococcus nucleic acid sequence, the kit comprising a first primer and a second primer, wherein the first primer is substantially complementary to said template sequence and the second primer is substantially complementary to a complement of said template sequence, wherein the parts of said primers which have substantial complementarity define the termini of the template sequence to be amplified. The first primer and/or the second primer may include a detectable label (e.g. a fluorescent label).

The invention also provides a kit comprising first and second single-stranded oligonucleotides which allow amplification of a meningococcal template nucleic acid sequence contained in a single- or double-stranded nucleic acid (or mixture thereof), wherein: (a) the first oligonucleotide comprises a primer sequence which is substantially complementary to said template nucleic acid sequence; (b) the second oligonucleotide comprises a primer sequence which is substantially complementary to the complement of said template nucleic acid sequence; (c) the first oligonucleotide and/or the second oligonucleotide comprise(s) sequence which is not complementary to said template nucleic acid; and (d) said primer sequences define the termini of the template sequence to be amplified. The non-complementary sequence(s) of feature (c) are preferably upstream of (i.e. 5' to) the primer sequences. One or both of these (c) sequences may comprise a restriction site [e.g. ref. 33] or a promoter sequence [e.g. ref. 34]. The first oligonucleotide and/or the second oligonucleotide may include a detectable label (e.g. a fluorescent label).

The template sequence may be any part of a genome sequence.

The invention provides a process for detecting nucleic acid of the invention, comprising the steps of: (a) contacting a nucleic probe according to the invention with a biological sample under hybridising conditions to form duplexes; and (b) detecting said duplexes.

The invention provides a process for detecting meningococcus in a biological sample (e.g. blood), comprising the step of contacting nucleic acid according to the invention with the biological sample under hybridising conditions. The process may involve nucleic acid amplification (e.g. PCR, SDA, SSSR, LCR, TMA, NASBA, etc.) or hybridisation (e.g. microarrays, blots, hybridisation with a probe in solution etc.).

The invention provides a process for preparing a fragment of a target sequence, wherein the fragment is prepared by extension of a nucleic acid primer. The target sequence and/or the primer are nucleic acids of the invention. The primer extension reaction may involve nucleic acid amplification (e.g. PCR, SDA, SSSR, LCR, TMA, NASBA, etc.).

Nucleic acid amplification according to the invention may be quantitative and/or real-time.

For certain embodiments of the invention, nucleic acids are preferably at least 7 nucleotides in length (e.g. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 90, 100, 110, 120, 130, 140, 150, 160, 170, 180, 190, 200, 225, 250, 275, 300 nucleotides or longer).

For certain embodiments of the invention, nucleic acids are preferably at most 500 nucleotides in length (e.g. 450, 400, 350, 300, 250, 200, 150, 140, 130, 120, 110, 100, 90, 80, 75, 70, 65, 60, 55, 50, 45, 40, 39, 38, 37, 36, 35, 34, 33, 32, 31, 30, 29, 28, 27, 26, 25, 24, 23, 22, 21, 20, 19, 18, 17, 16, 15 nucleotides or shorter).

Primers and probes of the invention, and other nucleic acids used for hybridization, are preferably between 10 and 30 nucleotides in length (e.g. 10, 11, 12, 13, 14, 15, 16, 17, 18, 19, 20, 21, 22, 23, 24, 25, 26, 27, 28, 29, or 30 nucleotides).

Pharmaceutical Compositions

The invention provides compositions comprising: (a) polypeptide, antibody, and/or nucleic acid of the invention; and (b) a pharmaceutically acceptable carrier. These compositions may be suitable as immunogenic compositions, for instance, or as diagnostic reagents, or as vaccines. Vaccines according to the invention may either be prophylactic (i.e. to prevent infection) or therapeutic (i.e. to treat infection), but will typically be prophylactic.

A 'pharmaceutically acceptable carriers' includes any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in ref. 141.

Compositions of the invention may include an antimicrobial, particularly if packaged in a multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

Polypeptides of the invention may be administered in conjunction with other immunoregulatory agents. In particular, compositions will usually include a vaccine adjuvant. Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 35], or mixtures of different mineral compounds, with the compounds taking any suitable form (e.g. gel, crystalline, amorphous, etc.), and with adsorption being preferred. The mineral containing compositions may also be formulated as a particle of metal salt [36].

Aluminium phosphates are particularly preferred, particularly in compositions which include a *H. influenzae* saccharide antigen, and a typical adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where there is more than one conjugate in a composition, not all conjugates need to be adsorbed.

B. Oil Emulsions

Oil emulsion compositions suitable for use as adjuvants in the invention include squalene-water emulsions, Such as MF59 [Chapter 10 of ref. 35; see also ref. 37] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of Ref 35]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaparilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 38. Saponin formulations may also comprise a sterol, such as cholesterol [39].

Combinations of saponins and cholesterols can be used to form unique particles called immunostimulating complexes (ISCOMs) [chapter 23 of ref. 35]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 39-41. Optionally, the ISCOMS may be devoid of additional detergent [42].

A review of the development of saponin based adjuvants can be found in refs. 43 & 44.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 45-50. Virosomes are discussed further in, for example, ref. 51

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 52. Such "small particles" of 3dMPL are small enough to be sterile filtered through a 0.22 μm membrane [52]. Other non-toxic LPS derivatives include monophosphoryl lipid A mimics, such as aminoalkyl glucosaminide phosphate derivatives e.g. RC-529 [53,54].

Lipid A derivatives include derivatives of lipid A from *Escherichia coli* such as OM-174. OM-174 is described for example in refs. 55 & 56.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 57, 58 and 59 disclose possible analog substitutions e.g. replacement of guanosine with 2'-deoxy-7-deazaguanosine. The adjuvant effect of CpG oligonucleotides is further discussed in refs. 60-65.

The CpG sequence may be directed to TLR9, such as the motif GTCGTT or TTCGTT [66]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 67-69. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 66 & 70-72.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 73 and as parenteral adjuvants in ref. 74. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivaties thereof, particularly LT-K63 and LT-R72, as adjuvants can be found in refs. 75-82. Numerical reference for amino acid substitutions is preferably based on the alignments of the A and B Subunits of ADP-ribosylating toxins set forth in ref. 83, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [84], etc.) [85], interferons (e.g. interferon- G. Bioadhesives and Mucoadhesives Bioadhesives and mucoadhesives may also be used as adjuvants in the invention. Suitable bioadhesives include esterified hyaluronic acid microspheres [86] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [87].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref 35)

Examples of liposome formulations suitable for use as adjuvants are described in refs. 88-90.

J. Polyoxyethylene Ether and Polyoxyethylene Ester Formulations

Adjuvants suitable for use in the invention include polyoxyethylene ethers and polyoxyethylene esters [91]. Such formulations further include polyoxyethylene sorbitan ester surfactants in combination with an octoxynol [92] as well as polyoxyethylene alkyl ethers or ester surfactants in combination with at least one additional non-ionic surfactant such as an octoxynol [93]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K Polyphosphazene (PCPP)

PCPP formulations are described, for example, in refs. 94 and 95.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 96 and 97.

The invention may also comprise combinations of aspects of one or more of the adjuvants identified above. For example, the following adjuvant compositions may be used in the invention: (1) a saponin and an oil-in-water emulsion [98]; (2) a saponin (e.g. QS21)+a non-toxic LPS derivative (e.g. 3dMPL) [99]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [100]; (5) combinations of 3dMPL with, for example, QS21 and/or oil-in-water emulsions [101]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 35.

The use of an aluminium hydroxide or aluminium phosphate adjuvant is particularly preferred, and antigens are generally adsorbed to these salts. Calcium phosphate is another preferred adjuvant.

The pH of compositions of the invention is preferably between 6 and 8, preferably about 7. Stable pH may be maintained by the use of a buffer. Where a composition comprises an aluminium hydroxide salt, it is preferred to use a histidine buffer [102]. The composition may be sterile and/or pyrogen-free. Compositions of the invention may be isotonic with respect to humans.

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

Compositions of the invention may be packaged in unit dose form or in multiple dose form. For multiple dose forms, vials are preferred to pre-filled syringes. Effective dosage volumes can be routinely established, but a typical human dose of the composition for injection has a volume of 0.5 min.

Where a composition of the invention is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials, and a typical quantity of each meningococcal saccharide antigen per dose is between 1 µg and 10 mg per antigen.

Pharmaceutical Uses

The invention also provides a method of treating a patient, comprising administering to the patient a therapeutically effective amount of a composition of the invention. The patient may either be at risk from the disease themselves or may be a pregnant woman ('maternal immunisation').

The invention provides nucleic acid, polypeptide, or antibody of the invention for use as medicaments (e.g. as immunogenic compositions or as vaccines, including for use in treating or preventing disease and/or infection caused by meningococcus) or as diagnostic reagents. It also provides the use of nucleic acid, polypeptide, or antibody of the invention in the manufacture of: (i) a medicament for treating or preventing disease and/or infection caused by meningococcus; (ii) a diagnostic reagent for detecting the presence of meningococcus or of antibodies raised against meningococcus; and/or (iii) a reagent which can raise antibodies against meningococcus. Said meningococcus can be of any serogroup or strain, but is preferably in serogroup B. Said disease may be, for instance, bacterial meningitis (and particularly meningococcal meningitis) or septicaemia.

The patient is preferably a human. Where the vaccine is for prophylactic use, the human is preferably a child (e.g. a toddler or infant) or teenager e.g. ages 0-18 years; where the vaccine is for therapeutic use, the human is preferably an adult e.g. aged 18-55 years. A vaccine intended for children may also be administered to adults e.g. to assess safety, dosage, immunogenicity, etc.

One way of checking efficacy of therapeutic treatment involves monitoring meningococcal infection after administration of the composition of the invention. One way of checking efficacy of prophylactic treatment involves monitoring immune responses against an administered polypeptide after administration. Immunogenicity of compositions of the invention can be determined by administering them to test subjects (e.g. children 12-16 months age, or animal models) and then determining standard parameters including ELISA titres (GMT) of IgG. These immune responses will generally be determined around 4 weeks after administration of the composition, and compared to values determined before administration of the composition. Where more than one dose of the composition is administered, more than one post-administration determination may be made. A standard method for assessing prophylactic efficacy for meningococci is the serum bactericidal assay (SBA). Administration preferably results in an increase in SBA titre for the relevant serogroup of at least 4-fold, and preferably at least 8-fold, measured with human complement [103]. If rabbit complement is used to measure SBA titres then the titre increase is preferably at least 128-fold.

Administration of polypeptide antigens is a preferred method of treatment for inducing immunity. Administration of antibodies of the invention is another preferred method of treatment. This method of passive immunisation is particularly useful for newborn children or for pregnant women. This method will typically use monoclonal antibodies, which will be humanised or fully human.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Bacterial infections affect various areas of the body and so compositions may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 104 & 105].

Further Antigenic Components of Compositions of the Invention

The invention also provides a composition comprising a polypeptide or the invention and one or more of the following further antigens:

a saccharide antigen from *N. meningitidis* serogroup A, C, W135 and/or Y (preferably all four), such as the oligosaccharide disclosed in ref. 106 from serogroup C [see also ref. 107] or the oligosaccharides of ref. 108.

a saccharide antigen from *Streptococcus pneumoniae* [e.g. 109, 110, 111].

an antigen from hepatitis A virus, such as inactivated virus [e.g. 112, 113].

an antigen from hepatitis B virus, such as the surface and/or core antigens [e.g. 113, 114].

a diphtheria antigen, such as a diphtheria toxoid [e.g. chapter 3 of ref. 115] e.g. the $CRM_{197}$ mutant [e.g. 116].

a tetanus antigen, such as a tetanus toxoid [e.g. chapter 4 of ref. 115].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 117 & 118].

a saccharide antigen from *Haemophilus influenzae* B [e.g. 107].

polio antigen(s) [e.g. 119, 120] such as IPV.

measles, mumps and/or rubella antigens [e.g. chapters 9, 10 & 11 of ref. 115].

influenza antigen(s) [e.g. chapter 19 of ref. 115], such as the haemagglutinin and/or neuraminidase surface proteins.

an antigen from *Moraxella catarrhalis* [e.g. 121].

an protein antigen from *Streptococcus agalactiae* (group B *streptococcus*) [e.g. 122, 123].

a saccharide antigen from *Streptococcus agalactiae* (group B *streptococcus*).

an antigen from *Streptococcus pyogenes* (group A *streptococcus*) [e.g. 123, 124, 125].

an antigen from *Staphylococcus aureus* [e.g. 126].

The composition may comprise one or more of these further antigens.

Toxic protein antigens may be detoxified where necessary (e.g. detoxification of pertussis toxin by chemical and/or genetic means [118]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates include diphtheria toxin, tetanus toxin, the *N. meningitidis* outer membrane protein [127], synthetic peptides [128,129], heat shock proteins [130,131], pertussis proteins [132,133], protein D from *H. influenzae* [134], cytokines [135], lymphokines [135], streptococcal proteins, hormones [135], growth factors [135], toxin A or B from *C. difficile* [136], iron-uptake proteins [137], etc. A preferred carrier protein is the CRM197 diphtheria toxoid [138].

Antigens in the composition will typically be present at a concentration of at least 1 μg/ml each. In general, the concentration of any given antigen will be sufficient to elicit an immune response against that antigen.

As an alternative to using proteins antigens in the immunogenic compositions of the invention, nucleic acid (preferably DNA e.g. in the form of a plasmid) encoding the antigen may be used.

Antigens are preferably adsorbed to an aluminium salt.

Screening Methods

The invention provides a process for determining whether a test compound binds to a polypeptide of the invention. If a test compound binds to a polypeptide of the invention and this binding inhibits the life cycle of meningococcus, then the test compound can be used as an antibiotic or as a lead compound for the design of antibiotics. The process will typically comprise the steps of contacting a test compound with a polypeptide of the invention, and determining whether the test compound binds to said polypeptide. Preferred polypeptides of the invention for use in these processes are enzymes (e.g. tRNA synthetases), membrane transporters and ribosomal polypeptides. Suitable test compounds include polypeptides, polypeptides, carbohydrates, lipids, nucleic acids (e.g. DNA, RNA, and modified forms thereof), as well as small organic compounds (e.g. MW between 200 and 2000 Da). The test compounds may be provided individually, but will typically be part of a library (e.g. a combinatorial library). Methods for detecting a binding interaction include NMR, filter-binding assays, gel-retardation assays, displacement assays, surface plasmon resonance, reverse two-hybrid etc. A compound which binds to a polypeptide of the invention can be tested for antibiotic activity by contacting the compound with meningococcus bacteria and then monitoring for inhibition of growth. The invention also provides a compound identified using these methods.

Preferably, the process comprises the steps of: (a) contacting a polypeptide of the invention with one or more candidate compounds to give a mixture; (b) incubating the mixture to allow polypeptide and the candidate compound(s) to interact; and (c) assessing whether the candidate compound binds to the polypeptide or modulates its activity.

Once a candidate compound has been identified in vitro as a compound that binds to a polypeptide of the invention then it may be desirable to perform further experiments to confirm the in vivo function of the compound in inhibiting bacterial growth and/or survival. Thus the method comprise the further step of contacting the compound with a meningococcus and assessing its effect.

The polypeptide used in the screening process may be free in solution, affixed to a solid support, located on a cell surface or located intracellularly. Preferably, the binding of a candidate compound to the polypeptide is detected by means of a label directly or indirectly associated with the candidate compound. The label may be a fluorophore, radioisotope, or other detectable label.

General

The invention provides a computer-readable medium (e.g. a floppy disk, a hard disk, a CD-ROM, a DVD etc.) and/or a computer memory and/or a computer database containing one or more of the sequences in the sequence listing.

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Identity between polypeptides is preferably determined by the Smith-Waterman homology search algorithm as implemented in the MPSRCH program (Oxford Molecular), using an affine gap search with parameters gap open penalty=12 and gap extension penalty=1. Identity between sequences is preferably also determined by the Smith-Waterman homology search algorithm.

The N-terminus residues in the amino acid sequences in the sequence listing are given as the amino acid encoded by the first codon in the corresponding nucleotide sequence. Where the first codon is not ATG, it will be understood that it will be translated as methionine when the codon is a start codon, but will be translated as the indicated non-Met amino acid when the sequence is at the C-terminus of a fusion partner. The invention specifically discloses and encompasses each of the amino acid sequences of the sequence listing having a N-terminus methionine residue (e.g. a formyl-methionine residue) in place of any indicated non-Met residue.

Alternative start codons can be used in biology. The amino acid sequences in the sequence listing are based on particular start codons, but downstream start codons may alternatively be used. Thus the invention specifically discloses and encompasses each of the amino acid sequences of the sequence listing, starting at any methionine residue from the sequence that is downstream of the N-terminal residue shown in the sequence listing (e.g. SEQ ID NOs: 5 & 10).

As indicated in the above text, nucleic acids and polypeptides of the invention may include sequences that:
(a) are identical (i.e. 100% identical) to the sequences disclosed in the sequence listing;
(b) share sequence identity with the sequences disclosed in the sequence listing;
(c) have 1, 2, 3, 4, 5, 6, 7, 8, 9 or 10 single nucleotide or amino acid alterations (deletions, insertions, substitutions), which may be at separate locations or may be contiguous, as compared to the sequences of (a) or (b); and
(d) when aligned with a particular sequence from the sequence listing using a pairwise alignment algorithm, a moving window of x monomers (amino acids or nucleotides) moving from start (N-terminus or 5') to end (C-terminus of 3'), such that for an alignment that extends to p monomers (where p>x) there are p−x+1 such windows, each window has at least x·y identical aligned monomers, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [139], using default parameters (e.g. with Gap opening penalty=10.0, and with Gap extension penalty=0.5, using the EBLOSUM62 scoring matrix). This algorithm is conveniently implemented in the needle tool in the EMBOSS package [140].

The nucleic acids and polypeptides of the invention may additionally have further sequences to the N-terminus/5' and/or C-terminus/3' of these sequences (a) to (d).

The practice of the present invention will employ, unless otherwise indicated, conventional methods of chemistry, biochemistry, molecular biology, immunology and pharmacology, within the skill of the art. Such techniques are explained fully in the literature. See, e.g., references 141-148, etc.

MODES FOR CARRYING OUT THE INVENTION

Various encoded amino acid sequences have been identified in the genome of the M04-240196 strain of serogroup B *N. meningitidis*. 39 of them have been selected as useful antigens, based on various criteria, and their gene and amino acid sequences are given in the sequence listing.

Predicted biological functions are given in Table I, but the antigens' precise roles in meningococcus biology are not as important as their ability to function as immunogens. Table I also notes the closest match in the published serogroup A and B genomes in references 6 and 8, as well as in the unpublished genome of serogroup C strain FAM18. Where a sequence has more than 95% identity to a known sequence (and particularly where it has 100% identity) then the invention is more concerned with identifying the protein's useful antigenic properties than identifying the protein per se.

In addition to the annotations and comparisons, further features of interest include: B269_17 contains an intein domain; B269_34 has a junction sequence at its C-terminus; a transmembrane domain is present in B269_05, B269_10, B269_18, B269-24; and five transmembrane domains are present in B269_15 and B269_29.

Using the sequence information herein, the proteins can readily be expressed in recombinant hosts and used to generate immune responses using techniques known in the art.

For instance, sequences encoding B269 proteins 11, 13, 14, 15, 17, 24, 25, 26, 29, 31, 32, 34, 36, 37, 51, 52, 53, 54, 55, 56, 57, 58 and 59 were inserted into expression vectors with a C-terminal poly-histidine tag. B269_ proteins 14, 29, 31, 34, 37 were also expressed in a domain-truncated form. GST fusions of 37, 54, 55 and 57 were also prepared. Expressed proteins were purified from *E. coli*. Without any optimisation of expression, various degrees of purity were seen e.g. from 20% purity with domain B269_14 and B269_32, up to 95% purity with B269_51. Soluble expression was seen with B269_ proteins 13, 24, 25, $31_{domain}$, 32, 51, 53 and 56.

Antibodies were raised against expressed proteins by injecting them into mice with Freund's complete adjuvant or aluminium hydroxide. Antisera were then used in western blots or FACS binding assays against meningococci. The following B269_ proteins could be detected by western blot: 13; 25; $29_{domain}$; 31; $34_{domain}$; 51; 52; and 53. In addition, the following proteins could be detected in the blots at particular MWs: 11 (40 kDa); 24 (20 kDa); and 26 (28 kDa). FACS revealed the following proteins: 17; 24; 25; 26; $29_{domain}$; $34_{domain}$; and 53.

It will be understood that the invention has been described by way of example only and modifications may be made whilst remaining within the scope and spirit of the invention.

TABLE I

| Annotations | | | | |
|---|---|---|---|---|
| B269 | SEQ ID | aa | Localisation * | Annotation |
| 01 | 2 | 588 | O | PilC protein |
| 11 | 4 | 320 | O | putative MafA-like adhesin |
| 13 | 6 | 387 | C | Cupin superfamily protein |
| 14 | 8 | 420 | I | membrane-fusion protein |
| 15 | 10 | 670 | I | peptidase, C39 family |
| 16 | 12 | 331 | P | putative peptidyl-prolyl cis-trans isomerase |
| 17 | 14 | 209 | S | conserved hypothetical protein |
| 18 | 16 | 265 | 0 | opacity protein |
| 19 | 18 | 680 | I | transferrin-binding protein 2 |
| 20 | 20 | 1370 | S | hemagglutinin-hemolysin-related protein |
| 21 | 22 | 734 | S | hemagglutinin-hemolysin-related protein |
| 22 | 24 | 887 | S | hemagglutinin-hemolysin-related protein |
| 23 | 26 | 794 | S | hemagglutinin-hemolysin-related protein |
| 24 | 28 | 206 | C | conserved hypothetical protein |
| 25 | 30 | 1502 | S | HlyJ haemolysin-like protein |
| 26 | 32 | 257 | C | conserved hypothetical protein TIGR00294 |
| 27 | 34 | 237 | I | putative thiosulphate sulphur transferase |
| 28 | 36 | 402 | C | probable: Putative GlcNAc transferase19 |

TABLE I-continued Annotations

| B269 | SEQ ID | aa | Localisation * | Annotation |
|---|---|---|---|---|
| 29 | 38 | 297 | O | conserved hypothetical protein |
| 30 | 40 | 226 | C | opacity protein Opa115 |
| 31 | 42 | 588 | O | YadA-like C-terminal region family |
| 32 | 44 | 201 | C | conserved hypothetical protein |
| 33 | 46 | 337 | I | putative glycosyltransferase |
| 34 | 48 | 529 | C | Iron-regulated protein frpA |
| 35 | 50 | 676 | C | transferrin/lactoferrin binding protein B |
| 36 | 52 | 203 | C | mucin |
| 37 | 54 | 340 | C | conserved hypothetical protein |
| 38 | 56 | 376 | I | putative two component sensor kinase196 |
| 39 | 58 | 346 | P | ATP-binding region, ATPase-like: Histidine kinase A, N-terminal |
| 41 | 60 | 1026 | P | PilC protein |
| 42 | 62 | 333 | O | conserved hypothetical protein |
| 43 | 64 | 229 | C | glycosyl transferase, group 2 family protein |
| 44 | 66 | 208 | C | conserved hypothetical protein |
| 45 | 68 | 476 | C | mafB protein |
| 46 | 70 | 229 | C | adhesin MafB |
| 47 | 72 | 432 | O | transferrin binding protein B subunit19 |
| 48 | 74 | 809 | S | hemolysin-hemagglutinin-like protein HecA precursor, putative |
| 49 | 76 | 783 | S | Possible hemagglutinin (DUF637) family1 |
| 50 | 78 | 300 | S | hemagglutinin-hemolysin-related protein | aa = length of polypeptide

* Localisation key: O = outer membrane; C = cytoplasm; I = inner membrane; P = periplasmic space; S = secreted

TABLE II

Relationship to other meningococcal sequences [6, 8]

| B269 | SEQ ID | MC58 | (B) | (A) | (C) |
|---|---|---|---|---|---|
| 01 | 2 | NMB0049 | 77.6 | 78.2 | 73.1 |
| 11 | 4 | NMB0652 | 62.7 | 100 | 98.4 |
| 13 | 6 | NMB1786 | 51 | 48.4 | 80.3 |
| 14 | 8 | NMB0097 | 51.1 | 59.9 | 100 |
| 15 | 10 | NMB0098 | 64 | 28.9 | 94.9 |
| 16 | 12 | NMB0281 | 85.4 | 92.1 | 93.5 |
| 17 | 14 | NMB0369 | 83.2 | 61.7 | 91.9 |
| 18 | 16 | NMB0442 | 86.4 | 81.5 | 87.1 |
| 19 | 18 | NMB0460 | 71.5 | 70.9 | 41.8 |
| 20 | 20 | NMB1779 | 67.4 | 70 | 97.4 |
| 21 | 22 | NMB1775 | 82.6 | 87.9 | 96 |
| 22 | 24 | NMB1779 | 81.9 | 80.5 | 95.2 |
| 23 | 26 | NMB1775 | 79.2 | 89.2 | 88.9 |
| 24 | 28 | NMB0515 | 66.1 | 99.5 | 93.7 |
| 25 | 30 | NMB0585 | 85.5 | 91 | 90.9 |
| 26 | 32 | NMB0803 | 86.8 | 86.8 | 86.8 |
| 27 | 34 | NMB0841 | 84 | 95.4 | 88.1 |
| 28 | 36 | NMB0846 | 89 | 56.1 | 85.1 |
| 29 | 38 | NMB0888 | 87.9 | 79.8 | 85.2 |
| 30 | 40 | NMB1636 | 80.4 | 81.6 | 92 |
| 31 | 42 | NMB0992 | 87.4 | 90.1 | 94.6 |
| 32 | 44 | none | 41.2 | 41.2 | 70.9 |
| 33 | 46 | NMB1255 | 73 | 95.4 | 97.5 |
| 34 | 48 | NMB1415 | 89.5 | 80.5 | 98.7 |
| 35 | 50 | NMB1541 | 68.3 | 78.2 | 56.4 |
| 36 | 52 | NMB0891 | 49 | 53.4 | 78.6 |
| 37 | 54 | none | 30.7 | 33.3 | 100 |
| 38 | 56 | NMB1606 | 82.2 | 80.1 | 87 |
| 39 | 58 | NMB1606 | 83 | 85.9 | 90.9 |
| 41 | 60 | NMB1847 | 80.4 | 81.6 | 78.2 |
| 42 | 62 | NMB1870 | 87.4 | 87.4 | 74.2 |
| 43 | 64 | NMB1929 | 48.2 | 48.2 | 48.2 |
| 44 | 66 | NMB1992 | 89.9 | 81.5 | 92.8 |
| 45 | 68 | NMB2105 | 89.7 | 88.5 | 95.9 |
| 46 | 70 | NMB2105 | 88 | 96.7 | 89.9 |
| 47 | 72 | NMB2132 | 76.5 | 68.6 | 68.7 |
| 48 | 74 | NMB0493 | 85.4 | 55 | 68.2 |
| 49 | 76 | NMB1775 | 67.2 | 82.9 | 99.4 |
| 50 | 78 | NMB1779 | 51.2 | 84 | 83.3 |

'MC58' = closest match from reference 6.

Columns (a) to (c) are % matches to other sequences: (B) = ref 6; (A) = ref 8; (c) = strain FAM18.

REFERENCES

The Contents of which are Hereby Incorporated by Reference

[1] WO99/24578.
[2] WO99/36544.
[3] WO99/57280.
[4] WO00/22430.
[5] WO00/66791.
[6] Tettelin et al. (2000) *Science* 287:1809-16.
[7] Pizza et al. (2000) *Science* 287:1-1816-20.
[8] Parkhill et al. (2000) *Nature* 404:502-8.
[9] Geysen et al. (1984) *PNAS USA* 81:3998-4002.
[10] Carter (1994) *Methods Mol Biol* 36:207-23.
[11] Jameson, B A et al. 1988, *CABIOS* 4(1):181-186.
[12] Raddrizzani & Hammer (2000) *Brief Bioinform* 1(2): 179-89.
[13] De Lalla et al. (1999) *J. Immunol.* 163:1725-29.
[14] Brusic et al. (1998) *Bioinformatics* 14(2):121-30
[15] Meister et al. (1995) *Vaccine* 13(6):581-91.
[16] Roberts et al. (1996) *AIDS Res Hum Retroviruses* 12(7): 593-610.
[17] Maksyutov & Zagrebelnaya (1993) *Comput Appl Biosci* 9(3):291-7.
[18] Feller & de la Cruz (1991) *Nature* 349(6311):720-1.
[19] Hopp (1993) *Peptide Research* 6:183-190.
[20] Welling et al. (1985) *FEBS Lett.* 188:215-218.
[21] Davenport et al. (1995) *Immunogenetics* 42:392-297.
[22] Bodanszky (1993) *Principles of Peptide Synthesis* (ISBN: 0387564314).
[23] Fields et al. (1997) *Meth Enzymol* 289: *Solid-Phase Peptide Synthesis*. ISBN: 0121821900.
[24] Chan & White (2000) *Fmoc Solid Phase Peptide Synthesis*. ISBN: 0199637245.
[25] Kullmann (1987) *Enzymatic Peptide Synthesis*. ISBN: 0849368413.
[26] Ibba (1996) *Biotechnol Genet Eng Rev* 13:197-216.
[27] Breedveld (2000) *Lancet* 355(9205):735-740.
[28] Gorman & Clark (1990) *Semin. Immunol.* 2:457-466.

[29] Sambrook et al. (1989) *Molecular Cloning: A Laboratory Manual.*
[30] *Short protocols in molecular biology* (4th ed, 1999) Ausubel et al. eds. ISBN 0-471-32938-X.
[31] U.S. Pat. No. 5,707,829
[32] *Current Protocols in Molecular Biology* (F. M. Ausubel et al. eds., 1987) Supplement 30.
[33] EP-B-0509612.
[34] EP-B-0505012.
[35] *Vaccine Design* . . . (1995) eds. Powell & Newman. ISBN: 030644867X. Plenum.
[36] WO00/23105.
[37] WO90/14837.
[38] U.S. Pat. No. 5,057,540.
[39] WO96/33739.
[40] EP-A-0109942.
[41] WO96/11711.
[42] WO00/07621.
[43] Barr et al. (1998) *Advanced Drug Delivery Reviews* 32:247-271.
[44] Sjolanderet et al. (1998) *Advanced Drug Delivery Reviews* 32:321-338.
[45] Niikura et al. (2002) *Virology* 293:273-280.
[46] Lenz et al. (2001) *J Immunol* 166:5346-5355.
[47] Pinto et al. (2003) *J Infect Dis* 188:327-338.
[48] Gerber et al. (2001) *Virol* 75:4752-4760.
[49] WO03/024480
[50] WO03/024481
[51] Gluck et al. (2002) *Vaccine* 20: B10-B16.
[52] EP-A-0689454.
[53] Johnson et al. (1999) *Bioorg Med Chem Lett* 9:2273-2278.
[54] Evans et al. (2003) *Expert Rev Vaccines* 2:219-229.
[55] Meraldi et al. (2003) *Vaccine* 21:2485-2491.
[56] Pajak et al. (2003) *Vaccine* 21:836-842.
[57] Kandimalla et al. (2003) *Nucleic Acids Research* 31:2393-2400.
[58] WO02/26757.
[59] WO99/62923.
[60] Krieg (2003) *Nature Medicine* 9:831-835.
[61] McCluskie et al. (2002) *FEMS Immunology and Medical Microbiology* 32:179-185.
[62] WO98/40100.
[63] U.S. Pat. No. 6,207,646.
[64] U.S. Pat. No. 6,239,116.
[65] U.S. Pat. No. 6,429,199.
[66] Kandimalla et al. (2003) *Biochemical Society Transactions* 31 (part 3):654-658.
[67] Blackwell et al. (2003) *J Immunol* 170:4061-4068.
[68] Krieg (2002) *Trends Immunol* 23:64-65.
[69] WO01/95935.
[70] Kandimalla et al. (2003) *BBRC* 306:948-953.
[71] Bhagat et al. (2003) *BBRC* 300:853-861.
[72] WO03/035836.
[73] WO95/17211.
[74] WO98/42375.
[75] Beignon et al. (2002) *Infect Immun* 70:3012-3019.
[76] Pizza et al. (2001) *Vaccine* 19:2534-2541.
[77] Pizza et al. (2000) *Int J Med Microbiol* 290:455-461.
[78] Scharton-Kersten et al. (2000) *Infect Immun* 68:5306-5313.
[79] Ryan et al. (1999) *Infect Immun* 67:6270-6280.
[80] Partidos et al. (1999) *Immunol Lett* 67:209-216.
[81] Peppoloni et al. (2003) *Expert Rev Vaccines* 2:285-293.
[82] Pine et al. (2002) *J Control Release* 85:263-270.
[83] Domenighini et al. (1995) *Mol Microbiol* 15:1165-1167.
[84] WO99/40936.
[85] WO99/44636.
[86] Singh et al] (2001) *J Cont Release* 70:267-276.
[87] WO99/27960.
[88] U.S. Pat. No. 6,090,406
[89] U.S. Pat. No. 5,916,588
[90] EP-A-0626169.
[91] WO99/52549.
[92] WO01/21207.
[93] WO01/21152.
[94] Andrianov et al. (1998) *Biomaterials* 19:109-115.
[95] Payne et al. (1998) *Adv Drug Delivery Review* 31:185-196.
[96] Stanley (2002) *Clin Exp Dermatol* 27:571-577.
[97] Jones (2003) *Curr Opin Investig Drugs* 4:214-218.
[98] WO99/11241.
[99] WO94/00153.
[100] WO98/57659.
[101] European patent applications 0835318, 0735898 and 0761231.
[102] WO03/009869.
[103] *W.H.O. Tech. Rep. Ser.* 594:51, 1976.
[104] Almeida & Alpar (1996) *J Drug Targeting* 3:455-467.
[105] Agarwal & Mishra (1999) *Indian J Exp Biol* 37:6-16.
[106] Costantino et al. (1992) *Vaccine* 10:691-698.
[107] Costantino et al. (1999) *Vaccine* 17:1251-1263.
[108] WO03/007985.
[109] Watson (2000) *Pediatr Infect Dis J* 19:331-332.
[110] Rubin (2000) *Pediatr Clin North Am* 47:269-285, v.
[111] Jedrzejas (2001) *Microbiol Mol Biol Rev* 65:187-207.
[112] Bell (2000) *Pediatr Infect Dis J* 19:1187-1188.
[113] Iwarson (1995) *APMIS* 103:321-326.
[114] Gerlich et al. (1990) *Vaccine* 8 Suppl: S63-68 & 79-80.
[115] *Vaccines* (1988) eds. Plotkin & Mortimer. ISBN 0-7216-1946-0.
[116] Del Guidice et al. (1998) *Molecular Aspects of Medicine* 19:1-70.
[117] Gustafsson et al. (1996) *N. Engl. J. Med.* 334:349-355.
[118] Rappuoli et al. (1991) *TIBTECH* 9:232-238.
[119] Sutter et al. (2000) *Pediatr Clin North Am* 47:287-308.
[120] Zimmerman & Spann (1999) *Am Fam Physician* 59:113-118, 125-126.
[121] McMichael (2000) *Vaccine* 19 Suppl 1: S101-107.
[122] Schuchat (1999) *Lancet* 353(9146):51-6.
[123] WO02/34771.
[124] Dale (1999) *Infect Dis Clin North Am* 13:227-43, viii.
[125] Ferretti et al (2001) *PNAS USA* 98: 4658-4663.
[126] Kuroda et al. (2001) *Lancet* 357(9264):1225-1240; see also pages 1218-1219.
[127] EP-A-0372501
[128] EP-A-0378881
[129] EP-A-0427347
[130] WO93/17712
[131] WO94/03208
[132] WO98/58668
[133] EP-A-0471177
[134] WO00/56360
[135] WO91/01146
[136] WO00/61761
[137] WO01/72337
[138] *Research Disclosure*, 453077 (January 2002)
[139] Needleman & Wunsch (1970) *J. Mol. Biol.* 48, 443-453.
[140] Rice et al. (2000) *Trends Genet.* 16:276-277.
[141] Gennaro (2000) *Remington: The Science and Practice of Pharmacy.* 20th edition, ISBN: 0683306472.
[142] *Methods In Enzymology* (S. Colowick and N. Kaplan, eds., Academic Press, Inc.)

[143] *Handbook of Experimental Immunology*, Vols. I-IV (D. M. Weir and C. C. Blackwell, eds., 1986, Blackwell Scientific Publications)
[144] Sambrook, et al., *Molecular Cloning: A Laboratory Manual* (2nd Edition, 1989).
[145] *Handbook of Surface and Colloidal Chemistry* (Birdi, K. S. ed., CRC Press, 1997)
[146] *Short Protocols in Molecular Biology*, 4th ed. (Ausubel et al. eds., 1999, John Wiley & Sons)
[147] *Molecular Biology Techniques: An Intensive Laboratory Course*, (Ream et al., eds., 1998, Academic Press)
[148] *PCR (Introduction to Biotechniques Series)*, 2nd ed. (Newton & Graham eds., 1997, Springer Verlag)

The invention claimed is:

1. An isolated polypeptide comprising the amino acid sequence that has at least 90% sequence identity to SEQ ID NO: 32.

2. The isolated polypeptide of claim 1, wherein the amino acid sequence comprises SEQ ID NO: 32.

3. An isolated polypeptide comprising a fragment of at least 80 consecutive amino acids from SEQ ID NO: 32.

4. A composition comprising: (a) the polypeptide of claim 1; and (b) a pharmaceutically acceptable carrier.

5. The composition of claim 4, further comprising an adjuvant.

6. A method of inducing an immune response in a subject, comprising administering to the subject the composition of claim 4.

* * * * *

SEQUENCE LISTING

```
<160> NUMBER OF SEQ ID NOS: 78

<210> SEQ ID NO 1
<211> LENGTH: 1767
<212> TYPE: DNA
<213> ORGANISM: Neisseria meningitidis
<220> FEATURE:
<221> NAME/KEY: misc_feature
<222> LOCATION: 1744, 1745, 1746, 1747, 1748
<223> OTHER INFORMATION: n = A,T,C or G

<400> SEQUENCE: 1
atgaacgcgc aaaatctgcc tgaggtaaag tggggggcagg actatagaaa attggcgcaa      60
aaaagcaatg aacgccaatt tacccatacg actaattttt acaccaaaaa aaacgtaagt     120
ttatcattca ataataccga tgaagttgtt gctaaaaaaa acgtactgt cgttttcggc      180 gcggcgacct acctgccgcc ctacggcaag gtttccggtt ttgatgacaa aaggctgaaa     240
gagcgcggca atgccgttaa ttggattcat acgaccgacc cagggttggt aggctacagc     300
tacgaagatg ttacatgcaa cagcggcaac tgtcctgaag ttagctataa aacccaattt     360
atcttcgata atcaccagtt ggcaaaaaag aaaacagaca gcaagctgga tatatacgaa     420
gacaaaagcc gcgacaattc gcccatttac aaattgcagg attatccttg gttgggcgtg     480
tctttcaatt tgggcggaga gagctccttc aaaccaaaga gacaaggttc tttggtatct     540
tcttttagcg aggatgtgac gcagcaaaat ggtacacaag accaatacaa aggcaaaaac     600
ctcgtttata cgacagaaga ttacaataat cagggtaatc gtaaccatca ggacaaacac     660
cacgccatcg ccttttatct gaacgccaaa ctgcacctgc tggacaaaaa agggattaaa     720
gatatcaccg acaaaacagt gcagttgggt gtcttgaaac cgcgcatcga tttgacggaa     780
gcgtggaaaa acaggcatgg gagctttttt ggtaatggta attggacgtt tgaagataaa     840
ggagcagtca gcgtcaaact tatcttgccg gaagtcaaag caggccgctg catcaataaa     900
ccgaacccca atcccaaagc ccaagccctt tcccccgcac tgactgcccc cgcgctgtgg     960
ttcggacctg tgcaaaatgg taagatggag atgtattccg cttcggtttc tacctacccc    1020
gacagttcga gcagccgcat cttccttcaa aatctgaaaa gaaaaaacga ccccaacaaa    1080
cccggccgct attccctcgc agacttgagc gcgtcggaga ttaaaagtaa agagccgact    1140
ttcacagggc ggcaaaccgt catccgattg gataaaggcg tacatcagat caaacttaaa    1200
ggcaatgagg tcgaaggttt taagggaaac aacggcaacg acactttcgg cattgttagt    1260
gaagggagct tcatgcctga tgacagcgag tggaaaaaag tgctgctgcc ttggacggtt    1320
cgtgctttca atgatgacgg tcaatttaac acagtcaaca aagaagaaaa caacggcaag    1380
ccaaaataca gtcaaaaata ccgcagccgc aacaacggca agcacgagcg caatttgggc    1440
gacatcgtca acagccccat cgtggcggtc ggcgagtatt tggctacttc cgccaacgac    1500
gggatggtgc atatcttcaa aaaaagcggc ggggatgacc gcaactatag tctgaagctc    1560
agttatatcc cgggcacgat gccgcgcaag gatattcaaa gccaagactc cacccttgcc    1620
aaagagctgc gcgcctttgc cgaaaaaagc tatgtgggcg accgctacgg cgtggacggc    1680
```

-continued

```
ggctttgtct tgcgccaagt cgaatggaaa gggcaaaacc gcgtgtttat gttcggcgcg    1740
atgnnnnnca cacacttaat taattaa                                       1767
```

<210> SEQ ID NO 2
<211> LENGTH: 588
<212> TYPE: PRT
<213> ORGANISM: Neisseria meningitidis
<220> FEATURE:
<221> NAME/KEY: VARIANT
<222> LOCATION: 582, 583
<223> OTHER INFORMATION: Xaa = Any Amino Acid

<400> SEQUENCE: 2

```
Met Asn Ala Gln Asn Leu Pro Glu Val Lys Trp Gly Gln Asp Tyr Arg
  1               5                  10                  15

Lys Leu Ala Gln Lys Ser Asn Glu Arg Gln Phe Thr His Thr Thr Asn
             20                  25                  30

Phe Tyr Thr Lys Lys Asn Val Ser Leu Ser Phe Asn Asn Thr Asp Glu
         35                  40                  45

Val Val Ala Lys Lys Asn Gly Thr Val Val Phe Gly Ala Ala Thr Tyr
     50                  55                  60

Leu Pro Pro Tyr Gly Lys Val Ser Gly Phe Asp Asp Lys Arg Leu Lys
 65                  70                  75                  80

Glu Arg Gly Asn Ala Val Asn Trp Ile His Thr Thr Pro Gly Leu
                 85                  90                  95

Val Gly Tyr Ser Tyr Glu Asp Val Thr Cys Asn Ser Gly Asn Cys Pro
            100                 105                 110

Glu Val Ser Tyr Lys Thr Gln Phe Ile Phe Asp Asn His Gln Leu Ala
        115                 120                 125

Lys Lys Lys Thr Asp Ser Lys Leu Asp Ile Tyr Glu Asp Lys Ser Arg
    130                 135                 140

Asp Asn Ser Pro Ile Tyr Lys Leu Gln Asp Tyr Pro Trp Leu Gly Val
145                 150                 155                 160

Ser Phe Asn Leu Gly Gly Glu Ser Ser Phe Lys Pro Lys Arg Gln Gly
                165                 170                 175

Ser Leu Val Ser Ser Phe Ser Glu Asp Val Thr Gln Gln Asn Gly Thr
            180                 185                 190

Gln Asp Gln Tyr Lys Gly Lys Asn Leu Val Tyr Thr Thr Glu Asp Tyr
        195                 200                 205

Asn Asn Gln Gly Asn Arg Asn His Gln Asp Lys His His Ala Ile Ala
    210                 215                 220

Phe Tyr Leu Asn Ala Lys Leu His Leu Asp Lys Lys Gly Ile Lys
225                 230                 235                 240

Asp Ile Thr Asp Lys Thr Val Gln Leu Gly Val Leu Lys Pro Arg Ile
                245                 250                 255

Asp Leu Thr Glu Ala Trp Lys Asn Arg His Gly Ser Phe Phe Gly Asn
            260                 265                 270

Gly Asn Trp Thr Phe Glu Asp Lys Gly Ala Val Ser Val Lys Leu Ile
        275                 280                 285

Leu Pro Glu Val Lys Ala Gly Arg Cys Ile Asn Lys Pro Asn Pro Asn
    290                 295                 300

Pro Lys Ala Gln Ala Leu Ser Pro Ala Leu Thr Ala Pro Ala Leu Trp
305                 310                 315                 320

Phe Gly Pro Val Gln Asn Gly Lys Met Glu Met Tyr Ser Ala Ser Val
                325                 330                 335
```

| | | | | | | | | | | | |
|---|---|---|---|---|---|---|---|---|---|---|---|
|Ser|Thr|Tyr|Pro|Asp|Ser|Ser|Ser|Arg|Ile|Phe|Leu|Gln|Asn|Leu|
| | | |340| | | |345| | | |350| | | |

Ser Thr Tyr Pro Asp Ser Ser Ser Arg Ile Phe Leu Gln Asn Leu
                340                 345                 350

Lys Arg Lys Asn Asp Pro Asn Lys Pro Gly Arg Tyr Ser Leu Ala Asp
            355                 360                 365

Leu Ser Ala Ser Glu Ile Lys Ser Lys Glu Pro Thr Phe Thr Gly Arg
370                 375                 380

Gln Thr Val Ile Arg Leu Asp Lys Gly Val His Gln Ile Lys Leu Lys
385                 390                 395                 400

Gly Asn Glu Val Glu Gly Phe Lys Gly Asn Asn Gly Asn Asp Thr Phe
                405                 410                 415

Gly Ile Val Ser Glu Gly Ser Phe Met Pro Asp Ser Glu Trp Lys
                420                 425                 430

Lys Val Leu Leu Pro Trp Thr Val Arg Ala Phe Asn Asp Asp Gly Gln
            435                 440                 445

Phe Asn Thr Val Asn Lys Glu Glu Asn Gly Lys Pro Lys Tyr Ser
        450                 455                 460

Gln Lys Tyr Arg Ser Arg Asn Asn Gly Lys His Glu Arg Asn Leu Gly
465                 470                 475                 480

Asp Ile Val Asn Ser Pro Ile Val Ala Val Gly Glu Tyr Leu Ala Thr
                485                 490                 495

Ser Ala Asn Asp Gly Met Val His Ile Phe Lys Lys Ser Gly Gly Asp
                500                 505                 510

Asp Arg Asn Tyr Ser Leu Lys Leu Ser Tyr Ile Pro Gly Thr Met Pro
            515                 520                 525

Arg Lys Asp Ile Gln Ser Gln Asp Ser Thr Leu Ala Lys Glu Leu Arg
            530                 535                 540

Ala Phe Ala Glu Lys Ser Tyr Val Gly Asp Arg Tyr Gly Val Asp Gly
545                 550                 555                 560

Gly Phe Val Leu Arg Gln Val Glu Trp Lys Gly Gln Asn Arg Val Phe
                565                 570                 575

Met Phe Gly Ala Met Xaa Xaa Thr His Leu Ile Asn
                580                 585

<210> SEQ ID NO 3
<211> LENGTH: 963
<212> TYPE: DNA
<213> ORGANISM: Neisseria meningitidis

<400> SEQUENCE: 3

```
atgcaagcac ggctgctgat acctattctt ttttcagttt ttattttatc cgcctgcggg    60
acactgacag gtattccatc gcatggcgga ggtaaacgct tgcggtcga acaagaactt   120
gtggccgctt ctgccagagc tgccgttaaa gacatggatt acaggcatt acacggacga   180
aaagttgcat tgtacattgc aactatgggc gaccaaggtt caggcagttt gacaggggt   240
cgctactcca ttgatgcact gattcgtggc aatacataa acagccctgc cgtccgtacc   300
gattacacct atccacgtta cgaaaccacc gctgaaacaa catcaggcgg tttgacaggt   360
ttaaccactt ctttatctac acttaatgcc cctgcactct cgcgcaccca atcagacggt   420
agcggaagta aaagcagtct gggcttaaat attggcggga tggggattta tcgaaatgaa   480
accttgacga ctaacccgcg cgacactgcc tttctttccc acttggtaca gaccgtattt   540
ttcctgcgcg gcatagacgt tgtttctcct gccaatgccg atacggatgt gtttattaac   600
atcgacgtat tcggaacgat acgcaacaga accgaaatgc acctatacaa tgccgaaaca   660
ctgaaagccc aaacaaaact ggaatatttc gcagtagaca gaaccaataa aaaattgctc   720
```

-continued

```
atcaaaccaa aaaccaatgc gtttgaagct gcctataaag aaaattacgc attgtggatg    780
ggaccgtata aagtaagcaa aggaattaaa ccgacagaag gattaatggt cgatttctcc    840
gatatccaac catacggcaa tcatatgggt aactctgccc catccgtaga ggctgataac    900
agtcatgagg gtatggata cagcgatgaa gcagtgcgac gacatagaca agggcaacct    960
tga                                                                  963
```

<210> SEQ ID NO 4
<211> LENGTH: 320
<212> TYPE: PRT
<213> ORGANISM: Neisseria meningitidis

<400> SEQUENCE: 4

```
Met Gln Ala Arg Leu Leu Ile Pro Ile Leu Phe Ser Val Phe Ile Leu
 1               5                   10                  15

Ser Ala Cys Gly Thr Leu Thr Gly Ile Pro Ser His Gly Gly Gly Lys
             20                  25                  30

Arg Phe Ala Val Glu Gln Glu Leu Val Ala Ala Ser Ala Arg Ala Ala
         35                  40                  45

Val Lys Asp Met Asp Leu Gln Ala Leu His Gly Arg Lys Val Ala Leu
     50                  55                  60

Tyr Ile Ala Thr Met Gly Asp Gln Gly Ser Gly Ser Leu Thr Gly Gly
 65                  70                  75                  80

Arg Tyr Ser Ile Asp Ala Leu Ile Arg Gly Glu Tyr Ile Asn Ser Pro
                 85                  90                  95

Ala Val Arg Thr Asp Tyr Thr Tyr Pro Arg Tyr Glu Thr Thr Ala Glu
            100                 105                 110

Thr Thr Ser Gly Gly Leu Thr Gly Leu Thr Thr Ser Leu Ser Thr Leu
        115                 120                 125

Asn Ala Pro Ala Leu Ser Arg Thr Gln Ser Asp Gly Ser Gly Ser Lys
    130                 135                 140

Ser Ser Leu Gly Leu Asn Ile Gly Gly Met Gly Asp Tyr Arg Asn Glu
145                 150                 155                 160

Thr Leu Thr Thr Asn Pro Arg Asp Thr Ala Phe Leu Ser His Leu Val
                165                 170                 175

Gln Thr Val Phe Phe Leu Arg Gly Ile Asp Val Val Ser Pro Ala Asn
            180                 185                 190

Ala Asp Thr Asp Val Phe Ile Asn Ile Asp Val Phe Gly Thr Ile Arg
        195                 200                 205

Asn Arg Thr Glu Met His Leu Tyr Asn Ala Glu Thr Leu Lys Ala Gln
    210                 215                 220

Thr Lys Leu Glu Tyr Phe Ala Val Asp Arg Thr Asn Lys Lys Leu Leu
225                 230                 235                 240

Ile Lys Pro Lys Thr Asn Ala Phe Glu Ala Ala Tyr Lys Glu Asn Tyr
                245                 250                 255

Ala Leu Trp Met Gly Pro Tyr Lys Val Ser Lys Gly Ile Lys Pro Thr
            260                 265                 270

Glu Gly Leu Met Val Asp Phe Ser Asp Ile Gln Pro Tyr Gly Asn His
        275                 280                 285

Met Gly Asn Ser Ala Pro Ser Val Glu Ala Asp Asn Ser His Glu Gly
    290                 295                 300

Tyr Gly Tyr Ser Asp Glu Ala Val Arg Arg His Arg Gln Gly Gln Pro
305                 310                 315                 320
```

<210> SEQ ID NO 5

<211> LENGTH: 1164
<212> TYPE: DNA
<213> ORGANISM: Neisseria meningitidis

<400> SEQUENCE: 5

```
gtgcatatta actttcaat ggaatataaa gaatttaatg aaaattattt atataaaaag      60
ccgtttattt ttaaaaaagc tttagacgta agttctatct catggaaaga aattaatgag    120
ttgtatcaac gtgcagaccc tactgattgg caatttaaat ttcgcaaagg ggaaataatc    180
cccaaagaag cctatgttga atcattcaat gatgtgggta gaatacgtca tcggtttaat    240
aaaacagccg tatatcagta tctgcaagat ggtgcaacaa tggtttataa ccgtattgat    300
aatgagccat tgttgacag tattgctaaa caaattgccc agtttgctca agcacaaact    360
gttgttagtg ttatttggc gtttggtagt tctccatcat atcgtaatca ttgggatact    420
cgtgatgtgt ttgcggttca attgattggc aaaaaacact ggacagtttc tgctccaaat    480
tttgatatgc cattgtatat gcagcaagca aaagatatgc cgcacattac tccgcctaca    540
acagtagata tggaagtcat tttagaagca ggagatattt tatatatccc gcgtggttgg    600
tggcataatc ctatgcctat gaattgtgaa acattccatt tagctattgg aactttccg    660
ccaaatggtt ataattatat ggaatggttg atgaaaaaaa tacctgatat ccagagtatt    720
cgtcaaaatt tcatagactg ggaacacgac caaaaaaata tagataatgc ggctcaggca    780
gttactgaaa tgatgaagaa ccaagaaaat tatcaagcat tcatacaaga ttttttggga    840
aatcaacgcg taaatactgc atttaatatg caaattttg gaaatctgga taatgacaga    900
ttacctgaaa atagtacaat taaactcaat tcgttggata ccgtacaat taaacaagga    960
tatatcatag cgaatggcat caaaaccaac ttggacaatg atagccaaac gattttgcaa   1020
tggattgctg acaaacatag tgttaagtta actcaactgt atgaattttg ccaaaatcaa   1080
aacattaatt tggaaaaagt ggaaaaatta gtgtttgatt tgacaatgat cgatgtattg   1140
gaatgtttaa ctgatgaaag ataa                                          1164
```

<210> SEQ ID NO 6
<211> LENGTH: 387
<212> TYPE: PRT
<213> ORGANISM: Neisseria meningitidis

<400> SEQUENCE: 6

```
Met His Ile Asn Phe Ser Met Glu Tyr Lys Glu Phe Asn Glu Asn Tyr
  1               5                  10                  15

Leu Tyr Lys Lys Pro Phe Ile Phe Lys Lys Ala Leu Asp Val Ser Ser
             20                  25                  30

Ile Ser Trp Lys Glu Ile Asn Glu Leu Tyr Gln Arg Ala Asp Pro Thr
         35                  40                  45

Asp Trp Gln Phe Lys Phe Arg Lys Gly Glu Ile Ile Pro Lys Glu Ala
     50                  55                  60

Tyr Val Glu Ser Phe Asn Asp Val Gly Arg Ile Arg His Arg Phe Asn
 65                  70                  75                  80

Lys Thr Ala Val Tyr Gln Tyr Leu Gln Asp Gly Ala Thr Met Val Tyr
                 85                  90                  95

Asn Arg Ile Asp Asn Glu Pro Phe Val Asp Ser Ile Ala Lys Gln Ile
            100                 105                 110

Ala Gln Phe Ala Gln Ala Gln Thr Val Val Ser Gly Tyr Leu Ala Phe
        115                 120                 125

Gly Ser Ser Pro Ser Tyr Arg Asn His Trp Asp Thr Arg Asp Val Phe
    130                 135                 140
```

Ala Val Gln Leu Ile Gly Lys Lys His Trp Thr Val Ser Ala Pro Asn
145                 150                 155                 160

Phe Asp Met Pro Leu Tyr Met Gln Ala Lys Asp Met Pro His Ile
            165                 170                 175

Thr Pro Pro Thr Thr Val Asp Met Glu Val Ile Leu Glu Ala Gly Asp
            180                 185                 190

Ile Leu Tyr Ile Pro Arg Gly Trp Trp His Asn Pro Met Pro Met Asn
        195                 200                 205

Cys Glu Thr Phe His Leu Ala Ile Gly Thr Phe Pro Pro Asn Gly Tyr
210                 215                 220

Asn Tyr Met Glu Trp Leu Met Lys Lys Ile Pro Asp Ile Gln Ser Ile
225                 230                 235                 240

Arg Gln Asn Phe Ile Asp Trp Glu His Asp Gln Lys Asn Ile Asp Asn
                245                 250                 255

Ala Ala Gln Ala Val Thr Glu Met Met Lys Asn Gln Glu Asn Tyr Gln
            260                 265                 270

Ala Phe Ile Gln Asp Phe Leu Gly Asn Gln Arg Val Asn Thr Ala Phe
        275                 280                 285

Asn Met Gln Ile Phe Gly Asn Leu Asp Asn Asp Arg Leu Pro Glu Asn
290                 295                 300

Ser Thr Ile Lys Leu Asn Ser Leu Asp Asn Arg Thr Ile Lys Gln Gly
305                 310                 315                 320

Tyr Ile Ile Ala Asn Gly Ile Lys Thr Asn Leu Asp Asn Asp Ser Gln
                325                 330                 335

Thr Ile Leu Gln Trp Ile Ala Asp Lys His Ser Val Lys Leu Thr Gln
            340                 345                 350

Leu Tyr Glu Phe Cys Gln Asn Gln Asn Ile Asn Leu Glu Lys Val Glu
        355                 360                 365

Lys Leu Val Phe Asp Leu Thr Met Ile Asp Val Leu Glu Cys Leu Thr
370                 375                 380

Asp Glu Arg
385

<210> SEQ ID NO 7
<211> LENGTH: 1263
<212> TYPE: DNA
<213> ORGANISM: Neisseria meningitidis

<400> SEQUENCE: 7
atgacattat ttcgccccga agtattccaa gctaaaaaaa atcgctggac agggcaaatt      60
gttttagtgc gtccttttc cttgcagttt ttaacatttt tcgcggtctc attagcggct     120
attttagttg ctttttaat ttttgggagc tataccaata aaccaccgt aacaggacaa     180 cttttgccga caacaggggt agtacgcgta tattcgcagg atatggggt tattgctcat     240 caacacgtta tgaatggcga ttttgtgaaa aaaggcgatg tgttattac attatctact     300 tcacgaaatg acaataatgg cagcatacaa gcacgattac tcgccgaagc tgaattaaaa     360
aaatcactat cagaacaaga aattattatg aaaaaacgtg ttcatgcagc agaaaaaacc     420
gcacaagaaa acacggtaca ccgttttcag aaccaaatgc aacacgttag aaatcaaatt     480
atcatgcaag aaaaacgtat tgcgatttct gaaaaaatgt tagaaaaaca gcgttattta     540
gccaaaatgg acgcaatttc tgaattagaa aaaaatagtt atgaaattgc tttattggag     600
ctgaaagcag gttagccgc ttaccaacga gaagcagata tcttgctcg ggaaataact     660 gtacagcaaa gcaatctaaa aaatctgcct gaacagcaag ctactgaaat cagtcaatta     720

-continued

```
gaacgcgcag tatctgtcta tcaacaagaa atattggatt atcaacaacg taacgaacaa    780
actattcgcg caaccatatc aggctatgtc agttctatta acacggaaat tggtcagcag    840
gtagatacta acaaactatt gatgagtatc gtgccgaaag aaagtgaatt actggctaat    900
ttatatgtcc ctagtcgcgc aatcggtttt gtaaaaccaa atgacaaggt aattttgcgt    960
tatcaagcat atccttatca aaaattcgga cacgcagaag gacacgtcat ttctattgct    1020
caaacggcac taggggcgca agaatggaca aatttaggca atattttac tcaaacagca     1080 caagtgaatg agcctgttta tttaatcaaa gtaaaactgg ataatcagca tattcgtata    1140
tatggcacgg agaagaaatt gcaaattggt atgatactag aagccgatat tttgcatgag    1200
aataaacggt tatatgaatg gatacttgac cctttgtatc aagtaatggg aaaaatatca    1260
tag                                                                  1263
```

<210> SEQ ID NO 8
<211> LENGTH: 420
<212> TYPE: PRT
<213> ORGANISM: Neisseria meningitidis

<400> SEQUENCE: 8

```
Met Thr Leu Phe Arg Pro Glu Val Phe Gln Ala Lys Lys Asn Arg Trp
  1               5                  10                  15

Thr Gly Gln Ile Val Leu Val Arg Pro Phe Ser Leu Gln Phe Leu Thr
             20                  25                  30

Phe Phe Ala Val Ser Leu Ala Ala Ile Leu Val Ala Phe Leu Ile Phe
         35                  40                  45

Gly Ser Tyr Thr Asn Lys Thr Thr Val Thr Gly Gln Leu Leu Pro Thr
     50                  55                  60

Thr Gly Val Val Arg Val Tyr Ser Gln Asp Met Gly Val Ile Ala His
 65                  70                  75                  80

Gln His Val Met Asn Gly Asp Phe Val Lys Lys Gly Asp Val Leu Phe
                 85                  90                  95

Thr Leu Ser Thr Ser Arg Asn Asp Asn Asn Gly Ser Ile Gln Ala Arg
            100                 105                 110

Leu Leu Ala Glu Ala Glu Leu Lys Lys Ser Leu Ser Glu Gln Glu Ile
        115                 120                 125

Ile Met Lys Lys Arg Val His Ala Ala Glu Lys Thr Ala Gln Glu Asn
    130                 135                 140

Thr Val His Arg Phe Gln Asn Gln Met Gln His Val Arg Asn Gln Ile
145                 150                 155                 160

Ile Met Gln Glu Lys Arg Ile Ala Ile Ser Glu Lys Met Leu Glu Lys
                165                 170                 175

Gln Arg Tyr Leu Ala Lys Met Asp Ala Ile Ser Glu Leu Glu Lys Asn
            180                 185                 190

Ser Tyr Glu Ile Ala Leu Leu Glu Leu Lys Ala Gly Leu Ala Ala Tyr
        195                 200                 205

Gln Arg Glu Ala Asp Asn Leu Ala Arg Glu Ile Thr Val Gln Gln Ser
    210                 215                 220

Asn Leu Lys Asn Leu Pro Glu Gln Gln Ala Thr Glu Ile Ser Gln Leu
225                 230                 235                 240

Glu Arg Ala Val Ser Val Tyr Gln Gln Glu Ile Leu Asp Tyr Gln Gln
                245                 250                 255

Arg Asn Glu Gln Thr Ile Arg Ala Thr Ile Ser Gly Tyr Val Ser Ser
            260                 265                 270
```

```
Ile Asn Thr Glu Ile Gly Gln Gln Val Asp Thr Asn Lys Leu Leu Met
        275                 280                 285
Ser Ile Val Pro Lys Glu Ser Glu Leu Leu Ala Asn Leu Tyr Val Pro
        290                 295                 300
Ser Arg Ala Ile Gly Phe Val Lys Pro Asn Asp Lys Val Ile Leu Arg
305                 310                 315                 320
Tyr Gln Ala Tyr Pro Tyr Gln Lys Phe Gly His Ala Glu Gly His Val
                325                 330                 335
Ile Ser Ile Ala Gln Thr Ala Leu Gly Ala Gln Glu Trp Thr Asn Leu
            340                 345                 350
Gly Asn Ile Phe Thr Gln Thr Ala Gln Val Asn Glu Pro Val Tyr Leu
        355                 360                 365
Ile Lys Val Lys Leu Asp Asn Gln His Ile Arg Ile Tyr Gly Thr Glu
        370                 375                 380
Lys Lys Leu Gln Ile Gly Met Ile Leu Glu Ala Asp Ile Leu His Glu
385                 390                 395                 400
Asn Lys Arg Leu Tyr Glu Trp Ile Leu Asp Pro Leu Tyr Gln Val Met
                405                 410                 415
Gly Lys Ile Ser
            420

<210> SEQ ID NO 9
<211> LENGTH: 2013
<212> TYPE: DNA
<213> ORGANISM: Neisseria meningitidis

<400> SEQUENCE: 9
ttggcgtgtt tggtatcggt attggggttt catggttttt atacggattt gcgccattta      60
agggcgcgtt tttctttgtc tcttaaaggc gcaacattgg cagatttggt acggtttgct     120
aatagcatga atttaactgc tcgagctgtt cggttggatt tagatgaatt ggtaaatttg     180
cgcttaccct gtattttaca ttgggattta atcattttg tggtgttgca tgaagttcat      240
cgtaatcaca ttgtgattat gaaccctgct tcgggttggc aaaaagtgcg tatggaagaa     300
gtctcgcgct gttttacagg catagcgttg gagctattcc ctaacacgca atttgaagag     360
aaacacgaaa cgcgtaaaat cgcatacta ccgatgttgc gcggtgtggt tggattaaaa      420
aggtctttat ttcagcttct gctgctggcg gcagtattac aggtgtttgc tttggcaagc     480
cctttttta tgcaatgggt aatagatcat gccattgtat cggcagaccg tgatttattg      540
ctaacattgg cattgggttt tggtttgttg atgattgtgc agcagttggt gtcattgttg     600
caaacttggg caggtatgta tttgtctact tcattgaata tccaatggaa agccaacgta     660
ttccgccgct taatggattt acctgttct tatttcacta aacgacactt gggcgatgtg      720
gtttcacgtt ttggctcggt ggatagtatt caaagtacgc tcacttctac tttctttgtg     780
ctggtactca acagcattat ggcagtattt acattagggt taatgtattt atacagccct     840
agtttaacgg ctgttgtatt ggttgtttta ctgatttata tcggtattcg ttgggtggca     900
tattatccgt tacgccatgc aaccgaagaa atattgttc atgctgccaa gcaaagcagt      960
tatttcatgg aaaccatacg cggtattcaa accgttaaat tatttgataa aaatgcacaa    1020
cgtcatgcgg cttggctgaa cttatttgtt gatacaatca acacaggttt aacgacacaa    1080
aaactttccg caatgttcgg ttttgcgaac agcctttgt ttggtatcgc taatatttta    1140
attgtgtatt ttggtgcggt ttctgtgttg gacggtgttt ttaccgttgg ggcgttaatg    1200
gcgtttatgt cctacaaaag tcagtttgag agtaaagcag gttcattgat tgaccagttt    1260
```

```
gtacaaatca aaatgctagg attgcacgcg gaacgcttgg cggatattgt gctagaaaaa   1320
acggaaaacg agcagaacaa cgatttcagg ctgcctaaaa atttagaaca ctttgatatt   1380
aaaatagaaa atatatcatt tcgctatgct gaaaatgaac catacatttt gcaagatttc   1440
agtttaatta tcaaacaagg aacagccatt gcttttgctg acattcagg ctgtgggaaa   1500 tctacgctca ttcaaattct gacaggcagt ctgaaacctg aaagcggtca cgtgttacta   1560
ggcgagaatg atattcatgc gtttccacct gcatttatcc gcaaatggag cgcaagtgta   1620
atgcaagatg atgtgttatt tgctggctca atcgcagaaa acatcagttt ttttgatgat   1680
acgcccaata tggaaaaaat cgcattttgc gctcaaatgg cgaatattca tcatgaaatt   1740
gtcgctatgc ctatggcgta tgaaaccta attggtgaca tgggaagcgc attgagcggt   1800
gggcaaaagc agcgtattgt tctagctcgt gctttatatc gtgaacccaa aattttgttt   1860
ttagacgaag ccagtagcca tttggacatc aacaatgaac gtgtgattaa cgataatcta   1920
cgccaactca acattaccaa aatcatggtc gcgcatcgtc aggaaacttt aaatactgct   1980
gatagcgtag tttatttaga caaggtagcc tga                                2013

<210> SEQ ID NO 10
<211> LENGTH: 670
<212> TYPE: PRT
<213> ORGANISM: Neisseria meningitidis

<400> SEQUENCE: 10

Met Ala Cys Leu Val Ser Val Leu Gly Phe His Gly Phe Tyr Thr Asp
 1               5                  10                  15

Leu Arg His Leu Arg Ala Arg Phe Ser Leu Ser Leu Lys Gly Ala Thr
            20                  25                  30

Leu Ala Asp Leu Val Arg Phe Ala Asn Ser Met Asn Leu Thr Ala Arg
        35                  40                  45

Ala Val Arg Leu Asp Leu Asp Glu Leu Val Asn Leu Arg Leu Pro Cys
    50                  55                  60

Ile Leu His Trp Asp Leu Asn His Phe Val Leu His Glu Val His
65                  70                  75                  80

Arg Asn His Ile Val Ile Met Asn Pro Ala Ser Gly Trp Gln Lys Val
                85                  90                  95

Arg Met Glu Glu Val Ser Arg Cys Phe Thr Gly Ile Ala Leu Glu Leu
            100                 105                 110

Phe Pro Asn Thr Gln Phe Glu Glu Lys His Glu Thr Arg Lys Ile Arg
        115                 120                 125

Ile Leu Pro Met Leu Arg Gly Val Gly Leu Lys Arg Ser Leu Phe
    130                 135                 140

Gln Leu Leu Leu Ala Ala Val Leu Gln Val Phe Ala Leu Ala Ser
145                 150                 155                 160

Pro Phe Phe Met Gln Trp Val Ile Asp His Ala Ile Val Ser Ala Asp
                165                 170                 175

Arg Asp Leu Leu Leu Thr Leu Ala Leu Gly Phe Gly Leu Leu Met Ile
            180                 185                 190

Val Gln Gln Leu Val Ser Leu Leu Gln Thr Trp Ala Gly Met Tyr Leu
        195                 200                 205

Ser Thr Ser Leu Asn Ile Gln Trp Lys Ala Asn Val Phe Arg Arg Leu
    210                 215                 220

Met Asp Leu Pro Val Ser Tyr Phe Thr Lys Arg His Leu Gly Asp Val
225                 230                 235                 240

Val Ser Arg Phe Gly Ser Val Asp Ser Ile Gln Ser Thr Leu Thr Ser
```

-continued

```
                    245                 250                 255
Thr Phe Phe Val Leu Val Leu Asn Ser Ile Met Ala Val Phe Thr Leu
                260                 265                 270
Gly Leu Met Tyr Leu Tyr Ser Pro Ser Leu Thr Ala Val Val Leu Val
            275                 280                 285
Val Leu Leu Ile Tyr Ile Gly Ile Arg Trp Val Ala Tyr Tyr Pro Leu
        290                 295                 300
Arg His Ala Thr Glu Glu Asn Ile Val His Ala Ala Lys Gln Ser Ser
305                 310                 315                 320
Tyr Phe Met Glu Thr Ile Arg Gly Ile Gln Thr Val Lys Leu Phe Asp
                325                 330                 335
Lys Asn Ala Gln Arg His Ala Ala Trp Leu Asn Leu Phe Val Asp Thr
                340                 345                 350
Ile Asn Thr Gly Leu Thr Thr Gln Lys Leu Ser Ala Met Phe Gly Phe
                355                 360                 365
Ala Asn Ser Leu Leu Phe Gly Ile Ala Asn Ile Leu Ile Val Tyr Phe
            370                 375                 380
Gly Ala Val Ser Val Leu Asp Gly Val Phe Thr Val Gly Ala Leu Met
385                 390                 395                 400
Ala Phe Met Ser Tyr Lys Ser Gln Phe Glu Ser Lys Ala Gly Ser Leu
                405                 410                 415
Ile Asp Gln Phe Val Gln Ile Lys Met Leu Gly Leu His Ala Glu Arg
                420                 425                 430
Leu Ala Asp Ile Val Leu Glu Lys Thr Glu Asn Glu Gln Asn Asn Asp
                435                 440                 445
Phe Arg Leu Pro Lys Asn Leu Glu His Phe Asp Ile Lys Ile Glu Asn
            450                 455                 460
Ile Ser Phe Arg Tyr Ala Glu Asn Glu Pro Tyr Ile Leu Gln Asp Phe
465                 470                 475                 480
Ser Leu Ile Ile Lys Gln Gly Thr Ala Ile Ala Phe Ala Gly His Ser
                485                 490                 495
Gly Cys Gly Lys Ser Thr Leu Ile Gln Ile Leu Thr Gly Ser Leu Lys
                500                 505                 510
Pro Glu Ser Gly His Val Leu Leu Gly Glu Asn Asp Ile His Ala Phe
            515                 520                 525
Pro Pro Ala Phe Ile Arg Lys Trp Ser Ala Ser Val Met Gln Asp Asp
            530                 535                 540
Val Leu Phe Ala Gly Ser Ile Ala Glu Asn Ile Ser Phe Phe Asp Asp
545                 550                 555                 560
Thr Pro Asn Met Glu Lys Ile Ala Phe Cys Ala Gln Met Ala Asn Ile
                565                 570                 575
His His Glu Ile Val Ala Met Pro Met Ala Tyr Glu Thr Leu Ile Gly
                580                 585                 590
Asp Met Gly Ser Ala Leu Ser Gly Gly Gln Lys Gln Arg Ile Val Leu
            595                 600                 605
Ala Arg Ala Leu Tyr Arg Glu Pro Lys Ile Leu Phe Leu Asp Glu Ala
        610                 615                 620
Ser Ser His Leu Asp Ile Asn Asn Glu Arg Val Ile Asn Asp Asn Leu
625                 630                 635                 640
Arg Gln Leu Asn Ile Thr Lys Ile Met Val Ala His Arg Gln Glu Thr
                645                 650                 655
Leu Asn Thr Ala Asp Ser Val Val Tyr Leu Asp Lys Val Ala
                660                 665                 670
```

```
<210> SEQ ID NO 11
<211> LENGTH: 996
<212> TYPE: DNA
<213> ORGANISM: Neisseria meningitidis
<220> FEATURE:
<221> NAME/KEY: misc_feature
<222> LOCATION: 981, 982, 983, 984, 985
<223> OTHER INFORMATION: n = A,T,C or G

<400> SEQUENCE: 11
atgaaaatca aagccctgat gattgccgcc gcattgctgg cagcagccga tgtccacgcc     60
gcaccgcaaa aggcaaaaac cgcatccgcc aaagctgcca agctgccaa agctgccaaa    120
gctgccaaag ctgccaaagt tgccaaagtt gccaaagttg ccaaagttgc caaagttgcc    180
aaagttgcca agttgccaa agttgccaaa gttgccaaag ttgccaaagt tgccaaagtt    240
gccaaagttg ccaaagttgc caaagttgcc gccacggcgc aaaaagaagc cgcacccgca    300
caacagcagg gcggtatccg cttttcagac ggcattgccg ccgttgccga caacgaagtc    360
atcacgcgcc gccggcttgc cgaagccgtt gccgaagcca agccaacct gcccaaagac    420
gcgcagataa gcgaatccga gctgtcccga caggtgctga tgcagcttgt caaccaatcc    480
ctgattgtac aggcgggcaa acgccgcaac attcaagcaa gcgaagcgga aatcgatgcc    540
gtcgtcgcaa aaaatcccgc cctcaaaaac ctcagccccg cccaacgccg cgattttgcc    600
gacaacatca ttgccgaaaa agtccgccag caggcagtga tgcagaacag ccgagtgagc    660
gaagctgaaa tcgatgcctt cctcgagcag gcgcaaaaac aaggcatcac cctgcccgaa    720
ggcgcaccgt tgcgccaata ccgcgcccaa cacatcctga ttaaagccga cagcgaaaac    780
gccgccgtcg gcgcggaaag caccatccgc aaaatctacg gagaggcccg cagcggcaca    840
gacttttcca gcctagcgcg ccaatattcg caagacgcga gcgcgggcaa cggcggagat    900
ttgggctggt ttgccgacgg cgtgatggtt cccgcctttg aagaagccgt ccacgcgctc    960
aaacccggac aggtcggcgc nnnnncacac acttaa                              996

<210> SEQ ID NO 12
<211> LENGTH: 331
<212> TYPE: PRT
<213> ORGANISM: Neisseria meningitidis
<220> FEATURE:
<221> NAME/KEY: VARIANT
<222> LOCATION: 328, 329
<223> OTHER INFORMATION: Xaa = Any Amino Acid

<400> SEQUENCE: 12

Met Lys Ile Lys Ala Leu Met Ile Ala Ala Ala Leu Leu Ala Ala
  1               5                  10                  15

Asp Val His Ala Ala Pro Gln Lys Ala Lys Thr Ala Ser Ala Lys Ala
                 20                  25                  30

Ala Lys Ala Ala Lys Ala Ala Lys Ala Ala Lys Ala Ala Lys Val Ala
         35                  40                  45

Lys Val Ala Lys Val Ala Lys Val Ala Lys Val Ala Lys Val Ala Lys
         50                  55                  60

Val Ala Lys Val Ala Lys Val Ala Lys Val Ala Lys Val Ala Lys Val
 65                  70                  75                  80

Ala Lys Val Ala Lys Val Ala Lys Val Ala Ala Thr Ala Gln Lys Glu
                 85                  90                  95

Ala Ala Pro Ala Gln Gln Gln Gly Gly Ile Arg Phe Ser Asp Gly Ile
            100                 105                 110

Ala Ala Val Ala Asp Asn Glu Val Ile Thr Arg Arg Arg Leu Ala Glu
```

```
                    115                 120                 125
Ala Val Ala Glu Ala Lys Ala Asn Leu Pro Lys Asp Ala Gln Ile Ser
        130                 135                 140

Glu Ser Glu Leu Ser Arg Gln Val Leu Met Gln Leu Val Asn Gln Ser
145                 150                 155                 160

Leu Ile Val Gln Ala Gly Lys Arg Arg Asn Ile Gln Ala Ser Glu Ala
                165                 170                 175

Glu Ile Asp Ala Val Ala Lys Asn Pro Ala Leu Lys Asn Leu Ser
            180                 185                 190

Pro Ala Gln Arg Arg Asp Phe Ala Asp Asn Ile Ile Ala Glu Lys Val
                195                 200                 205

Arg Gln Gln Ala Val Met Gln Asn Ser Arg Val Ser Glu Ala Glu Ile
            210                 215                 220

Asp Ala Phe Leu Glu Gln Ala Gln Lys Gln Gly Ile Thr Leu Pro Glu
225                 230                 235                 240

Gly Ala Pro Leu Arg Gln Tyr Arg Ala Gln His Ile Leu Ile Lys Ala
                245                 250                 255

Asp Ser Glu Asn Ala Ala Val Gly Ala Glu Ser Thr Ile Arg Lys Ile
            260                 265                 270

Tyr Gly Glu Ala Arg Ser Gly Thr Asp Phe Ser Ser Leu Ala Arg Gln
275                 280                 285

Tyr Ser Gln Asp Ala Ser Ala Gly Asn Gly Gly Asp Leu Gly Trp Phe
            290                 295                 300

Ala Asp Gly Val Met Val Pro Ala Phe Glu Glu Ala Val His Ala Leu
305                 310                 315                 320

Lys Pro Gly Gln Val Gly Ala Xaa Xaa His Thr
                325                 330

<210> SEQ ID NO 13
<211> LENGTH: 630
<212> TYPE: DNA
<213> ORGANISM: Neisseria meningitidis

<400> SEQUENCE: 13
ttggtcaaaa cggcagacgg ctacaaagct attgcccgta tccgagccgg cgagagcgtc      60
ctctccaagg acgaggcaag cggaaaaatg ggatacaaac ccgttaccgc ccgatacggc     120
aatccgtatg aagaaaccgt ttacattaaa gtttcagacg gcatcggcaa cagccaaacc     180
ctgatttcca accgcatcca ctcgttttat tcgggcggca atggattaa  acggaagat      240 ttgaaagcgg gaatcaggct gttatccgaa agcggcaaaa cccaaaccgt ccgcaacatc     300
gttgtcaaac caaaaccgct caaagcctac aatctgaccg ttgctgactg gcatacctac     360
ttcgtcaagg gcagtcaggc ggaaacggaa ggggtttggg ttcataatgc gtgtccgcct     420
aaaagaacag gaagctccaa gaatgaaaaa catggagatg gcggtcgaag tcaaatatca     480
gcagaatcac gaattgctga attaaaaaat aaaattattc ccggaatgca caaaaatgaa     540
cgattaaaga ttgagaaaac aatcagaaat attgcaaaaa atgccaatcg aaaagcaaaa     600
ggagaagagc atggtcgaca cggtcgttaa                                     630

<210> SEQ ID NO 14
<211> LENGTH: 209
<212> TYPE: PRT
<213> ORGANISM: Neisseria meningitidis

<400> SEQUENCE: 14

Met Val Lys Thr Ala Asp Gly Tyr Lys Ala Ile Ala Arg Ile Arg Ala
```

```
                1               5               10              15
Gly Glu Ser Val Leu Ser Lys Asp Glu Ala Ser Gly Lys Met Gly Tyr
                        20                  25                  30

Lys Pro Val Thr Ala Arg Tyr Gly Asn Pro Tyr Glu Glu Thr Val Tyr
                35                  40                  45

Ile Lys Val Ser Asp Gly Ile Gly Asn Ser Gln Thr Leu Ile Ser Asn
        50                  55                  60

Arg Ile His Ser Phe Tyr Ser Gly Gly Lys Trp Ile Lys Thr Glu Asp
65                  70                  75                  80

Leu Lys Ala Gly Ile Arg Leu Leu Ser Glu Ser Gly Lys Thr Gln Thr
                85                  90                  95

Val Arg Asn Ile Val Val Lys Pro Lys Pro Leu Lys Ala Tyr Asn Leu
                100                 105                 110

Thr Val Ala Asp Trp His Thr Tyr Phe Val Lys Gly Ser Gln Ala Glu
                115                 120                 125

Thr Glu Gly Val Trp Val His Asn Ala Cys Pro Pro Lys Arg Thr Gly
                130                 135                 140

Ser Ser Lys Asn Glu Lys His Gly Asp Gly Gly Arg Ser Gln Ile Ser
145                 150                 155                 160

Ala Glu Ser Arg Ile Ala Glu Leu Lys Asn Lys Ile Ile Pro Gly Met
                165                 170                 175

His Lys Asn Glu Arg Leu Lys Ile Glu Lys Thr Ile Arg Asn Ile Ala
                180                 185                 190

Lys Asn Ala Asn Arg Lys Ala Lys Gly Glu Glu His Gly Arg His Gly
                195                 200                 205

Arg
```

<210> SEQ ID NO 15
<211> LENGTH: 798
<212> TYPE: DNA
<213> ORGANISM: Neisseria meningitidis

<400> SEQUENCE: 15

```
atgaatccag cccccaaaaa accttctctt ctcttctctt ctcttctctt ctcttctctt    60
ctcttctctt ccgcagcgca ggcggcaagt gaagacagca gccgcagccc gtattatgtg   120
caggcggatt tagcctatgc cgccgaacgc attacccaca attatccgga accaaccggt   180
gcagacaaag acaaaataag cacagtaagc gattatttca gaaacatccg tgcgcattcc   240
atccaccctc gggtgtcggt cggctacgac ttcggcgact ggagaatagc ggcagattat   300
gccagttaca gaaatggaa agaaagtaat tcttctacta atgcagaaaa tagagataat   360
gcaaaaaact acgtaaagat tgaaacaaaa catcaaggaa acggcagctt ccacgccgct   420
tcttctctcg gcttatccgc catttacgat ttcaaactca cgataaaatt caaaccctat   480
atcggcgcgc gcgtcgccta cggacacgtt aaacatcagg ttcattcagt ggaaacaaaa   540
accacgactg ttacctctaa accgacggca acctctccac agggaggccc tattatacaa   600
actgatccca gcaaacctcc ctatcacgaa agcacagca tcagcagctt gggtcttggt   660
gtcatcgccg tgtcggtttt cgacatcacg cccaagctga ccttggacac cggataccgc   720
taccacaact ggggacgctt ggaaaacacc cgcttcaaaa cccacgaagt ctcattgggc   780
atgcgctacc acttctga                                                 798
```

<210> SEQ ID NO 16
<211> LENGTH: 265
<212> TYPE: PRT

<213> ORGANISM: Neisseria meningitidis

<400> SEQUENCE: 16

Met Asn Pro Ala Pro Lys Lys Pro Ser Leu Leu Phe Ser Ser Leu Leu
1 5 10 15

Phe Ser Ser Leu Leu Phe Ser Ser Ala Ala Gln Ala Ala Ser Glu Asp
20 25 30

Ser Ser Arg Ser Pro Tyr Tyr Val Gln Ala Asp Leu Ala Tyr Ala Ala
35 40 45

Glu Arg Ile Thr His Asn Tyr Pro Glu Pro Thr Gly Ala Asp Lys Asp
50 55 60

Lys Ile Ser Thr Val Ser Asp Tyr Phe Arg Asn Ile Arg Ala His Ser
65 70 75 80

Ile His Pro Arg Val Ser Val Gly Tyr Asp Phe Gly Asp Trp Arg Ile
85 90 95

Ala Ala Asp Tyr Ala Ser Tyr Arg Lys Trp Lys Glu Ser Asn Ser Ser
100 105 110

Thr Asn Ala Glu Asn Arg Asp Asn Ala Lys Asn Tyr Val Lys Ile Glu
115 120 125

Thr Lys His Gln Gly Asn Gly Ser Phe His Ala Ala Ser Ser Leu Gly
130 135 140

Leu Ser Ala Ile Tyr Asp Phe Lys Leu Asn Asp Lys Phe Lys Pro Tyr
145 150 155 160

Ile Gly Ala Arg Val Ala Tyr Gly His Val Lys His Gln Val His Ser
165 170 175

Val Glu Thr Lys Thr Thr Thr Val Thr Ser Lys Pro Thr Ala Thr Ser
180 185 190

Pro Gln Gly Gly Pro Ile Ile Gln Thr Asp Pro Ser Lys Pro Pro Tyr
195 200 205

His Glu Ser His Ser Ile Ser Ser Leu Gly Leu Gly Val Ile Ala Gly
210 215 220

Val Gly Phe Asp Ile Thr Pro Lys Leu Thr Leu Asp Thr Gly Tyr Arg
225 230 235 240

Tyr His Asn Trp Gly Arg Leu Glu Asn Thr Arg Phe Lys Thr His Glu
245 250 255

Val Ser Leu Gly Met Arg Tyr His Phe
260 265

<210> SEQ ID NO 17
<211> LENGTH: 2043
<212> TYPE: DNA
<213> ORGANISM: Neisseria meningitidis

<400> SEQUENCE: 17
atggtgctgc ctgtgttttt gttgagtgct tgtttgggcg gcggcggcag tttcgatctt 60
gattctgtcg ataccgaagc cccgcgtccc gcgccaaagt atcaagatgt ttcttccgaa 120
acaccgcaag cccaaaaaga ccaaggcgga tacggttttg caatgcgctt caagcggcgg 180
aattggcacc caaaaaataa agaagatcat aaggcattat cagaagcgga ttgggagaag 240
ttaggtgcgg gtaagccaga tgagtttccc caaaagaatg agatttcagc gatggataag 300
ggtacgctga acgaatccat cacgccgggc gacggcaaaa gccgtgctga aggctatacg 360
gatttccaat atgtccgctc gggctatatc taccgcaacg gtgtcaataa aatcgattac 420
caaaacaata ttgccctttc cggtccggac ggctaccttt tctacaaagg cagcaatcct 480
tctcaagctc tgccgacggg caaggcgatt tacaaaggta cttgggatta tgtaaccgat 540

-continued

```
gccaaggaaa aacagaagtt tccccagttg ggtagttttc aagcggggga taggtacggg    600
gctctgtctg ccgaggaaga ggatgtgttg cgcaacaaaa gcgaggcgaa ggaaggtcag    660
accgatttcg ggctgaccag cgagtttgag gtggacttcg ccgccaagac catgaccggc    720
aaactctacc gcaataaccg gattaccaat aacgaaaccg aaaatagaga caaacaaatt    780
aaacgttacg acattcaggc taacctgcac ggcaaccgct tcaacggcaa ggcaacggca    840
accgacaaac caaagagaaa tgaaaccaaa caacatccct ttgtttccga ctcgtcttct    900
ttgagcggcg gcttttcgg cccgcagggt gaggaattgg gtttccgctt tttgagcaac    960
gatcaaaaag ttgccgttgt cggcagcgcg aaaacccaag acaaagccgc aaatggcaat   1020
actgcggcgg cttcaggcga tgcaagcgtt ccgcatcaa acggtgcggc aggcacgtcg    1080
tctgaaaacg gtaagctgac cacggttttg gatgcggttg aattgacact aaacgacaag   1140
aaaatcaaaa atctcgacaa cttcagcaat gccgcccaac tggttgtcga cggcattatg   1200
attccgctcc tgcccgagac ttccgaaagt gggaacaatc aggcagataa aggtaaaaac   1260
ggcggaacag cctttacccg caaatttgac cacacgccga aaagcgatga aaagacacc    1320
caagcaggca cggcggcgaa tggcgcgcaa accgcttcgg gtacggcagg cgacacaagt   1380
ggcaaaacaa aaacctatca gtcgaagtc tgctgttcca acctcaatta tctgaaatac    1440
ggaatgttga cacgcaaaaa cagcgaatcc gcgatgcagg caggcgaaag cagtagtcaa   1500
actcctgccg cccaaacggc acagggcgca caaagtatgt tcctccaagg cgagcgcacc   1560
gatgaaaaca agattccaac cgaccaaaac gtcgtttatc gggggtcttg gtacgggcat   1620
attgccagca gcacaagctg gagcggcaat gcttccaatg caacgagtgg caacagggcg   1680
gaatttactg tgaatttcga tacgaaaaaa attaccggca gttaaccgc tgaaaacagg    1740
caggaggcaa cctttaccat tgatggtaag attgagggca acggctttga aggtacggca   1800
aaaactgctg aattaggttt tgatctcgat caaagcaata ccaccggcac gcctaaggca   1860
tatatcacaa acgccaaggt gcagggcggt ttttacggac ctaaagccga agagttgggc   1920
ggatggtttg cctatccggg cgataaacaa acggaaaata caacagttgc atccggcaat   1980
ggaaattcag caagcagtgc aactgtcgta ttcggtgcga acgccaaaa gcctgtgcaa    2040
taa                                                                 2043
```

<210> SEQ ID NO 18
<211> LENGTH: 680
<212> TYPE: PRT
<213> ORGANISM: Neisseria meningitidis

<400> SEQUENCE: 18

```
Met Val Leu Pro Val Phe Leu Leu Ser Ala Cys Leu Gly Gly Gly
  1               5                  10                  15

Ser Phe Asp Leu Asp Ser Val Asp Thr Glu Ala Pro Arg Pro Ala Pro
             20                  25                  30

Lys Tyr Gln Asp Val Ser Ser Glu Thr Pro Gln Ala Gln Lys Asp Gln
         35                  40                  45

Gly Gly Tyr Gly Phe Ala Met Arg Phe Lys Arg Arg Asn Trp His Pro
     50                  55                  60

Lys Asn Lys Glu Asp His Lys Ala Leu Ser Glu Ala Asp Trp Glu Lys
 65                  70                  75                  80

Leu Gly Ala Gly Lys Pro Asp Glu Phe Pro Gln Lys Asn Glu Ile Ser
                 85                  90                  95

Ala Met Asp Lys Gly Thr Leu Asn Glu Ser Ile Thr Pro Gly Asp Gly
```

```
                    100                 105                 110
Lys Ser Arg Ala Glu Gly Tyr Thr Asp Phe Gln Tyr Val Arg Ser Gly
                115                 120                 125
Tyr Ile Tyr Arg Asn Gly Val Asn Lys Ile Asp Tyr Gln Asn Asn Ile
            130                 135                 140
Ala Leu Ser Gly Pro Asp Gly Tyr Leu Phe Tyr Lys Gly Ser Asn Pro
145                 150                 155                 160
Ser Gln Ala Leu Pro Thr Gly Lys Ala Ile Tyr Lys Gly Thr Trp Asp
                165                 170                 175
Tyr Val Thr Asp Ala Lys Glu Lys Gln Lys Phe Pro Gln Leu Gly Ser
            180                 185                 190
Phe Gln Ala Gly Asp Arg Tyr Gly Ala Leu Ser Ala Glu Glu Glu Asp
                195                 200                 205
Val Leu Arg Asn Lys Ser Glu Ala Lys Glu Gly Gln Thr Asp Phe Gly
210                 215                 220
Leu Thr Ser Glu Phe Glu Val Asp Phe Ala Ala Lys Thr Met Thr Gly
225                 230                 235                 240
Lys Leu Tyr Arg Asn Asn Arg Ile Thr Asn Asn Glu Thr Glu Asn Arg
                245                 250                 255
Asp Lys Gln Ile Lys Arg Tyr Asp Ile Gln Ala Asn Leu His Gly Asn
                260                 265                 270
Arg Phe Asn Gly Lys Ala Thr Ala Thr Asp Lys Pro Lys Glu Asn Glu
            275                 280                 285
Thr Lys Gln His Pro Phe Val Ser Asp Ser Ser Leu Ser Gly Gly
            290                 295                 300
Phe Phe Gly Pro Gln Gly Glu Glu Leu Gly Phe Arg Phe Leu Ser Asn
305                 310                 315                 320
Asp Gln Lys Val Ala Val Gly Ser Ala Lys Thr Gln Asp Lys Ala
                325                 330                 335
Ala Asn Gly Asn Thr Ala Ala Ser Gly Asp Ala Ser Val Ser Ala
            340                 345                 350
Ser Asn Gly Ala Ala Gly Thr Ser Ser Glu Asn Gly Lys Leu Thr Thr
            355                 360                 365
Val Leu Asp Ala Val Glu Leu Thr Leu Asn Asp Lys Lys Ile Lys Asn
370                 375                 380
Leu Asp Asn Phe Ser Asn Ala Ala Gln Leu Val Val Asp Gly Ile Met
385                 390                 395                 400
Ile Pro Leu Leu Pro Glu Thr Ser Glu Ser Gly Asn Asn Gln Ala Asp
                405                 410                 415
Lys Gly Lys Asn Gly Gly Thr Ala Phe Thr Arg Lys Phe Asp His Thr
            420                 425                 430
Pro Lys Ser Asp Glu Lys Asp Thr Gln Ala Gly Thr Ala Ala Asn Gly
            435                 440                 445
Ala Gln Thr Ala Ser Gly Thr Ala Gly Asp Thr Ser Gly Lys Thr Lys
            450                 455                 460
Thr Tyr Gln Val Glu Val Cys Cys Ser Asn Leu Asn Tyr Leu Lys Tyr
465                 470                 475                 480
Gly Met Leu Thr Arg Lys Asn Ser Glu Ser Ala Met Gln Ala Gly Glu
                485                 490                 495
Ser Ser Ser Gln Thr Pro Ala Ala Gln Thr Ala Gln Gly Ala Gln Ser
            500                 505                 510
Met Phe Leu Gln Gly Glu Arg Thr Asp Glu Asn Lys Ile Pro Thr Asp
            515                 520                 525
```

-continued

```
Gln Asn Val Val Tyr Arg Gly Ser Trp Tyr Gly His Ile Ala Ser Ser
                530                 535                 540

Thr Ser Trp Ser Gly Asn Ala Ser Asn Ala Thr Ser Gly Asn Arg Ala
545                 550                 555                 560

Glu Phe Thr Val Asn Phe Asp Thr Lys Lys Ile Thr Gly Lys Leu Thr
                565                 570                 575

Ala Glu Asn Arg Gln Glu Ala Thr Phe Thr Ile Asp Gly Lys Ile Glu
            580                 585                 590

Gly Asn Gly Phe Glu Gly Thr Ala Lys Thr Ala Glu Leu Gly Phe Asp
        595                 600                 605

Leu Asp Gln Ser Asn Thr Thr Gly Thr Pro Lys Ala Tyr Ile Thr Asn
            610                 615                 620

Ala Lys Val Gln Gly Gly Phe Tyr Gly Pro Lys Ala Glu Glu Leu Gly
625                 630                 635                 640

Gly Trp Phe Ala Tyr Pro Gly Asp Lys Gln Thr Glu Asn Thr Thr Val
                645                 650                 655

Ala Ser Gly Asn Gly Asn Ser Ala Ser Ser Ala Thr Val Val Phe Gly
            660                 665                 670

Ala Lys Arg Gln Lys Pro Val Gln
        675                 680

<210> SEQ ID NO 19
<211> LENGTH: 4113
<212> TYPE: DNA
<213> ORGANISM: Neisseria meningitidis
<220> FEATURE:
<221> NAME/KEY: misc_feature
<222> LOCATION: 6, 7, 8, 9, 10, 4098, 4099, 4100, 4101, 4102
<223> OTHER INFORMATION: n = A,T,C or G

<400> SEQUENCE: 19
gtgtgnnnnn ctccgaatgg acgcggattg agccacaacc gctatacgca gtttgatgtt      60
gacaacaaag gggcagtgtt aaacaacgac cgtaacaata atccgtttct ggtcaaaggc     120
agtgcgcaat tgattttgaa cgaggtacgc ggtacggcta gcaaactcaa cggcatcgtt     180
accgtaggcg gtcaaaaggc cgacgtgatt attgccaacc ccaacggcat taccgttaat     240
ggcggcggct ttaaaaacgt cggccgcggt atcttaacca ccggtacgcc tcaaatcggc     300
aaagacggtg ccttgacggg atttgacgtg cgccaaggca cattgaccgt cggtacgtca     360
ggttggaacg acaaaggcgg agccgattac accgaagtgc ttgcccgtgc ggttgctttg     420 cagggggaaat tgcagggtaa aaacctggcg gtttcgaccg cgcacagaa agtagattac     480 gccagcggtg aaatcagcgc aggaacggca gcaggtacga aaccgaccgt tgccctcgat     540
actgccgcat tgggtggtat gtacgcagac agcattaccc tgattgccaa tgaaaaaggc     600
gtaggcgtca aaaatgccgg cacactcgaa gcggccaagc aattgattgt gacttcgtca     660
ggccgcattg aaaacagcgg ccgcatcgcc accactgccg acggcaccga agcttcaccg     720
acttatctct ccatcgaaac caccgaaaaa ggagcggcag gcacatttat ctccaatggt     780
ggtcggatcg agagcaaagg cttattggtt attgagacgg gagaagatat cagcttgcgt     840
aacggagccg tggtgcagaa taacggcagt cgcccagcta ccacggtatt aaatgctggt     900
cataatttgg tgattgagag taaaactaat gtgaacaatg ccaaaggctc ggctaatctg     960
tcggccggcg gtcgtactac gatcaatgat gctactattc aagcgggcag ttccgtgtac    1020
agctccacca aaggcgatac tgaattgggt gaaaatacccc gtattattgc tgaaaacgta    1080
accgtattgt ccaacggcag tatttggcagt gctgctgtaa ttgaggctaa agacactgca    1140
```

```
cacattgaag cgggtaaacc gctttcttta gagacttcaa acgttgcttc taacatccgt    1200
ttgaacaacg gtagcattaa aggcggaaag caggtggtat tgatggctga tgacgacatt    1260
caggcaaaag cctcccacct gaatgcgtcc ggcaatctgt atattcatgc aggtaaggat    1320
ctggatttga atgccgataa agacttatca acacaaagta tcagcctgag ggcagacaac    1380
accgccctca tcagcagcaa cggtaacacc ttgactgcag aaaagaatct ggatattcag    1440
gcaggtagct tgagtgtgcg tcaaagtaat ctgcaatcca gtggcggtaa tgtgcagatg    1500
agcgcgacta aaggcaacat cagcttgaat cagagttgga taaatgccag tcagaatatt    1560
gatacggcag cacttcaagg caatattatt tcagacggtc tgactgctgt tgccgaagtt    1620
ggacgcgtat ctcttcttgc aacggcaat  gttgatttca cggtctaaa  taccttgatt    1680 gcggaaggag acattaatgc tggttcagtc ggtaaaggcc gtctgaaaat ggacaatacc    1740
gatatttatg cttctgcagg cgatgtgaaa ctggttgccg gaggtcaatt agatttaggc    1800
aacggcaccg ttaacggcgg tcatatcagc ttagacagca ataaaggcag catggtggtg    1860
cagaatgtac acctgaatgc ccgcgcatca ctgaaagtgg atgcggatca aactttaacc    1920
attaataaca gcaagctcaa ttccgatcac aatacccaga ttaatacaaa tcatggtcat    1980
atgacgctta atcagcttga tgctcattca cgtcgtcata tgagtatcag tgcacagggt    2040
aaaggcaaag gaaagacag  cggtcaaatt ttacaaaacg accagcaaaa cagtaaaagt    2100
actttggcgg cagatggtgt attgtcattg aacagcagcg cattacaggt tttggacaat    2160
actaccctgc gcggtggcgc gataaacatc aaagctggcg gaggcatcat caaacggggg    2220
catatcgatt gggaaaccca agatacggca actatgcgtt cagcggaact gaaaccactg    2280
tccggtatga tgtcgataga atcggcggt  gataaccctt taaccgttga acccggtaac    2340
cgtatcgttt ctgcaggtga tttggccgtg aaccacaacg gcacattcca aatcagtgcc    2400
agagcaggaa ataacggcaa tccgagtgcg caaacagcca gcgtttcagc taaaggcaat    2460
atcgggattg tggcgggaga ggtggatatt gatgcagcaa atattgccgc agggaaagat    2520
ttggctttag tggcaactaa agggaatatt tcactaaaca gtattaggaa tacgtttagt    2580
aactatcaat tgaaaacaga taaacacaat atcacacagc aacttactga tgtagagcag    2640
gagcttagta agttaacgag cgatcctaaa tatcgtaaag cacaggatct ttcacaaatg    2700
ttgaggcgta aatataagag gcgtgacaaa gtattcggtg atagtgaggc cagattacgt    2760
ggtttacgag caaagataaa tgctgctgat gaggcttggg cagaacgcca atccccagta    2820 aaaagcgttac ttgaacgtaa acaattgtta caacaagccc ttttaacagt ttcccaaccg    2880
ggtagtggtc acgaaaacca aggtagcacc cttagcggtc aaaatatcaa actgctcgct    2940
gcaggtggta tccgtatcca gggctccaaa gttgctgcca cccaacaggc aaatatccaa    3000
gctgcaggat ttttacctgc accagccgca gaggaactgc aagaaggtcg acttcaatca    3060
gccattgaca tcagcggtgt acttgatact tttgaatatg gtcagcaagg cagcgataaa    3120
tacggctatg ccatttttcag caggccatct gaaatttcag gaaaaacagg tgttaccctc    3180
tctgcaccaa atgccaatga gaacagccgc atcagtctga gtgcggcaaa catcgaagct    3240
gaaaacggca aaatcaaaat tcaatcctac ggcgaccaat cctattacgc cggacagggc    3300
gaactctata cctttgaacg ccgcagctac aaaaccggca atggtacaa  ccgcaaacac    3360 attaccgaag tcaaagaaca caaaaacgcc aagcccgacg cagtaaacct cagcgcatcc    3420
caaggcatcg acatcaaatc tggtggcagc atcgacgcct acgccaccgc attcgatgcc    3480
cccaaaggca gcattaacat cgaagccggg cggaaattga cactctatgc cgtagaagag    3540
```

```
ctcaactacg acaaactaga cagccaaaaa aggcgcagat ttctcggcat cagctacagc   3600
aaagcacacg acaccaccac ccaagtcatg aaaaccgcgc tgccctcaag ggtagttgca   3660
gaatcagcca atctgcaatc aggttgggat accaaactgc aaggcacaca gtttgaaacc   3720
acactgggtg gcgcaaccat acgcgcaggc gtaggcgagc aggcacgggc agatgccaag   3780
attatcctcg aagggatcaa agcagcatc cacacagaaa ccgtgagcag cagcaaatct   3840
actctatggc aaaaacaggc aggacggggc agtaacatcg aaaccttgca attgccgagt   3900
ttcaccggtc ccgttgcgcc cgtactgtcc gcacccggcg gttacattgt cgatattccc   3960
caaggcaatc tgaaaaccca aatcgaaacc ctcaccaaac agcccgagta tgcttatttg   4020
aacaacttca agttgcgaaa aacatcaact ggaatcacgt gcagcttgct tacgataaat   4080
gggactacaa acaggagnnn nncacacact taa                                4113
```

<210> SEQ ID NO 20
<211> LENGTH: 1370
<212> TYPE: PRT
<213> ORGANISM: Neisseria meningitidis
<220> FEATURE:
<221> NAME/KEY: VARIANT
<222> LOCATION: 2, 3, 4, 1366, 1367, 1368
<223> OTHER INFORMATION: Xaa = Any Amino Acid

<400> SEQUENCE: 20

```
Met Xaa Xaa Xaa Pro Asn Gly Arg Gly Leu Ser His Asn Arg Tyr Thr
 1               5                  10                  15

Gln Phe Asp Val Asp Asn Lys Gly Ala Val Leu Asn Asn Asp Arg Asn
            20                  25                  30

Asn Asn Pro Phe Leu Val Lys Gly Ser Ala Gln Leu Ile Leu Asn Glu
        35                  40                  45

Val Arg Gly Thr Ala Ser Lys Leu Asn Gly Ile Val Thr Val Gly Gly
    50                  55                  60

Gln Lys Ala Asp Val Ile Ile Ala Asn Pro Asn Gly Ile Thr Val Asn
65                  70                  75                  80

Gly Gly Gly Phe Lys Asn Val Gly Arg Gly Ile Leu Thr Thr Gly Thr
                85                  90                  95

Pro Gln Ile Gly Lys Asp Gly Ala Leu Thr Gly Phe Asp Val Arg Gln
            100                 105                 110

Gly Thr Leu Thr Val Gly Thr Ser Gly Trp Asn Asp Lys Gly Gly Ala
        115                 120                 125

Asp Tyr Thr Glu Val Leu Ala Arg Ala Val Ala Leu Gln Gly Lys Leu
    130                 135                 140

Gln Gly Lys Asn Leu Ala Val Ser Thr Gly Ala Gln Lys Val Asp Tyr
145                 150                 155                 160

Ala Ser Gly Glu Ile Ser Ala Gly Thr Ala Ala Gly Thr Lys Pro Thr
                165                 170                 175

Val Ala Leu Asp Thr Ala Ala Leu Gly Gly Met Tyr Ala Asp Ser Ile
            180                 185                 190

Thr Leu Ile Ala Asn Glu Lys Gly Val Gly Val Lys Asn Ala Gly Thr
        195                 200                 205

Leu Glu Ala Ala Lys Gln Leu Ile Val Thr Ser Ser Gly Arg Ile Glu
    210                 215                 220

Asn Ser Gly Arg Ile Ala Thr Thr Ala Asp Gly Thr Glu Ala Ser Pro
225                 230                 235                 240

Thr Tyr Leu Ser Ile Glu Thr Thr Glu Lys Gly Ala Ala Gly Thr Phe
                245                 250                 255
```

```
Ile Ser Asn Gly Gly Arg Ile Glu Ser Lys Gly Leu Leu Val Ile Glu
            260                 265                 270

Thr Gly Glu Asp Ile Ser Leu Arg Asn Gly Ala Val Val Gln Asn Asn
        275                 280                 285

Gly Ser Arg Pro Ala Thr Thr Val Leu Asn Ala Gly His Asn Leu Val
    290                 295                 300

Ile Glu Ser Lys Thr Asn Val Asn Asn Ala Lys Gly Ser Ala Asn Leu
305                 310                 315                 320

Ser Ala Gly Gly Arg Thr Thr Ile Asn Asp Ala Thr Ile Gln Ala Gly
                325                 330                 335

Ser Ser Val Tyr Ser Ser Thr Lys Gly Asp Thr Glu Leu Gly Glu Asn
            340                 345                 350

Thr Arg Ile Ile Ala Glu Asn Val Thr Val Leu Ser Asn Gly Ser Ile
        355                 360                 365

Gly Ser Ala Ala Val Ile Glu Ala Lys Asp Thr Ala His Ile Glu Ala
    370                 375                 380

Gly Lys Pro Leu Ser Leu Glu Thr Ser Asn Val Ala Ser Asn Ile Arg
385                 390                 395                 400

Leu Asn Asn Gly Ser Ile Lys Gly Gly Lys Gln Val Val Leu Met Ala
                405                 410                 415

Asp Asp Asp Ile Gln Ala Lys Ala Ser His Leu Asn Ala Ser Gly Asn
            420                 425                 430

Leu Tyr Ile His Ala Gly Lys Asp Leu Asp Leu Asn Ala Asp Lys Asp
        435                 440                 445

Leu Ser Thr Gln Ser Ile Ser Leu Arg Ala Asp Asn Thr Ala Leu Ile
    450                 455                 460

Ser Ser Asn Gly Asn Thr Leu Thr Ala Glu Lys Asn Leu Asp Ile Gln
465                 470                 475                 480

Ala Gly Ser Leu Ser Val Arg Gln Ser Asn Leu Gln Ser Ser Gly Gly
                485                 490                 495

Asn Val Gln Met Ser Ala Thr Lys Gly Asn Ile Ser Leu Asn Gln Ser
            500                 505                 510

Trp Ile Asn Ala Ser Gln Asn Ile Asp Thr Ala Ala Leu Gln Gly Asn
        515                 520                 525

Ile Ile Ser Asp Gly Leu Thr Ala Val Ala Glu Val Gly Arg Val Ser
    530                 535                 540

Leu Leu Ala Asn Gly Asn Val Asp Phe Asn Gly Leu Asn Thr Leu Ile
545                 550                 555                 560

Ala Glu Gly Asp Ile Asn Ala Gly Ser Val Gly Lys Gly Arg Leu Lys
                565                 570                 575

Met Asp Asn Thr Asp Ile Tyr Ser Ala Gly Asp Val Lys Leu Val
            580                 585                 590

Ala Gly Gly Gln Leu Asp Leu Gly Asn Gly Thr Val Asn Gly Gly His
        595                 600                 605

Ile Ser Leu Asp Ser Asn Lys Gly Ser Met Val Val Gln Asn Val His
    610                 615                 620

Leu Asn Ala Arg Ala Ser Leu Lys Val Asp Ala Asp Gln Thr Leu Thr
625                 630                 635                 640

Ile Asn Asn Ser Lys Leu Asn Ser Asp His Asn Thr Gln Ile Asn Thr
                645                 650                 655

Asn His Gly His Met Thr Leu Asn Gln Leu Asp Ala His Ser Arg Arg
            660                 665                 670

His Met Ser Ile Ser Ala Gln Gly Lys Gly Lys Gly Lys Asp Ser Gly
        675                 680                 685
```

```
Gln Ile Leu Gln Asn Asp Gln Gln Asn Ser Lys Ser Thr Leu Ala Ala
    690                 695                 700
Asp Gly Val Leu Ser Leu Asn Ser Ser Ala Leu Gln Val Leu Asp Asn
705                 710                 715                 720
Thr Thr Leu Arg Gly Gly Ala Ile Asn Ile Lys Ala Gly Gly Ile
            725                 730                 735
Ile Lys Arg Gly His Ile Asp Trp Glu Thr Gln Asp Thr Ala Thr Met
            740                 745                 750
Arg Ser Ala Glu Leu Lys Pro Leu Ser Gly Met Met Ser Ile Glu Ser
            755                 760                 765
Gly Gly Asp Asn Pro Leu Thr Val Glu Pro Gly Asn Arg Ile Val Ser
770                 775                 780
Ala Gly Asp Leu Ala Val Asn His Asn Gly Thr Phe Gln Ile Ser Ala
785                 790                 795                 800
Arg Ala Gly Asn Asn Gly Asn Pro Ser Ala Gln Thr Ala Ser Val Ser
                805                 810                 815
Ala Lys Gly Asn Ile Gly Ile Val Ala Gly Glu Val Asp Ile Asp Ala
                820                 825                 830
Ala Asn Ile Ala Ala Gly Lys Asp Leu Ala Leu Val Ala Thr Lys Gly
                835                 840                 845
Asn Ile Ser Leu Asn Ser Ile Arg Asn Thr Phe Ser Asn Tyr Gln Leu
    850                 855                 860
Lys Thr Asp Lys His Asn Ile Thr Gln Gln Leu Thr Asp Val Glu Gln
865                 870                 875                 880
Glu Leu Ser Lys Leu Thr Ser Asp Pro Lys Tyr Arg Lys Ala Gln Asp
                885                 890                 895
Leu Ser Gln Met Leu Arg Arg Lys Tyr Lys Arg Arg Asp Lys Val Phe
            900                 905                 910
Gly Asp Ser Glu Ala Arg Leu Arg Gly Leu Arg Ala Lys Ile Asn Ala
            915                 920                 925
Ala Asp Glu Ala Trp Ala Glu Arg Gln Ser Pro Val Lys Ala Leu Leu
    930                 935                 940
Glu Arg Lys Gln Leu Leu Gln Gln Ala Leu Leu Thr Val Ser Gln Pro
945                 950                 955                 960
Gly Ser Gly His Glu Asn Gln Gly Ser Thr Leu Ser Gly Gln Asn Ile
                965                 970                 975
Lys Leu Leu Ala Ala Gly Gly Ile Arg Ile Gln Gly Ser Lys Val Ala
            980                 985                 990
Ala Thr Gln Gln Ala Asn Ile Gln Ala Ala Gly Phe Leu Pro Ala Pro
    995                 1000                1005
Ala Ala Glu Glu Leu Gln Glu Gly Arg Leu Gln Ser Ala Ile Asp Ile
    1010                1015                1020
Ser Gly Val Leu Asp Thr Phe Glu Tyr Gly Gln Gln Gly Ser Asp Lys
1025                1030                1035                1040
Tyr Gly Tyr Ala Ile Phe Ser Arg Pro Ser Glu Ile Ser Gly Lys Thr
                1045                1050                1055
Gly Val Thr Leu Ser Ala Pro Asn Ala Asn Glu Asn Ser Arg Ile Ser
                1060                1065                1070
Leu Ser Ala Ala Asn Ile Glu Ala Glu Asn Gly Lys Ile Lys Ile Gln
            1075                1080                1085
Ser Tyr Gly Asp Gln Ser Tyr Tyr Ala Gly Gln Gly Glu Leu Tyr Thr
    1090                1095                1100
Phe Glu Arg Arg Ser Tyr Lys Thr Gly Lys Trp Tyr Asn Arg Lys His
```

```
1105                1110                1115                1120

Ile Thr Glu Val Lys Glu His Lys Asn Ala Lys Pro Asp Ala Val Asn
                1125                1130                1135

Leu Ser Ala Ser Gln Gly Ile Asp Ile Lys Ser Gly Gly Ser Ile Asp
            1140                1145                1150

Ala Tyr Ala Thr Ala Phe Asp Ala Pro Lys Gly Ser Ile Asn Ile Glu
        1155                1160                1165

Ala Gly Arg Lys Leu Thr Leu Tyr Ala Val Glu Glu Leu Asn Tyr Asp
    1170                1175                1180

Lys Leu Asp Ser Gln Lys Arg Arg Arg Phe Leu Gly Ile Ser Tyr Ser
1185                1190                1195                1200

Lys Ala His Asp Thr Thr Thr Gln Val Met Lys Thr Ala Leu Pro Ser
                1205                1210                1215

Arg Val Val Ala Glu Ser Ala Asn Leu Gln Ser Gly Trp Asp Thr Lys
            1220                1225                1230

Leu Gln Gly Thr Gln Phe Glu Thr Thr Leu Gly Gly Ala Thr Ile Arg
        1235                1240                1245

Ala Gly Val Gly Glu Gln Ala Arg Ala Asp Ala Lys Ile Ile Leu Glu
    1250                1255                1260

Gly Ile Lys Ser Ser Ile His Thr Glu Thr Val Ser Ser Ser Lys Ser
1265                1270                1275                1280

Thr Leu Trp Gln Lys Gln Ala Gly Arg Gly Ser Asn Ile Glu Thr Leu
                1285                1290                1295

Gln Leu Pro Ser Phe Thr Gly Pro Val Ala Pro Val Leu Ser Ala Pro
            1300                1305                1310

Gly Gly Tyr Ile Val Asp Ile Pro Gln Gly Asn Leu Lys Thr Gln Ile
        1315                1320                1325

Glu Thr Leu Thr Lys Gln Pro Glu Tyr Ala Tyr Leu Asn Asn Phe Lys
    1330                1335                1340

Leu Arg Lys Thr Ser Thr Gly Ile Thr Cys Ser Leu Leu Thr Ile Asn
1345                1350                1355                1360

Gly Thr Thr Asn Arg Xaa Xaa Xaa His Thr
                1365                1370

<210> SEQ ID NO 21
<211> LENGTH: 2205
<212> TYPE: DNA
<213> ORGANISM: Neisseria meningitidis
<220> FEATURE:
<221> NAME/KEY: misc_feature
<222> LOCATION: 4, 5, 6, 7, 8
<223> OTHER INFORMATION: n = A,T,C or G

<400> SEQUENCE: 21
gtgnnnnngc aaatcaaact gcaatcctac ggcgaccaat cctattacgc cggacagggc      60
gaactctata cctttgaacg ccgcagctac aaaaccggca aatggtacaa ccgcaaacac     120
attaccgaag tcaaagaaca caaaaacgcc aagcccgacg cagtaaacct cagcgcatcc     180
caaggcatcg acatcaaatc tggtggcagc atcgacgcct acgccaccgc attcgatgcc     240
cccaaaggca gcattaacat cgaagccggg cggaaattga cactctatgc cgtagaagag     300
ctcaactacg acaaactaga cagccaaaaa aggcgcagat ttctcggcat cagctacagc     360
aaagcacacg acaccaccac ccaagtcatg aaaaccgcgc tgccctcaag ggtagttgca     420
gaatcagcca atctgcaatc aggttgggat accaaactgc aaggcacaca gtttgaaacc     480
acactgggtg gcgcaaccat acgcgcaggc gtaggcgagc aggcacgggc agatgccaag     540
```

```
attatcctcg aagggatcaa aagcagcatc cacacagaaa ccgtgagcag cagcaaatct    600
actctatggc aaaaacaggc aggacggggc agtaacatcg aaaccttgca attgccgagt    660
ttcaccggtc ccgttgcgcc cgtactgtcc gcacccggcg gttacattgt cgatattccc    720
caaggcaatc tgaaaaccca aatcgaaacc ctcaccaaac agcccgagta tgcttatttg    780
aaacaacttc aagttgcgaa aacatcaac tggaatcagg tgcagcttgc ttacgataaa    840
tgggactaca acaggaggg cttaaccgaa gcaggtgcgg cgattatcgc actggccgtt    900
accgtggtca cctcaggcgc aggaaccgga gccgtattgg gattaaacgg tgcggccgcc    960
gccgcaaccg atgcagcatt tgcctctttg gccagccagg cttccgtatc gttcatcaac    1020
aacaaaggca atatcggtaa caccctgaaa gagctgggca gaagcagcac ggtgaaaaat    1080
ctggtggttg ccgccgctac cgcaggcgta tccaacaaaa tcggtgcttc ctcccttgcc    1140
acttggagcg aaaccccttg ggtaaacaac ctcaacgtca acttggccaa tgcgggcagt    1200
gccgcactga ttaataccgc tgtcaacggc ggcagcctga agacaatct ggaagcgaat    1260 atccttgcgg cttttggtca taccgcgcat ggagaagcag ccagtaaaat caaacagttg    1320
gatcagcact acatagtcca caagattgcc catgccatag cgggctgtgc ggcagcggcg    1380
gcgaataagg gcaagtgtca ggatggtgcg ataggcgctg cagtcggtga gattgttggt    1440
gaggctttgg ttaagaatac cgatttcagc ggtatgactg cttctgaaat tgaaaaagct    1500
aaagcgaata ttactgcgta tgcaaaattg gtagccggag cgactgtagg tgttacagga    1560
ggcaatgttg atgtggcggc aaatgcttcc gaaacagctg ttaaaaataa tgcattagat    1620
attatttggg atatcggcaa cctcgtatgg gacggcggta atggatttta cgccaaatct    1680
attggcgata agcagatggc tcgagaagcg gcgattgatt ttggtgtgga tgccgccgca    1740
gctgccgttc cctttgttcc ggcaggtgcg actaaaatca gccgaggcgg ggcttatgtt    1800
ctgaaggcgg gagacgaagc agttgatacg gctaaagcca tacaggaaat tcagaagcag    1860
accggaatca agcttactta tgataaggtt aataaggttt ggacaacacc ggcggggtta    1920
gattatgggt tagatgctaa gcatggtaat aggattaaac atgtttttagc ccatacaatt    1980 ccaaatccaa acaaacctgt tcattctgtt tttaatgtgt cccgtaaaga agttttgcct    2040
ttggttgatg aagcttggag aatgaaagga aatcctttgc caaatgattc atccgtatat    2100
cttgtagata tgaagaaacc tattggaaca aaaggagaaa caaagtgcg gattgttgtg    2160 caaaaaggaa caaataaaat catttctgca tatcctcaga ataa                    2205
```

<210> SEQ ID NO 22
<211> LENGTH: 734
<212> TYPE: PRT
<213> ORGANISM: Neisseria meningitidis
<220> FEATURE:
<221> NAME/KEY: VARIANT
<222> LOCATION: 2, 3
<223> OTHER INFORMATION: Xaa = Any Amino Acid

<400> SEQUENCE: 22

```
Met Xaa Xaa Gln Ile Lys Leu Gln Ser Tyr Gly Asp Gln Ser Tyr Tyr
 1               5                  10                  15

Ala Gly Gln Gly Glu Leu Tyr Thr Phe Glu Arg Arg Ser Tyr Lys Thr
                20                  25                  30

Gly Lys Trp Tyr Asn Arg Lys His Ile Thr Glu Val Lys Glu His Lys
            35                  40                  45

Asn Ala Lys Pro Asp Ala Val Asn Leu Ser Ala Ser Gln Gly Ile Asp
        50                  55                  60
```

-continued

```
Ile Lys Ser Gly Gly Ser Ile Asp Ala Tyr Ala Thr Ala Phe Asp Ala
 65                  70                  75                  80

Pro Lys Gly Ser Ile Asn Ile Glu Ala Gly Arg Lys Leu Thr Leu Tyr
                 85                  90                  95

Ala Val Glu Glu Leu Asn Tyr Asp Lys Leu Asp Ser Gln Lys Arg Arg
            100                 105                 110

Arg Phe Leu Gly Ile Ser Tyr Ser Lys Ala His Asp Thr Thr Thr Gln
        115                 120                 125

Val Met Lys Thr Ala Leu Pro Ser Arg Val Val Ala Glu Ser Ala Asn
130                 135                 140

Leu Gln Ser Gly Trp Asp Thr Lys Leu Gln Gly Thr Gln Phe Glu Thr
145                 150                 155                 160

Thr Leu Gly Gly Ala Thr Ile Arg Ala Gly Val Gly Glu Gln Ala Arg
                165                 170                 175

Ala Asp Ala Lys Ile Ile Leu Glu Gly Ile Lys Ser Ser Ile His Thr
            180                 185                 190

Glu Thr Val Ser Ser Lys Ser Thr Leu Trp Gln Lys Gln Ala Gly
        195                 200                 205

Arg Gly Ser Asn Ile Glu Thr Leu Gln Leu Pro Ser Phe Thr Gly Pro
210                 215                 220

Val Ala Pro Val Leu Ser Ala Pro Gly Gly Tyr Ile Val Asp Ile Pro
225                 230                 235                 240

Gln Gly Asn Leu Lys Thr Gln Ile Glu Thr Leu Thr Lys Gln Pro Glu
                245                 250                 255

Tyr Ala Tyr Leu Lys Gln Leu Gln Val Ala Lys Asn Ile Asn Trp Asn
            260                 265                 270

Gln Val Gln Leu Ala Tyr Asp Lys Trp Asp Tyr Lys Gln Glu Gly Leu
        275                 280                 285

Thr Glu Ala Gly Ala Ala Ile Ile Ala Leu Ala Val Thr Val Val Thr
290                 295                 300

Ser Gly Ala Gly Thr Gly Ala Val Leu Gly Leu Asn Gly Ala Ala Ala
305                 310                 315                 320

Ala Ala Thr Asp Ala Ala Phe Ala Ser Leu Ala Ser Gln Ala Ser Val
                325                 330                 335

Ser Phe Ile Asn Asn Lys Gly Asn Ile Gly Asn Thr Leu Lys Glu Leu
            340                 345                 350

Gly Arg Ser Ser Thr Val Lys Asn Leu Val Val Ala Ala Thr Ala
        355                 360                 365

Gly Val Ser Asn Lys Ile Gly Ala Ser Ser Leu Ala Thr Trp Ser Glu
370                 375                 380

Thr Pro Trp Val Asn Asn Leu Asn Val Asn Leu Ala Asn Ala Gly Ser
385                 390                 395                 400

Ala Ala Leu Ile Asn Thr Ala Val Asn Gly Gly Ser Leu Lys Asp Asn
                405                 410                 415

Leu Glu Ala Asn Ile Leu Ala Ala Leu Val Asn Thr Ala His Gly Glu
            420                 425                 430

Ala Ala Ser Lys Ile Lys Gln Leu Asp Gln His Tyr Ile Val His Lys
        435                 440                 445

Ile Ala His Ala Ile Ala Gly Cys Ala Ala Ala Ala Asn Lys Gly
450                 455                 460

Lys Cys Gln Asp Gly Ala Ile Gly Ala Ala Val Gly Glu Ile Val Gly
465                 470                 475                 480

Glu Ala Leu Val Lys Asn Thr Asp Phe Ser Gly Met Thr Ala Ser Glu
                485                 490                 495
```

```
Ile Glu Lys Ala Lys Ala Asn Ile Thr Ala Tyr Ala Lys Leu Val Ala
                500                 505                 510
Gly Ala Thr Val Gly Val Thr Gly Gly Asn Val Asp Val Ala Ala Asn
            515                 520                 525
Ala Ser Glu Thr Ala Val Lys Asn Asn Ala Leu Asp Ile Ile Trp Asp
        530                 535                 540
Ile Gly Asn Leu Val Trp Asp Gly Gly Lys Trp Ile Tyr Ala Lys Ser
545                 550                 555                 560
Ile Gly Asp Lys Gln Met Ala Arg Glu Ala Ala Ile Asp Phe Gly Val
                565                 570                 575
Asp Ala Ala Ala Ala Val Pro Phe Val Pro Ala Gly Ala Thr Lys
            580                 585                 590
Ile Ser Arg Gly Gly Ala Tyr Val Leu Lys Ala Gly Asp Glu Ala Val
        595                 600                 605
Asp Thr Ala Lys Ala Ile Gln Glu Ile Gln Lys Gln Thr Gly Ile Lys
    610                 615                 620
Leu Thr Tyr Asp Lys Val Asn Lys Val Trp Thr Thr Pro Ala Gly Leu
625                 630                 635                 640
Asp Tyr Gly Leu Asp Ala Lys His Gly Asn Arg Ile Lys His Val Leu
                645                 650                 655
Ala His Thr Ile Pro Asn Pro Asn Lys Pro Val His Ser Val Phe Asn
            660                 665                 670
Val Ser Arg Lys Glu Val Leu Pro Leu Val Asp Glu Ala Trp Arg Met
        675                 680                 685
Lys Gly Asn Pro Leu Pro Asn Asp Ser Ser Val Tyr Leu Val Asp Met
    690                 695                 700
Lys Lys Pro Ile Gly Thr Lys Gly Glu Thr Lys Val Arg Ile Val Val
705                 710                 715                 720
Gln Lys Gly Thr Asn Lys Ile Ile Ser Ala Tyr Pro Gln Lys
                725                 730

<210> SEQ ID NO 23
<211> LENGTH: 2664
<212> TYPE: DNA
<213> ORGANISM: Neisseria meningitidis

<400> SEQUENCE: 23
gtgagcatta gcgcaccgta tgccaatgag aacagtcgca tcctgctcag caccacggat     60
atcagttcgg aaaacggcaa aatcaaaatt caatcttacg gtgaccaata ttactatgcg    120
agacagagcg aactctatac cttgaacgc cgcagctaca aaaccggcaa atggtacaac    180
cgcaaacaca ttaccgaagt caaagaacac aaaaacgcca agcccgacgc agtaaccctc    240
agcgcatccc aaggcatcga catcaaatct ggtggcagca tcgacgccta cgccaccgca    300
ttcgatgccc ccaaaggcag cattaacatc gaagccgggc ggaaattgac actctatgcc    360
gtagaagagc tcaactacga caaactagac agccaaaaaa ggcgcagatt tctcggcatc    420
agctacagca agcacacga caccaccacc caagtcatga aaccgcgct gccctcaagg    480 gtagttgcag aatcagccaa cctccaatcg ggctgggata ccaaactgca aggcacacag    540
tttgaaacca cactgggtgg cgcaaccata cgcgcaggcg taggtgagca ggcacgggca    600
gatgccaaga ttatcctcga aggcatcaaa accacgatcc acaacgaaac cgtgagcagc    660
agcaaatctg ctctatggca aaaacaggca ggacggggga gtaacatcga aaccttgcaa    720
ttgccgagtt tcaccggtcc cgttgcgccc gtactgtccg cacccggcgg ttacattgtc    780
```

```
gacatcccca aaggcaatct gaaaaccgaa atcgaaaagc tggccaaaca gcccgaatac    840
gcctacctga acagcttca  gacggccaag aacgtcgatt ggaaacaggt gcagctggcc    900
tacgacaaat gggactataa acaggaaggc ttgaccggag ccggtgcagc gattgtggtg    960
attattgtaa ccgctctaac ttatggatac ggagcggctg cagcgggtag cgtaactgcc   1020
gcaggaagta gtacagccgc agctgcaaca acgacagcgg cagcaactac cactgttct    1080 actgcagctg ccatgcaaac cgcagcttta gcctccttgt atagccaagc agctgtagcc   1140
atcatcaata taaaggcga  tgtaggcaaa gcattaaaag atctcggcac cagtgatacg   1200
gtcaagcaga ttgttacttc cgcactgacg gcggtgcat  taaaccagat gggcgcagat   1260
attgcccaat gaacagcaa  ggtaagaacc gaactgttca gcagtacggg caatcaaacc   1320
attgccaacc ttggaggcag attggccacc aacctcagca atgcaggtat ctcagctggt   1380
atcaataccg ccgttaacgg cggcagcttg aaagacaact taggcaatgc cgcattggga   1440
gcattggtta atagcttcca aggggaagcc gccagcaaaa tcaaaacaac cttcagcgac   1500
gattatgttg ccaaacagtt cgcccacgct ttggcgggtt gtgttagcgg actggtacag   1560
ggaaaatgta agatggggc  aattggcgca gcagttgggg aaatcgtagc tgaatccata   1620
cttggcggca gaaaccctgc tacactcagc gatgcagaaa agcataaagt tatcagttac   1680
tcgaagatta ttgcgggcag cgtggcggca ctcaacggcg gcgatgtgaa tactgcggcg   1740
aatgcggctg aggtagctgt ggtgaataat gctttgaatt ttgacagtac ccctaccaat   1800
gcgaaaaagc atcaaccgca gaagcccgac aaaaccgcac tggaaaaaat catccaaagt   1860
attatgcctg cacatgcggc aggtgcgatg actaatccgc aggataagga tgctgccatt   1920
tggataagca atatccgtaa tggcatcaca ggcccgattg tgattaccag ctatggagtt   1980
tatgcagcag gttggacagc tccgctgatc ggtacagctg gtaaagcagc tatcagcacc   2040
tgtatggcta atccttctgg ttgtactgtc atggttacgc aggctgctga gcgggcgcg   2100 ggaatcgtca cgggtgcggt aacggtaggc aacgcttggg aagctccagt aggagcgttg   2160
tcgaaagcga aggcggctaa gcaagctgct cctaaagaaa caataaacaa tttggcaaat   2220
ttagccaaag cagaacagca gattttattc cgtattgccc aacgcgatac gcaactggat   2280
gcatggaaga cgggattaa  caatagagta aggaaaggag caggcttgct tgatgcaagt   2340
aatattccga taaccattaa cggaaaaacc atcaaacctg tacaagccat aagcttaaag   2400
ggagcacccg tttacagcgg cgtaagcgaa caggagattt ttgcgcttta tcggcagatg   2460
actggccaga atccgaattt tagagttttg cctgacggaa gattagcaaa tggcattatc   2520
agtactggag aatgggcagg aacaaaaatt gcattaagaa attttttcaaa aacagagaat   2580 tcaactcaag cacgatggac attagatttg cagaatcctc catcatttat taaaggtact   2640
aaattggagc ttaaattcca ataa                                          2664
```

<210> SEQ ID NO 24
<211> LENGTH: 887
<212> TYPE: PRT
<213> ORGANISM: Neisseria meningitidis

<400> SEQUENCE: 24

Met Ser Ile Ser Ala Pro Tyr Ala Asn Glu Asn Ser Arg Ile Leu Leu
 1               5                  10                  15

Ser Thr Thr Asp Ile Ser Ser Glu Asn Gly Lys Ile Lys Ile Gln Ser
            20                  25                  30

Tyr Gly Asp Gln Tyr Tyr Tyr Ala Arg Gln Ser Glu Leu Tyr Thr Phe
        35                  40                  45

```
Glu Arg Arg Ser Tyr Lys Thr Gly Lys Trp Tyr Asn Arg Lys His Ile
    50                  55                  60

Thr Glu Val Lys Glu His Lys Asn Ala Lys Pro Asp Ala Val Thr Leu
65                  70                  75                  80

Ser Ala Ser Gln Gly Ile Asp Ile Lys Ser Gly Ser Ile Asp Ala
                    85                  90                  95

Tyr Ala Thr Ala Phe Asp Ala Pro Lys Gly Ser Ile Asn Ile Glu Ala
                100                 105                 110

Gly Arg Lys Leu Thr Leu Tyr Ala Val Glu Glu Leu Asn Tyr Asp Lys
            115                 120                 125

Leu Asp Ser Gln Lys Arg Arg Arg Phe Leu Gly Ile Ser Tyr Ser Lys
130                 135                 140

Ala His Asp Thr Thr Thr Gln Val Met Lys Thr Ala Leu Pro Ser Arg
145                 150                 155                 160

Val Val Ala Glu Ser Ala Asn Leu Gln Ser Gly Trp Asp Thr Lys Leu
                165                 170                 175

Gln Gly Thr Gln Phe Glu Thr Thr Leu Gly Gly Ala Thr Ile Arg Ala
            180                 185                 190

Gly Val Gly Glu Gln Ala Arg Ala Asp Ala Lys Ile Ile Leu Glu Gly
        195                 200                 205

Ile Lys Thr Thr Ile His Asn Glu Thr Val Ser Ser Ser Lys Ser Ala
210                 215                 220

Leu Trp Gln Lys Gln Ala Gly Arg Gly Ser Asn Ile Glu Thr Leu Gln
225                 230                 235                 240

Leu Pro Ser Phe Thr Gly Pro Val Ala Pro Val Leu Ser Ala Pro Gly
                245                 250                 255

Gly Tyr Ile Val Asp Ile Pro Lys Gly Asn Leu Lys Thr Glu Ile Glu
            260                 265                 270

Lys Leu Ala Lys Gln Pro Glu Tyr Ala Tyr Leu Lys Gln Leu Gln Thr
275                 280                 285

Ala Lys Asn Val Asp Trp Lys Gln Val Gln Leu Ala Tyr Asp Lys Trp
            290                 295                 300

Asp Tyr Lys Gln Glu Gly Leu Thr Gly Ala Gly Ala Ala Ile Val Val
305                 310                 315                 320

Ile Ile Val Thr Ala Leu Thr Tyr Gly Tyr Gly Ala Ala Ala Ala Gly
                325                 330                 335

Ser Val Thr Ala Ala Gly Ser Ser Thr Ala Ala Ala Thr Thr Thr
                340                 345                 350

Ala Ala Ala Thr Thr Thr Val Ser Thr Ala Ala Ala Met Gln Thr Ala
            355                 360                 365

Ala Leu Ala Ser Leu Tyr Ser Gln Ala Ala Val Ala Ile Ile Asn Asn
        370                 375                 380

Lys Gly Asp Val Gly Lys Ala Leu Lys Asp Leu Gly Thr Ser Asp Thr
385                 390                 395                 400

Val Lys Gln Ile Val Thr Ser Ala Leu Thr Ala Gly Ala Leu Asn Gln
                405                 410                 415

Met Gly Ala Asp Ile Ala Gln Leu Asn Ser Lys Val Arg Thr Glu Leu
            420                 425                 430

Phe Ser Thr Gly Asn Gln Thr Ile Ala Asn Leu Gly Gly Arg Leu
            435                 440                 445

Ala Thr Asn Leu Ser Asn Ala Gly Ile Ser Ala Gly Ile Asn Thr Ala
        450                 455                 460

Val Asn Gly Gly Ser Leu Lys Asp Asn Leu Gly Asn Ala Ala Leu Gly
```

```
                465                 470                 475                 480
Ala Leu Val Asn Ser Phe Gln Gly Glu Ala Ala Ser Lys Ile Lys Thr
                    485                 490                 495

Thr Phe Ser Asp Asp Tyr Val Ala Lys Gln Phe Ala His Ala Leu Ala
                500                 505                 510

Gly Cys Val Ser Gly Leu Val Gln Gly Lys Cys Lys Asp Gly Ala Ile
                515                 520                 525

Gly Ala Ala Val Gly Glu Ile Val Ala Glu Ser Ile Leu Gly Gly Arg
            530                 535                 540

Asn Pro Ala Thr Leu Ser Asp Ala Glu Lys His Lys Val Ile Ser Tyr
545                 550                 555                 560

Ser Lys Ile Ile Ala Gly Ser Val Ala Ala Leu Asn Gly Gly Asp Val
                565                 570                 575

Asn Thr Ala Ala Asn Ala Ala Glu Val Ala Val Asn Asn Ala Leu
            580                 585                 590

Asn Phe Asp Ser Thr Pro Thr Asn Ala Lys His Gln Pro Gln Lys
            595                 600                 605

Pro Asp Lys Thr Ala Leu Glu Lys Ile Ile Gln Ser Ile Met Pro Ala
610                 615                 620

His Ala Ala Gly Ala Met Thr Asn Pro Gln Asp Lys Asp Ala Ala Ile
625                 630                 635                 640

Trp Ile Ser Asn Ile Arg Asn Gly Ile Thr Gly Pro Ile Val Ile Thr
                    645                 650                 655

Ser Tyr Gly Val Tyr Ala Ala Gly Trp Thr Ala Pro Leu Ile Gly Thr
                660                 665                 670

Ala Gly Lys Ala Ala Ile Ser Thr Cys Met Ala Asn Pro Ser Gly Cys
                675                 680                 685

Thr Val Met Val Thr Gln Ala Ala Glu Ala Gly Ala Gly Ile Val Thr
            690                 695                 700

Gly Ala Val Thr Val Gly Asn Ala Trp Glu Ala Pro Val Gly Ala Leu
705                 710                 715                 720

Ser Lys Ala Lys Ala Ala Lys Gln Ala Ala Pro Lys Glu Thr Ile Asn
                    725                 730                 735

Asn Leu Ala Asn Leu Ala Lys Ala Glu Gln Gln Ile Leu Phe Arg Ile
                740                 745                 750

Ala Gln Arg Asp Thr Gln Leu Asp Ala Trp Lys Thr Gly Phe Asn Asn
            755                 760                 765

Arg Val Arg Lys Gly Ala Gly Leu Leu Asp Ala Ser Asn Ile Pro Ile
770                 775                 780

Thr Ile Asn Gly Lys Thr Ile Lys Pro Val Gln Ala Ile Ser Leu Lys
785                 790                 795                 800

Gly Ala Pro Val Tyr Ser Gly Val Ser Glu Gln Glu Ile Phe Ala Leu
                805                 810                 815

Tyr Arg Gln Met Thr Gly Gln Asn Pro Asn Phe Arg Val Leu Pro Asp
                820                 825                 830

Gly Arg Leu Ala Asn Gly Ile Ile Ser Thr Gly Glu Trp Ala Gly Thr
            835                 840                 845

Lys Ile Ala Leu Arg Asn Phe Ser Lys Thr Glu Asn Ser Thr Gln Ala
850                 855                 860

Arg Trp Thr Leu Asp Leu Gln Asn Pro Pro Ser Phe Ile Lys Gly Thr
865                 870                 875                 880

Lys Leu Glu Leu Lys Phe Gln
                    885
```

<210> SEQ ID NO 25
<211> LENGTH: 2385
<212> TYPE: DNA
<213> ORGANISM: Neisseria meningitidis

<400> SEQUENCE: 25

| | | | | | |
|---|---|---|---|---|---|
| ttgacactct | atgccgtaga | agagctcaac | tacgacaaac | tagacagcca | aaaaaggcgc | 60 |
| agatttctcg | gcatcagcta | cagcaaagca | cacgacacca | ccacccaagt | catgaaaacc | 120 |
| gcgctgccct | caagggtagt | tgcagaatca | gccaatctgc | aatcaggttg | ggataccaaa | 180 |
| ctgcaaggca | cacagtttga | aaccacactg | ggtggcgcaa | ccatacgcgc | aggcgtaggc | 240 |
| gagcaggcac | gggcagatgc | caagattatc | ctcgaaggga | tcaaaagcag | catccacaca | 300 |
| gaaaccgtga | gcagcagcaa | atctactcta | tggcaaaaac | aggcaggacg | gggcagtaac | 360 |
| atcgaaacct | tgcaattgcc | gagtttcacc | ggtcccgttg | cgcccgtact | gtccgcaccc | 420 |
| ggcggttaca | ttgtcgatat | tccccaaggc | aatctgaaaa | cccaaatcga | acccctcacc | 480 |
| aaacagcccg | agtatgctta | tttgaaacaa | cttcaagttg | cgaaaaacat | caactggaat | 540 |
| caggtgcagc | ttgcttacga | taatgggac | tacaaacagg | agggcttaac | cgaagcaggt | 600 |
| gcggcgatta | tcgcactggc | cgttaccgtg | gtcacctcag | gcgcaggaac | cggagccgta | 660 |
| ttgggattaa | acggtgcggc | cgccgccgca | accgatgcag | catttgcctc | tttggccagc | 720 |
| caggcttccg | tatcgttcat | caacaacaaa | ggcaatatcg | gtaacaccct | gaaagagctg | 780 |
| ggcagaagca | gcacggtgaa | aaatctggtg | gttgccgccg | ctaccgcagg | cgtagccgac | 840 |
| aaaatcggcg | cttcggcact | gaacaatgtc | agcgataagc | agtggatcaa | caacctgacc | 900 |
| gtcaacctag | ccaatgcggg | cagtgccgca | ctgattaata | ccgctgtcaa | cggcggcagc | 960 |
| ctgaaagaca | atctggaagc | gaatatcctt | gcggctttgg | tcaataccgc | gcatgggagaa | 1020 |
| gcagccagta | aaatcaaaca | gttggatcag | cactacatag | tccacaagat | tgcccatgcc | 1080 |
| atagcgggct | gtgcggcagc | ggcggcgaat | aagggtaagt | gtcaggatgg | tgcgatcggt | 1140 |
| gcggctgtgg | gcgagatagt | cggggaggct | ttgacaaacg | gcaaaatcc | tgccactttg | 1200 |
| acagctaaag | aacgcgaaca | gattttggca | tacagcaaac | tggttgccgg | tacggtaagc | 1260 |
| ggtgtggtcg | gcggcgatgt | gaatacagcg | gcgaatgcgg | ctaaagtcgc | gattgaaaat | 1320 |
| aacctattat | ctcaagaaga | gtatgctctt | agagaaaaat | tgatcaaaaa | agccaaaggg | 1380 |
| aaaggcctat | tatctttaga | ttggggcagc | ctgaccgaac | aagaggcaag | gcagtttatc | 1440 |
| tatttgattg | agaaagatcg | atattctaat | caattgcttg | accgatatca | aaaaaatcca | 1500 |
| agtagtttaa | ataatcaaga | aaaaaatatt | cttgcatatt | ttattaacca | aacctctgga | 1560 |
| ggtaacacag | cttgggcagc | ttcgatactg | aaaacgcccc | agtcaatggg | taatctcact | 1620 |
| attccttcca | agatattaa | taacaccta | tcgaaagcct | atcaaacatt | gagtcgttat | 1680 |
| gattcttttg | attacaaatc | agctgttgcc | gcacaacctg | cactttactt | attaaacgga | 1740 |
| ccgcttggct | tcagtgtcaa | agcagctact | gtggcagcag | gaggatataa | cattggacag | 1800 |
| ggagcgaaag | caatctctaa | tggagaatat | ctgcatggta | cagttcaggt | tgttaatggc | 1860 |
| acattgatgg | ttgcaggatc | tgtatctgca | caggctgcaa | tatcggccaa | gcctgcacct | 1920 |
| gttacccgtt | atctgagcaa | tgacagtgct | cctgctttaa | gacaagcttt | aactgctgaa | 1980 |
| agccagagaa | tccgcatgaa | actgccggaa | gagtatcgac | aaatagggaa | tcttgcgata | 2040 |
| gcaaaaattg | atgttaaagg | attaccgcaa | aggatggaag | catttagttc | tttccaaaaa | 2100 |
| ggggaacatg | gatttatttc | gttacctgaa | acaaaaattt | ttaaacctat | atctgttgat | 2160 |

-continued

```
aaatatcata atattgcctc tcctcctaga ggaacattaa gaaatataga tggagaatat   2220
aaattacttg aaactatagc acagcaactc ggaaataatc gtaatgtatc aggtagaatt   2280
gatctattta cagaattaaa ggcctgtcaa tcttgcagca atgttatttt agagtttaga   2340
aatcgctatc caaatattca attaaatatt tttacaggaa aatag                   2385
```

<210> SEQ ID NO 26
<211> LENGTH: 794
<212> TYPE: PRT
<213> ORGANISM: Neisseria meningitidis

<400> SEQUENCE: 26

```
Met Thr Leu Tyr Ala Val Glu Glu Leu Asn Tyr Asp Lys Leu Asp Ser
 1               5                  10                  15

Gln Lys Arg Arg Phe Leu Gly Ile Ser Tyr Ser Lys Ala His Asp
            20                  25                  30

Thr Thr Thr Gln Val Met Lys Thr Ala Leu Pro Ser Arg Val Val Ala
        35                  40                  45

Glu Ser Ala Asn Leu Gln Ser Gly Trp Asp Thr Lys Leu Gln Gly Thr
    50                  55                  60

Gln Phe Glu Thr Thr Leu Gly Gly Ala Thr Ile Arg Ala Gly Val Gly
65                  70                  75                  80

Glu Gln Ala Arg Ala Asp Ala Lys Ile Ile Leu Glu Gly Ile Lys Ser
                85                  90                  95

Ser Ile His Thr Glu Thr Val Ser Ser Lys Ser Thr Leu Trp Gln
            100                 105                 110

Lys Gln Ala Gly Arg Gly Ser Asn Ile Glu Thr Leu Gln Leu Pro Ser
        115                 120                 125

Phe Thr Gly Pro Val Ala Pro Val Leu Ser Ala Pro Gly Gly Tyr Ile
    130                 135                 140

Val Asp Ile Pro Gln Gly Asn Leu Lys Thr Gln Ile Glu Thr Leu Thr
145                 150                 155                 160

Lys Gln Pro Glu Tyr Ala Tyr Leu Lys Gln Leu Gln Val Ala Lys Asn
                165                 170                 175

Ile Asn Trp Asn Gln Val Gln Leu Ala Tyr Asp Lys Trp Asp Tyr Lys
            180                 185                 190

Gln Glu Gly Leu Thr Glu Ala Gly Ala Ile Ile Ala Leu Ala Val
        195                 200                 205

Thr Val Val Thr Ser Gly Ala Gly Thr Gly Ala Val Leu Gly Leu Asn
    210                 215                 220

Gly Ala Ala Ala Ala Thr Asp Ala Ala Phe Ala Ser Leu Ala Ser
225                 230                 235                 240

Gln Ala Ser Val Ser Phe Ile Asn Asn Lys Gly Asn Ile Gly Asn Thr
                245                 250                 255

Leu Lys Glu Leu Gly Arg Ser Ser Thr Val Lys Asn Leu Val Val Ala
            260                 265                 270

Ala Ala Thr Ala Gly Val Ala Asp Lys Ile Gly Ala Ser Ala Leu Asn
        275                 280                 285

Asn Val Ser Asp Lys Gln Trp Ile Asn Asn Leu Thr Val Asn Leu Ala
    290                 295                 300

Asn Ala Gly Ser Ala Ala Leu Ile Asn Thr Ala Val Asn Gly Gly Ser
305                 310                 315                 320

Leu Lys Asp Asn Leu Glu Ala Asn Ile Leu Ala Ala Leu Val Asn Thr
                325                 330                 335

Ala His Gly Glu Ala Ala Ser Lys Ile Lys Gln Leu Asp Gln His Tyr
```

```
                    340               345               350
Ile Val His Lys Ile Ala His Ala Ile Ala Gly Cys Ala Ala Ala
                355               360               365
Ala Asn Lys Gly Lys Cys Gln Asp Gly Ala Ile Gly Ala Ala Val Gly
            370               375               380
Glu Ile Val Gly Glu Ala Leu Thr Asn Gly Lys Asn Pro Ala Thr Leu
385               390               395               400
Thr Ala Lys Glu Arg Glu Gln Ile Leu Ala Tyr Ser Lys Leu Val Ala
                405               410               415
Gly Thr Val Ser Gly Val Val Gly Gly Asp Val Asn Thr Ala Ala Asn
                420               425               430
Ala Ala Lys Val Ala Ile Glu Asn Asn Leu Leu Ser Gln Glu Glu Tyr
            435               440               445
Ala Leu Arg Glu Lys Leu Ile Lys Ala Lys Gly Lys Gly Leu Leu
            450               455               460
Ser Leu Asp Trp Gly Ser Leu Thr Glu Gln Glu Ala Arg Gln Phe Ile
465               470               475               480
Tyr Leu Ile Glu Lys Asp Arg Tyr Ser Asn Gln Leu Leu Asp Arg Tyr
                485               490               495
Gln Lys Asn Pro Ser Ser Leu Asn Asn Gln Glu Lys Asn Ile Leu Ala
                500               505               510
Tyr Phe Ile Asn Gln Thr Ser Gly Gly Asn Thr Ala Trp Ala Ala Ser
                515               520               525
Ile Leu Lys Thr Pro Gln Ser Met Gly Asn Leu Thr Ile Pro Ser Lys
                530               535               540
Asp Ile Asn Asn Thr Leu Ser Lys Ala Tyr Gln Thr Leu Ser Arg Tyr
545               550               555               560
Asp Ser Phe Asp Tyr Lys Ser Ala Val Ala Ala Gln Pro Ala Leu Tyr
                565               570               575
Leu Leu Asn Gly Pro Leu Gly Phe Ser Val Lys Ala Ala Thr Val Ala
            580               585               590
Ala Gly Gly Tyr Asn Ile Gly Gln Gly Ala Lys Ala Ile Ser Asn Gly
            595               600               605
Glu Tyr Leu His Gly Thr Val Gln Val Val Asn Gly Thr Leu Met Val
            610               615               620
Ala Gly Ser Val Ser Ala Gln Ala Ile Ser Ala Lys Pro Ala Pro
625               630               635               640
Val Thr Arg Tyr Leu Ser Asn Asp Ser Ala Pro Ala Leu Arg Gln Ala
                645               650               655
Leu Thr Ala Glu Ser Gln Arg Ile Arg Met Lys Leu Pro Glu Glu Tyr
            660               665               670
Arg Gln Ile Gly Asn Leu Ala Ile Ala Lys Ile Asp Val Lys Gly Leu
            675               680               685
Pro Gln Arg Met Glu Ala Phe Ser Ser Phe Gln Lys Gly Glu His Gly
            690               695               700
Phe Ile Ser Leu Pro Glu Thr Lys Ile Phe Lys Pro Ile Ser Val Asp
705               710               715               720
Lys Tyr His Asn Ile Ala Ser Pro Pro Arg Gly Thr Leu Arg Asn Ile
                725               730               735
Asp Gly Glu Tyr Lys Leu Leu Glu Thr Ile Ala Gln Leu Gly Asn
            740               745               750
Asn Arg Asn Val Ser Gly Arg Ile Asp Leu Phe Thr Glu Leu Lys Ala
            755               760               765
```

Cys Gln Ser Cys Ser Asn Val Ile Leu Glu Phe Arg Asn Arg Tyr Pro
770                 775                 780

Asn Ile Gln Leu Asn Ile Phe Thr Gly Lys
785                 790

<210> SEQ ID NO 27
<211> LENGTH: 621
<212> TYPE: DNA
<213> ORGANISM: Neisseria meningitidis

<400> SEQUENCE: 27
ttgctgggtg tggttccggg tatcggtgaa tcgatacagg cctataaagt agcgaaagcg      60
gcaaaaaatt tacaaggcat gaaaaagcc ttggacaagg cagcaaccgt tgccactgca     120
cagggctatg tcagtaaaac caaaatcaaa atcggtcaaa ctgaattaag ggttactgca     180
gcaactgaca acaattgct gaaagctatt ggcgaaggaa gggacacgac aggtaaaatg      240
accgagcagt tatttgactc tttagctaaa caaaatggct tcagagtgct tcgggcggc      300 aaatacggcg gaaataacgg ttttgatcat gtatggcagg ctgccgatgg tagtgtcgtt     360
ttgattgtag aaagtaagca gattaggaac ggtacggtac agctgaatcc gaatggtgcg     420
ggtggatata cgcaaatgag tgaggattgg attagacaag ttttagatca attacccgat     480
ggtagtcccg ctaaagctgc tgtcttcaaa gcaataaga acggcacatt aaaaacagca     540
atagcaggcg ttgatcgtca aacaggtaag gccgttattc ttcctgtcaa agttccttct     600
aaaaccaata taaggagata a                                               621

<210> SEQ ID NO 28
<211> LENGTH: 206
<212> TYPE: PRT
<213> ORGANISM: Neisseria meningitidis

<400> SEQUENCE: 28

Met Leu Gly Val Val Pro Gly Ile Gly Glu Ser Ile Gln Ala Tyr Lys
1               5                   10                  15

Val Ala Lys Ala Ala Lys Asn Leu Gln Gly Met Lys Lys Ala Leu Asp
            20                  25                  30

Lys Ala Thr Val Ala Thr Ala Gln Gly Tyr Val Ser Lys Thr Lys
        35                  40                  45

Ile Lys Ile Gly Gln Thr Glu Leu Arg Val Thr Ala Ala Thr Asp Lys
    50                  55                  60

Gln Leu Leu Lys Ala Ile Gly Glu Gly Arg Asp Thr Thr Gly Lys Met
65                  70                  75                  80

Thr Glu Gln Leu Phe Asp Ser Leu Ala Lys Gln Asn Gly Phe Arg Val
                85                  90                  95

Leu Ser Gly Gly Lys Tyr Gly Gly Asn Asn Gly Phe Asp His Val Trp
            100                 105                 110

Gln Ala Ala Asp Gly Ser Val Val Leu Ile Val Glu Ser Lys Gln Ile
        115                 120                 125

Arg Asn Gly Thr Val Gln Leu Asn Pro Asn Gly Ala Gly Gly Tyr Thr
    130                 135                 140

Gln Met Ser Glu Asp Trp Ile Arg Gln Val Leu Asp Gln Leu Pro Asp
145                 150                 155                 160

Gly Ser Pro Ala Lys Ala Ala Val Phe Lys Ala Asn Lys Asn Gly Thr
                165                 170                 175

Leu Lys Thr Ala Ile Ala Gly Val Asp Arg Gln Thr Gly Lys Ala Val
            180                 185                 190

Ile Leu Pro Val Lys Val Pro Ser Lys Thr Asn Ile Arg Arg
    195                 200                 205

<210> SEQ ID NO 29
<211> LENGTH: 4509
<212> TYPE: DNA
<213> ORGANISM: Neisseria meningitidis

<400> SEQUENCE: 29

| | | | | | |
|---|---|---|---|---|---|
| atgaatgagg | gtgaagttgt | tttaacacca | gaacaaatcc | aaaccttgcg | tggttatgct | 60 |
| ttccgtggcg | ataccatgg | cggttggcgt | tatttggcta | atttgggtga | ccgttatgcg | 120 |
| gatgatgctg | ctgcaattgt | cggtaaggat | gcaaacttaa | atggtttgaa | tttatggatg | 180 |
| aaaaaaggtg | tggaaaacct | atgggatgat | acggtcggta | aaaagacccg | tttagagaaa | 240 |
| tttgatcggg | ttgcattgca | acatttcagc | caatatgtag | atctaattaa | tgaaaataat | 300 |
| ggtagattac | ctaacactag | tgaaattgag | agaagttact | ataaagccgt | taccgaaaat | 360 |
| ggtgtttctt | ctagtgcagc | tattgattta | gttattaatc | gctcacttcc | ggatatggca | 420 |
| gatggttatt | gggcattagg | tttggggata | gaagccgaac | gtatccacaa | tgcgcaagca | 480 |
| gtaaataatc | cgaacggtag | cgaatgggat | aatagaaagc | agttaatatc | tgctttagat | 540 |
| aaaggatttg | atggatcttt | taaagagaag | cattttactt | ttttacaatc | tgtgataatg | 600 |
| gatgtaacaa | agttaggtgt | tgaatataca | atagatggt | ggcaaaaaat | tggaggttgg | 660 |
| ggtaatggga | taatcaatga | tttatataaa | agtgttgcaa | aaagagagtg | gactggaata | 720 |
| tttgagatcg | ttaataataa | catcaagcaa | tttagagatc | tgttcccaaa | tccggaaggc | 780 |
| tggatcgatg | atggtcacca | atgtttcgct | ccttgggtta | agaaactaa | aaaacgcaat | 840 |
| ggcaaatatc | atgtctacga | ccccctcgcc | ctagatttgg | acgagacgg | tatagaaacc | 900 |
| gttgccacca | aaggctttgc | aggcagctta | tttgatcaca | ccaacaacgg | tatccgcacc | 960 |
| gccaccggtt | gggtttctgc | cgatgacggt | ttactcgtcc | gcgatttgaa | cggcaacggc | 1020 |
| atcatcgaca | acggtgcgga | actcttcggc | gacaacacca | aactggcaga | cggttctttt | 1080 |
| gccaaacacg | gctatgcagc | tttggccgaa | ttggattcaa | acggcgacaa | catcatcaac | 1140 |
| gcggcagacg | ccgcattcca | aaccctgcgt | gtatggcagg | atctcaatca | ggacggcatt | 1200 |
| tcccaaacca | cgaactccg | caccccttgaa | gaattgggta | ttcaatcttt | ggatctcgcc | 1260 |
| tataaagatg | taaataaaaa | tctcggtaac | ggtaacactt | tggctcagca | aggtagctac | 1320 |
| accaaaacaa | acggtacaac | cgcaaaaatg | ggggatttac | ttttagcagc | cgacaatctg | 1380 |
| cacagccgct | tcaaagacaa | agtggaactc | actgccaaac | aggcaaaagc | cgccaatctt | 1440 |
| gcgggcattg | gtcgtctgcg | cgatttgcgc | gaagctgccg | cattgtccgg | cgatttggcc | 1500 |
| aatatgctga | agcttattc | tgccgccgaa | actaaagaag | cacagttggc | attgttagat | 1560 |
| aatttgattc | acaaatgggc | ggaaaccgat | tcgaactggg | gcaaaaaatc | gccaatgcga | 1620 |
| ctttcaaccg | attggacgca | aacggctaat | gaaggtattg | cactgacacc | atcccaagta | 1680 |
| gcacaactaa | aaaagaacgc | tttagttttcc | cttctgata | aagctaaagc | agctattgac | 1740 |
| gccgcccgcg | accgcattgc | cgtgcttgat | gcctacacgg | ggcaggattc | cagcacactc | 1800 |
| tattacatga | gcgaagaaga | cgcgcttaat | atcgtcaaag | taaccaacga | tacatacgac | 1860 |
| catctcgcca | aaaacatcta | ccaaaacctg | ttgttccaaa | cccgtttgca | gccatatttg | 1920 |
| aatcaaatca | gtttccaaaat | ggaaaatgat | acgttcactt | tggattttag | tggtcttgtt | 1980 |
| caagcattta | accatgtcaa | agaaactaat | ccgcaaaaag | cttttgtgga | tttggccgag | 2040 |
| atgcttgcat | atggcgaact | tcgttcttgg | tatgaaggcc | gaagactaat | ggccgattat | 2100 |

```
gtggaggagg caaaaaaagc aggtaaattt gaagattacc agaaagtgtt gggtcaggag    2160
accgttgcat tattagctaa acatcgggt acgcaagcag atgatatcct gcaaaatgta    2220
ggctttggtc ataataaaaa tgtttcttta tatggtaatg acggcaacga cactctgatc    2280
ggcggtgccg gtaatgatta cttggagggc ggcagcggtt cggatactta tgtcttcggc    2340
aaaggcttcg gtcaggatac ggtctataat tacgactacg ctaccggacg caaagacatc    2400
atccgcttta ccgacggtat tacagccgat atgctgactt ttacccgaga gggcaaccat    2460
cttcttatca aggcaaaaga cggcagtgga caagtgactg ttcagtacta tttccagaac    2520
gatggctcag gagcttaccg tatcgacgag attcatttcg ataacggcaa agtactggat    2580
gttgccactg tcaaagaact ggtacagcaa tccaccgacg gctcggacag attgtatgcc    2640
taccaatccg gaaataccct aaatggcgga ttgggcgatg actatctgta cggtgccgac    2700
ggggatgacc tgctgaatgg tgatgcaggc aacgacagta tctacagtgg caatggcaat    2760
gatacgctcg atggaggaga aggcaacgac gccctgtacg gctataatgg taacgatgta    2820
ctgaatggtg gcgaaggcaa tgatcatttg aacggcgaag acggtaacga cactctgatc    2880
ggcggtgccg gtaatgatta cttggagggc ggcagcggtt cggatactta tgtcttcggc    2940
aaaggcttcg gtcaggatac ggtctataat tacgactacg ctaccggacg caaagacatc    3000
atccgcttta ccgacggtat tacagccgat atgctgactt ttacccgaga gggcaaccat    3060
cttcttatca aggcaaaaga cggcagtgga caagtgactg ttcagtccta tttccagaac    3120
gatggctcag gtgcttaccg tatcgatgag attcatttcg ataacggcaa agtactggat    3180
gttgccactg tcaaagaact ggtacagcaa tccaccgacg gctcggacag attgtatgcc    3240
taccaatccg gaaataccct aaatggcgga ttgggcgatg actatctgta cggtgccgac    3300
ggggatgacc tgctgaatgg tgatgcaggc aacgacagta tctacagtgg caatggcaat    3360
gatacgctcg atggaggaga aggcaacgac gccctgtacg gctataatgg taacgatgta    3420
ctgaatggtg gcgaaggcaa tgatcatttg aacggcgaag acggtaacga cactctgatc    3480
ggcggtgcag gcaatgatta cttggagggc ggcagcggtt cggatactta tgtcttcggc    3540
gaaggcttcg gtcaggatac ggtctataat tacgactacg ctaccggacg caaagacatc    3600
atccgcttta ccgacggtat tacagccgat atgctgactt ttacccgaga gggcaaccat    3660
cttcttatca aggcaaaaga cggcagtgga caagtgactg ttcagtccta tttccagaac    3720
gatggctcag gtgcttaccg tatcgatgag attcatttcg ataacggcaa agtactggat    3780
gttgccactg tcaaagaact ggtacagcaa tccaccgacg gctcggacag attgtatgcc    3840
taccaatccg gaaataccct aaatggcgga ttgggcgatg actatctgta cggtgccgac    3900
ggggatgacc tgctgaatgg tgatgcaggc aacgacagta tctacagtgg caatggcaat    3960
gatacgctcg atggaggaga aggcaacgac gccctgtacg gctataatgg taacgatgta    4020
ctgaatggtg gcgaaggcaa tgatcatttg aacggcgaag acggtaacga cactctgatc    4080
ggcggtgccg gtaatgatta cttggagggc ggcagcggtt cggatactta tgtcttcggc    4140
aaaggcttcg gtcaggatac ggtctataat taccatgtgg ataaaaactc tgacactatg    4200
cactttaaag gatttaaagc agcagatgtt cattttatcc gttccggaag tgatttggtg    4260
cttagcgctt ctgaacaaga caacgtacgt atttccggat tcttctatgg tgaaaaccat    4320
cgtgtagata catttgtctt tgatgatgca gctatcagta atccagattt tgccaagtat    4380
attaatgctg gcaataattt ggtacagtct atgtctgtgt tcggttctaa tactgctgcg    4440
acaggaggaa atgtggatgc caatacacaa tccgtacagc agccgttatt ggtaacgcca    4500
``` tctgcataa                                                         4509

<210> SEQ ID NO 30
<211> LENGTH: 1502
<212> TYPE: PRT
<213> ORGANISM: Neisseria meningitidis

<400> SEQUENCE: 30

Met Asn Glu Gly Glu Val Val Leu Thr Pro Glu Gln Ile Gln Thr Leu
 1               5                  10                  15

Arg Gly Tyr Ala Phe Arg Gly Asp Thr Tyr Gly Gly Trp Arg Tyr Leu
            20                  25                  30

Ala Asn Leu Gly Asp Arg Tyr Ala Asp Asp Ala Ala Ile Val Gly
        35                  40                  45

Lys Asp Ala Asn Leu Asn Gly Leu Asn Leu Trp Met Lys Lys Gly Val
    50                  55                  60

Glu Asn Leu Trp Asp Asp Thr Val Gly Lys Lys Thr Arg Leu Glu Lys
65                  70                  75                  80

Phe Asp Arg Val Ala Leu Gln His Phe Ser Gln Tyr Val Asp Leu Ile
                85                  90                  95

Asn Glu Asn Asn Gly Arg Leu Pro Asn Thr Ser Glu Ile Glu Arg Ser
            100                 105                 110

Tyr Tyr Lys Ala Val Thr Glu Asn Gly Val Ser Ser Ala Ala Ile
        115                 120                 125

Asp Leu Val Ile Asn Arg Ser Leu Pro Asp Met Ala Asp Gly Tyr Trp
    130                 135                 140

Ala Leu Gly Leu Gly Ile Glu Ala Glu Arg Ile His Asn Ala Gln Ala
145                 150                 155                 160

Val Asn Asn Pro Asn Gly Ser Glu Trp Asp Asn Arg Lys Gln Leu Ile
                165                 170                 175

Ser Ala Leu Asp Lys Gly Phe Asp Gly Ser Phe Lys Glu Lys His Phe
            180                 185                 190

Thr Phe Leu Gln Ser Val Ile Met Asp Val Thr Lys Leu Gly Val Glu
        195                 200                 205

Tyr Thr Ile Asp Gly Trp Gln Lys Ile Gly Gly Trp Gly Asn Gly Ile
    210                 215                 220

Ile Asn Asp Leu Tyr Lys Ser Val Ala Lys Arg Glu Trp Thr Gly Ile
225                 230                 235                 240

Phe Glu Ile Val Asn Asn Asn Ile Lys Gln Phe Arg Asp Leu Phe Pro
                245                 250                 255

Asn Pro Glu Gly Trp Ile Asp Asp Gly His Gln Cys Phe Ala Pro Trp
            260                 265                 270

Val Lys Glu Thr Lys Lys Arg Asn Gly Lys Tyr His Val Tyr Asp Pro
        275                 280                 285

Leu Ala Leu Asp Leu Asp Gly Gly Ile Glu Thr Val Ala Thr Lys
    290                 295                 300

Gly Phe Ala Gly Ser Leu Phe Asp His Thr Asn Asn Gly Ile Arg Thr
305                 310                 315                 320

Ala Thr Gly Trp Val Ser Ala Asp Gly Leu Leu Val Arg Asp Leu
                325                 330                 335

Asn Gly Asn Gly Ile Ile Asp Asn Gly Ala Glu Leu Phe Gly Asp Asn
            340                 345                 350

Thr Lys Leu Ala Asp Gly Ser Phe Ala Lys His Gly Tyr Ala Ala Leu
        355                 360                 365

```
Ala Glu Leu Asp Ser Asn Gly Asp Asn Ile Ile Asn Ala Ala Asp Ala
370                 375                 380

Ala Phe Gln Thr Leu Arg Val Trp Gln Asp Leu Asn Gln Asp Gly Ile
385                 390                 395                 400

Ser Gln Thr Asn Glu Leu Arg Thr Leu Glu Glu Leu Gly Ile Gln Ser
                405                 410                 415

Leu Asp Leu Ala Tyr Lys Asp Val Asn Lys Asn Leu Gly Asn Gly Asn
            420                 425                 430

Thr Leu Ala Gln Gln Gly Ser Tyr Thr Lys Thr Asn Gly Thr Thr Ala
        435                 440                 445

Lys Met Gly Asp Leu Leu Ala Ala Asp Asn Leu His Ser Arg Phe
450                 455                 460

Lys Asp Lys Val Glu Leu Thr Ala Lys Gln Ala Lys Ala Ala Asn Leu
465                 470                 475                 480

Ala Gly Ile Gly Arg Leu Arg Asp Leu Arg Glu Ala Ala Leu Ser
                485                 490                 495

Gly Asp Leu Ala Asn Met Leu Lys Ala Tyr Ser Ala Ala Glu Thr Lys
            500                 505                 510

Glu Ala Gln Leu Ala Leu Leu Asp Asn Leu Ile His Lys Trp Ala Glu
        515                 520                 525

Thr Asp Ser Asn Trp Gly Lys Lys Ser Pro Met Arg Leu Ser Thr Asp
    530                 535                 540

Trp Thr Gln Thr Ala Asn Glu Gly Ile Ala Leu Thr Pro Ser Gln Val
545                 550                 555                 560

Ala Gln Leu Lys Lys Asn Ala Leu Val Ser Leu Ser Asp Lys Ala Lys
                565                 570                 575

Ala Ala Ile Asp Ala Ala Arg Asp Arg Ile Ala Val Leu Asp Ala Tyr
            580                 585                 590

Thr Gly Gln Asp Ser Ser Thr Leu Tyr Tyr Met Ser Glu Glu Asp Ala
        595                 600                 605

Leu Asn Ile Val Lys Val Thr Asn Asp Thr Tyr Asp His Leu Ala Lys
    610                 615                 620

Asn Ile Tyr Gln Asn Leu Leu Phe Gln Thr Arg Leu Gln Pro Tyr Leu
625                 630                 635                 640

Asn Gln Ile Ser Phe Lys Met Glu Asn Asp Thr Phe Thr Leu Asp Phe
                645                 650                 655

Ser Gly Leu Val Gln Ala Phe Asn His Val Lys Glu Thr Asn Pro Gln
            660                 665                 670

Lys Ala Phe Val Asp Leu Ala Glu Met Leu Ala Tyr Gly Glu Leu Arg
        675                 680                 685

Ser Trp Tyr Glu Gly Arg Arg Leu Met Ala Asp Tyr Val Glu Glu Ala
    690                 695                 700

Lys Lys Ala Gly Lys Phe Glu Asp Tyr Gln Lys Val Leu Gly Gln Glu
705                 710                 715                 720

Thr Val Ala Leu Leu Ala Lys Thr Ser Gly Thr Gln Ala Asp Asp Ile
                725                 730                 735

Leu Gln Asn Val Gly Phe Gly His Asn Lys Asn Val Ser Leu Tyr Gly
            740                 745                 750

Asn Asp Gly Asn Asp Thr Leu Ile Gly Gly Ala Gly Asn Asp Tyr Leu
        755                 760                 765

Glu Gly Gly Ser Gly Ser Asp Thr Tyr Val Phe Gly Lys Gly Phe Gly
    770                 775                 780

Gln Asp Thr Val Tyr Asn Tyr Asp Tyr Ala Thr Gly Arg Lys Asp Ile
785                 790                 795                 800
```

```
Ile Arg Phe Thr Asp Gly Ile Thr Ala Asp Met Leu Thr Phe Thr Arg
            805                 810                 815

Glu Gly Asn His Leu Leu Ile Lys Ala Lys Asp Gly Ser Gly Gln Val
            820                 825                 830

Thr Val Gln Tyr Tyr Phe Gln Asn Asp Gly Ser Gly Ala Tyr Arg Ile
            835                 840                 845

Asp Glu Ile His Phe Asp Asn Gly Lys Val Leu Asp Val Ala Thr Val
            850                 855                 860

Lys Glu Leu Val Gln Gln Ser Thr Asp Gly Ser Asp Arg Leu Tyr Ala
865                 870                 875                 880

Tyr Gln Ser Gly Asn Thr Leu Asn Gly Gly Leu Gly Asp Asp Tyr Leu
                    885                 890                 895

Tyr Gly Ala Asp Gly Asp Asp Leu Leu Asn Gly Asp Ala Gly Asn Asp
                900                 905                 910

Ser Ile Tyr Ser Gly Asn Gly Asn Asp Thr Leu Asp Gly Gly Glu Gly
                915                 920                 925

Asn Asp Ala Leu Tyr Gly Tyr Asn Gly Asn Asp Val Leu Asn Gly Gly
930                 935                 940

Glu Gly Asn Asp His Leu Asn Gly Glu Asp Gly Asn Asp Thr Leu Ile
945                 950                 955                 960

Gly Gly Ala Gly Asn Asp Tyr Leu Glu Gly Gly Ser Gly Ser Asp Thr
                965                 970                 975

Tyr Val Phe Gly Lys Gly Phe Gly Gln Asp Thr Val Tyr Asn Tyr Asp
                980                 985                 990

Tyr Ala Thr Gly Arg Lys Asp Ile Ile Arg Phe Thr Asp Gly Ile Thr
            995                 1000                1005

Ala Asp Met Leu Thr Phe Thr Arg Glu Gly Asn His Leu Leu Ile Lys
            1010                1015                1020

Ala Lys Asp Gly Ser Gly Gln Val Thr Val Gln Ser Tyr Phe Gln Asn
1025                1030                1035                1040

Asp Gly Ser Gly Ala Tyr Arg Ile Asp Glu Ile His Phe Asp Asn Gly
            1045                1050                1055

Lys Val Leu Asp Val Ala Thr Val Lys Glu Leu Val Gln Gln Ser Thr
            1060                1065                1070

Asp Gly Ser Asp Arg Leu Tyr Ala Tyr Gln Ser Gly Asn Thr Leu Asn
            1075                1080                1085

Gly Gly Leu Gly Asp Asp Tyr Leu Tyr Gly Ala Asp Gly Asp Asp Leu
            1090                1095                1100

Leu Asn Gly Asp Ala Gly Asn Asp Ser Ile Tyr Ser Gly Asn Gly Asn
1105                1110                1115                1120

Asp Thr Leu Asp Gly Gly Glu Gly Asn Asp Ala Leu Tyr Gly Tyr Asn
            1125                1130                1135

Gly Asn Asp Val Leu Asn Gly Gly Glu Gly Asn Asp His Leu Asn Gly
            1140                1145                1150

Glu Asp Gly Asn Asp Thr Leu Ile Gly Gly Ala Gly Asn Asp Tyr Leu
            1155                1160                1165

Glu Gly Gly Ser Gly Ser Asp Thr Tyr Val Phe Gly Glu Gly Phe Gly
            1170                1175                1180

Gln Asp Thr Val Tyr Asn Tyr Asp Tyr Ala Thr Gly Arg Lys Asp Ile
1185                1190                1195                1200

Ile Arg Phe Thr Asp Gly Ile Thr Ala Asp Met Leu Thr Phe Thr Arg
            1205                1210                1215

Glu Gly Asn His Leu Leu Ile Lys Ala Lys Asp Gly Ser Gly Gln Val
```

| | | | | | | | 1220 | | | | | 1225 | | | | | 1230 | | |
|---|---|---|---|---|---|---|---|---|---|---|---|---|---|---|---|---|---|---|---|
Thr Val Gln Ser Tyr Phe Gln Asn Asp Gly Ser Gly Ala Tyr Arg Ile
                    1235                      1240                1245

Asp Glu Ile His Phe Asp Asn Gly Lys Val Leu Asp Val Ala Thr Val
    1250                    1255                    1260

Lys Glu Leu Val Gln Gln Ser Thr Asp Gly Ser Asp Arg Leu Tyr Ala
1265                    1270                    1275                  1280

Tyr Gln Ser Gly Asn Thr Leu Asn Gly Leu Gly Asp Asp Tyr Leu
                    1285                    1290                    1295

Tyr Gly Ala Asp Gly Asp Asp Leu Leu Asn Gly Asp Ala Gly Asn Asp
            1300                    1305                    1310

Ser Ile Tyr Ser Gly Asn Gly Asn Asp Thr Leu Asp Gly Gly Glu Gly
                    1315                    1320                    1325

Asn Asp Ala Leu Tyr Gly Tyr Asn Gly Asn Asp Val Leu Asn Gly Gly
1330                    1335                    1340

Glu Gly Asn Asp His Leu Asn Gly Glu Asp Gly Asn Asp Thr Leu Ile
1345                    1350                    1355                  1360

Gly Gly Ala Gly Asn Asp Tyr Leu Glu Gly Gly Ser Gly Ser Asp Thr
            1365                    1370                    1375

Tyr Val Phe Gly Lys Gly Phe Gly Gln Asp Thr Val Tyr Asn Tyr His
                    1380                    1385                    1390

Val Asp Lys Asn Ser Asp Thr Met His Phe Lys Gly Phe Lys Ala Ala
            1395                    1400                    1405

Asp Val His Phe Ile Arg Ser Gly Ser Asp Leu Val Leu Ser Ala Ser
                    1410                    1415                    1420

Glu Gln Asp Asn Val Arg Ile Ser Gly Phe Phe Tyr Gly Glu Asn His
1425                    1430                    1435                  1440

Arg Val Asp Thr Phe Val Phe Asp Ala Ala Ile Ser Asn Pro Asp
            1445                    1450                    1455

Phe Ala Lys Tyr Ile Asn Ala Gly Asn Asn Leu Val Gln Ser Met Ser
                    1460                    1465                    1470

Val Phe Gly Ser Asn Thr Ala Ala Thr Gly Gly Asn Val Asp Ala Asn
            1475                    1480                    1485

Thr Gln Ser Val Gln Gln Pro Leu Leu Val Thr Pro Ser Ala
    1490                    1495                    1500

<210> SEQ ID NO 31
<211> LENGTH: 774
<212> TYPE: DNA
<213> ORGANISM: Neisseria meningitidis

<400> SEQUENCE: 31
atgaacgcca ttgcagacgt gcaatccagc cgcgatttac gcaacctgcc gattaatcag    60
gtcggcatca agacctgcg cttttccaatc tcccttaaaa gcaaagaagg cgaacaatcc   120
accgtcgccc acctgaccat gacggttttc ctgcctgccg accaaaaagg cacgcatatg   180
tcgcgctttg tcgccctgat ggaaaaacaa accgaagcct tggatttcga tacgctgcac   240
aaactgaccg tcgatatggt tgccctgttg gattcgcatt ccggaaaaat cagcgtttgc   300
ttcccgtttt tccgcaagaa aagtgcgccc gtctccggca tccaatcgct gcttgactat   360
gatgttaccc tgaccggcga aatcaaaaac ggtacataca gccacaatct gaaagtaatg   420
gttccggtta cttcattgtg tccgtgttcc aaagaaattt cccaatacgg cgcacacaac   480
caacgttcgc atgtgactgt cagcctgatt gcaaacgcgg atgtaggtat tgaagaaatc   540
atcgattacg ttgaagcgca agcaagctgc caactctacg gtttgctcaa acgcccgat   600

```
gaaaaatatg ttaccgaaaa agcctacgaa aacccgaaat tcgtggaaga tatggtgcgt      660
gatgtcgcta cttcgctgat cgccgacaaa cgcatcaaga gtttcgttgt cgagagcgag      720
aatttcgagt ctatccacaa ccattcggct tatgcctata tcgcctaccc gtag            774
```

<210> SEQ ID NO 32
<211> LENGTH: 257
<212> TYPE: PRT
<213> ORGANISM: Neisseria meningitidis

<400> SEQUENCE: 32

```
Met Asn Ala Ile Ala Asp Val Gln Ser Ser Arg Asp Leu Arg Asn Leu
 1               5                  10                  15

Pro Ile Asn Gln Val Gly Ile Lys Asp Leu Arg Phe Pro Ile Ser Leu
            20                  25                  30

Lys Ser Lys Glu Gly Glu Gln Ser Thr Val Ala His Leu Thr Met Thr
        35                  40                  45

Val Phe Leu Pro Ala Asp Gln Lys Gly Thr His Met Ser Arg Phe Val
    50                  55                  60

Ala Leu Met Glu Lys Gln Thr Glu Ala Leu Asp Phe Asp Thr Leu His
65                  70                  75                  80

Lys Leu Thr Val Asp Met Val Ala Leu Leu Asp Ser His Ser Gly Lys
                85                  90                  95

Ile Ser Val Cys Phe Pro Phe Phe Arg Lys Lys Ser Ala Pro Val Ser
            100                 105                 110

Gly Ile Gln Ser Leu Leu Asp Tyr Asp Val Thr Leu Thr Gly Glu Ile
        115                 120                 125

Lys Asn Gly Thr Tyr Ser His Asn Leu Lys Val Met Val Pro Val Thr
    130                 135                 140

Ser Leu Cys Pro Cys Ser Lys Glu Ile Ser Gln Tyr Gly Ala His Asn
145                 150                 155                 160

Gln Arg Ser His Val Thr Val Ser Leu Ile Ala Asn Ala Asp Val Gly
                165                 170                 175

Ile Glu Glu Ile Ile Asp Tyr Val Glu Ala Gln Ala Ser Cys Gln Leu
            180                 185                 190

Tyr Gly Leu Leu Lys Arg Pro Asp Glu Lys Tyr Val Thr Glu Lys Ala
        195                 200                 205

Tyr Glu Asn Pro Lys Phe Val Glu Asp Met Val Arg Asp Val Ala Thr
    210                 215                 220

Ser Leu Ile Ala Asp Lys Arg Ile Lys Ser Phe Val Val Glu Ser Glu
225                 230                 235                 240

Asn Phe Glu Ser Ile His Asn His Ser Ala Tyr Ala Tyr Ile Ala Tyr
                245                 250                 255

Pro
```

<210> SEQ ID NO 33
<211> LENGTH: 714
<212> TYPE: DNA
<213> ORGANISM: Neisseria meningitidis

<400> SEQUENCE: 33

```
atgttgttcc gtaaaacgac cgccgccgtt ttggcggcaa ccttgatgct gaatggctgt       60
acggcaatga tgtggggcat gaacgacccg ttcagccaaa cgaccgccta taaacacgtt      120
gacaaagacc aaatccgcgc cttcggtgtg gttgccaaag acaatgccca attggaaaag      180
ggcagcctgg tgatgatggg cgggaaatac tggttcgtcg tcaatcctga agattcggcg      240
```

| aagctgacgg gcattttgaa ggccgggttg gacaagcagt ttcaaatggt tgagcccaac | 300 |
| cgcgctttg cctaccaagc cctgccggtc aaactcgaat cgcccgccag ccagaatttc | 360 |
| agtaccgacg acctttgcct gcgctacgat accgacagac ctgccgacat cgccaagctg | 420 |
| aaacagcttg agtttgaagc ggtcgaactc gacaatcgga ccatttacac gcgctgcgtc | 480 |
| tccgccaaag gcaaatacta cgccacaccg caaaaactga cgccgatta tcattttgag | 540 |
| caaagtgtgc ctgccgatat ttattacacg gttacgaaaa acataccga caaatccaag | 600 |
| ttgtttgaaa atattgcata tacgcccacc acgttgatac tggatgcggc gggtgcggta | 660 |
| ctggtcttgc ctatggcggc gttgattgca gccgcgaatt cctcagacaa atga | 714 |

<210> SEQ ID NO 34
<211> LENGTH: 237
<212> TYPE: PRT
<213> ORGANISM: Neisseria meningitidis

<400> SEQUENCE: 34

Met Leu Phe Arg Lys Thr Thr Ala Ala Val Leu Ala Ala Thr Leu Met
1               5                   10                  15

Leu Asn Gly Cys Thr Ala Met Met Trp Gly Met Asn Asp Pro Phe Ser
            20                  25                  30

Gln Thr Thr Ala Tyr Lys His Val Asp Lys Asp Gln Ile Arg Ala Phe
        35                  40                  45

Gly Val Val Ala Lys Asp Asn Ala Gln Leu Glu Lys Gly Ser Leu Val
    50                  55                  60

Met Met Gly Gly Lys Tyr Trp Phe Val Val Asn Pro Glu Asp Ser Ala
65                  70                  75                  80

Lys Leu Thr Gly Ile Leu Lys Ala Gly Leu Asp Lys Gln Phe Gln Met
                85                  90                  95

Val Glu Pro Asn Pro Arg Phe Ala Tyr Gln Ala Leu Pro Val Lys Leu
            100                 105                 110

Glu Ser Pro Ala Ser Gln Asn Phe Ser Thr Asp Asp Leu Cys Leu Arg
        115                 120                 125

Tyr Asp Thr Asp Arg Pro Ala Asp Ile Ala Lys Leu Lys Gln Leu Glu
    130                 135                 140

Phe Glu Ala Val Glu Leu Asp Asn Arg Thr Ile Tyr Thr Arg Cys Val
145                 150                 155                 160

Ser Ala Lys Gly Lys Tyr Tyr Ala Thr Pro Gln Lys Leu Asn Ala Asp
                165                 170                 175

Tyr His Phe Glu Gln Ser Val Pro Ala Asp Ile Tyr Tyr Thr Val Thr
            180                 185                 190

Lys Lys His Thr Asp Lys Ser Lys Leu Phe Glu Asn Ile Ala Tyr Thr
        195                 200                 205

Pro Thr Thr Leu Ile Leu Asp Ala Ala Gly Ala Val Leu Val Leu Pro
    210                 215                 220

Met Ala Ala Leu Ile Ala Ala Ala Asn Ser Ser Asp Lys
225                 230                 235

<210> SEQ ID NO 35
<211> LENGTH: 1209
<212> TYPE: DNA
<213> ORGANISM: Neisseria meningitidis

<400> SEQUENCE: 35

| atgtccgaac cgttgcacgt cctcgtcatc ccctcatggt atccgcaatc cgaacaggat | 60 |

-continued

```
gtggacggga ttttttttca aaatcaggca ctggcattgc agagaaaagg catcaaaact    120
gccgtgcttg caccgatgtt ccgctacttg cggaaagaaa cagcaagcat cctgaccggt    180
ccttacggtt ttgcccaata ccggcaaaaa ggtttggaca tctatgcatg gcacggcatg    240
tatttcttcc cccgttttcc gctaatcgac atcgaccgca tccgctgggt gcgggcagga    300
ttaaaggcct ttgagcgcta tcggggaa acggcattc ccgacatcat ccatgcccac    360
tgtatgaact atgccggcat acttgccttc aagatttccc aaaaatacgg catcccctat    420
gtcgtcacgg aacacagcag caccattacg cgcggtttgg tgcgtccgca ccaatggcag    480
cctatgaaaa atgcggcggc acacgcctcc gcactgctcg ctgtcagctg ccgtttcgcc    540
caagtcctgc aacataaata cggcactaca tggcaatatc tgcctaacat tctgggtaac    600
atctttaccc gagccttcaa tccccgcaa atcaaccgtc cggacaaata ttttaccttc    660
tgcactatct cccatctgcg ccggctaaaa ggacatgatg tcctcctgtc cgcctttgcc    720
cgtgctttgg caaaacaccc aaacctccgt ttgaatatcg gcggcagcgg acaagaagaa    780
acaagcctga acggcaggc acgtcagttg ggaattgccc atgccgttac atttttgggc    840
gcattgcagc ccgaagcagt cttggatttg atgaggaaca gcgacgcatt cgtccttgcc    900
agccgcacag aaaccttcgg cgtggtctat atcgaagcac tgtcccaagg attgcccgtc    960
attgcaacac gctgcggcgg tgcggaatct attgtttcag acggcaacgg atatttggtt   1020
cctgttgacg acgacgatgc ccttgccgac gcactcatca aaatgtatga acaccactct   1080
gatttgaac ctgaccgact tagggaaaac tgtctgaacg aatttggcga agataccgtt   1140
ataggcaagt tgatcggcat tttccgacag gcaatcgcag aatacggtaa gaaaataccg   1200
gtgaaatag                                                           1209
```

<210> SEQ ID NO 36
<211> LENGTH: 402
<212> TYPE: PRT
<213> ORGANISM: Neisseria meningitidis

<400> SEQUENCE: 36

```
Met Ser Glu Pro Leu His Val Leu Val Ile Pro Ser Trp Tyr Pro Gln
  1               5                  10                  15

Ser Glu Gln Asp Val Asp Gly Ile Phe Phe Gln Asn Gln Ala Leu Ala
             20                  25                  30

Leu Gln Arg Lys Gly Ile Lys Thr Ala Val Leu Ala Pro Met Phe Arg
         35                  40                  45

Tyr Leu Arg Lys Glu Thr Ala Ser Ile Leu Thr Gly Pro Tyr Gly Phe
     50                  55                  60

Ala Gln Tyr Arg Gln Lys Gly Leu Asp Ile Tyr Ala Trp His Gly Met
 65                  70                  75                  80

Tyr Phe Phe Pro Arg Phe Pro Leu Ile Asp Ile Asp Arg Ile Arg Trp
                 85                  90                  95

Val Arg Ala Gly Leu Lys Ala Phe Glu Arg Tyr Ile Gly Glu Asn Gly
            100                 105                 110

Ile Pro Asp Ile Ile His Ala His Cys Met Asn Tyr Ala Gly Ile Leu
        115                 120                 125

Ala Phe Lys Ile Ser Gln Lys Tyr Gly Ile Pro Tyr Val Val Thr Glu
    130                 135                 140

His Ser Ser Thr Ile Thr Arg Gly Leu Val Arg Pro His Gln Trp Gln
145                 150                 155                 160

Pro Met Lys Asn Ala Ala Ala His Ala Ser Ala Leu Leu Ala Val Ser
                165                 170                 175
```

```
Cys Arg Phe Ala Gln Val Leu Gln His Lys Tyr Gly Thr Thr Trp Gln
            180                 185                 190
Tyr Leu Pro Asn Ile Leu Gly Asn Ile Phe Thr Arg Ala Phe Asn Pro
        195                 200                 205
Pro Gln Ile Asn Arg Pro Asp Lys Tyr Phe Thr Phe Cys Thr Ile Ser
210                 215                 220
His Leu Arg Arg Leu Lys Gly His Asp Val Leu Leu Ser Ala Phe Ala
225                 230                 235                 240
Arg Ala Leu Ala Lys His Pro Asn Leu Arg Leu Asn Ile Gly Gly Ser
            245                 250                 255
Gly Gln Glu Glu Thr Ser Leu Lys Arg Gln Ala Arg Gln Leu Gly Ile
        260                 265                 270
Ala His Ala Val Thr Phe Leu Gly Ala Leu Gln Pro Glu Ala Val Leu
    275                 280                 285
Asp Leu Met Arg Asn Ser Asp Ala Phe Val Leu Ala Ser Arg Thr Glu
290                 295                 300
Thr Phe Gly Val Val Tyr Ile Glu Ala Leu Ser Gln Gly Leu Pro Val
305                 310                 315                 320
Ile Ala Thr Arg Cys Gly Gly Ala Glu Ser Ile Val Ser Asp Gly Asn
            325                 330                 335
Gly Tyr Leu Val Pro Val Asp Asp Asp Ala Leu Ala Asp Ala Leu
        340                 345                 350
Ile Lys Met Tyr Glu His His Ser Asp Phe Glu Pro Asp Arg Leu Arg
    355                 360                 365
Glu Asn Cys Leu Asn Glu Phe Gly Asp Thr Val Ile Gly Lys Leu
370                 375                 380
Ile Gly Ile Phe Arg Gln Ala Ile Ala Glu Tyr Gly Lys Lys Ile Pro
385                 390                 395                 400
Val Lys

<210> SEQ ID NO 37
<211> LENGTH: 894
<212> TYPE: DNA
<213> ORGANISM: Neisseria meningitidis

<400> SEQUENCE: 37
atgaagggtt taccattat tgaatttttg gttgcgggca tgctcagtat gattgtcctg      60
atggcggtcg gatcgagtta ctttacgtcc cggaaattaa atgatgcggc aaacgagcgt     120
cttgccgcgc aacaggattt gcggaatgcg gcaacattga ttgtccgcga tgcgagaatg     180
gcgggcggct cggttgtttt caatatgtcc gagcattctg caactgatgt tattcccgat     240
acgacgcaac aaaattctcc ttttccctta aaaaggaacg gtatagataa acttattccc     300
atagcggaat cttcaaatat cggatatccg gattttaccc agcgccttaa cgcattgatt     360
ttccaatacg gaatcgatga tgttaatgca agcgccgata ctaccgtcgt cagcagctgt     420
gccaaaatag caaaaccggg taagaaaata tctaccttgc aagaagcaaa gagtgcatta     480
cagattacta atgatgataa acaaaatgga atatcacccc gtcaaaggca tgtggtcaat     540
gcctatgcgg tcggcaggat tgccggtgag aaggtttgt tccgcttcca attgaatgat     600
aatgggcagt ggggtaatcc tcagttgttg gttaaaaaga ttaataaaat ggatatacgg     660
tatatttatg tttccaactg tcctgaagat gacgatgccg gcaaagagga acattcaaa     720 tatacgata aattcaacag cgcccaaaat gctgttacgc cgccggggt ggaggtttta     780 ttgagtagcg gtactgatac caagattgcc gcttcttcag acaatcatat ttatgcttac     840
```
cgtatcgatg cgacaatacg cgggggaaat gtatgcgcaa acagaacact ttga           894

<210> SEQ ID NO 38
<211> LENGTH: 297
<212> TYPE: PRT
<213> ORGANISM: Neisseria meningitidis

<400> SEQUENCE: 38

Met Lys Gly Phe Thr Ile Ile Glu Phe Leu Val Ala Gly Met Leu Ser
1               5                   10                  15

Met Ile Val Leu Met Ala Val Gly Ser Ser Tyr Phe Thr Ser Arg Lys
            20                  25                  30

Leu Asn Asp Ala Ala Asn Glu Arg Leu Ala Ala Gln Gln Asp Leu Arg
        35                  40                  45

Asn Ala Ala Thr Leu Ile Val Arg Asp Ala Arg Met Ala Gly Gly Phe
    50                  55                  60

Gly Cys Phe Asn Met Ser Glu His Ser Ala Thr Asp Val Ile Pro Asp
65                  70                  75                  80

Thr Thr Gln Gln Asn Ser Pro Phe Ser Leu Lys Arg Asn Gly Ile Asp
                85                  90                  95

Lys Leu Ile Pro Ile Ala Glu Ser Ser Asn Ile Gly Tyr Pro Asp Phe
            100                 105                 110

Thr Gln Arg Leu Asn Ala Leu Ile Phe Gln Tyr Gly Ile Asp Asp Val
        115                 120                 125

Asn Ala Ser Ala Asp Thr Thr Val Val Ser Ser Cys Ala Lys Ile Ala
    130                 135                 140

Lys Pro Gly Lys Lys Ile Ser Thr Leu Gln Glu Ala Lys Ser Ala Leu
145                 150                 155                 160

Gln Ile Thr Asn Asp Asp Lys Gln Asn Gly Asn Ile Thr Arg Gln Arg
                165                 170                 175

His Val Val Asn Ala Tyr Ala Val Gly Arg Ile Ala Gly Glu Glu Gly
            180                 185                 190

Leu Phe Arg Phe Gln Leu Asn Asp Asn Gly Gln Trp Gly Asn Pro Gln
        195                 200                 205

Leu Leu Val Lys Lys Ile Asn Lys Met Asp Ile Arg Tyr Ile Tyr Val
    210                 215                 220

Ser Asn Cys Pro Glu Asp Asp Ala Gly Lys Glu Thr Phe Lys
225                 230                 235                 240

Tyr Thr Asp Lys Phe Asn Ser Ala Gln Asn Ala Val Thr Pro Ala Gly
                245                 250                 255

Val Glu Val Leu Leu Ser Ser Gly Thr Asp Thr Lys Ile Ala Ala Ser
            260                 265                 270

Ser Asp Asn His Ile Tyr Ala Tyr Arg Ile Asp Ala Thr Ile Arg Gly
        275                 280                 285

Gly Asn Val Cys Ala Asn Arg Thr Leu
    290                 295

<210> SEQ ID NO 39
<211> LENGTH: 681
<212> TYPE: DNA
<213> ORGANISM: Neisseria meningitidis

<400> SEQUENCE: 39
gtgcaggcgg atttagctta tgccgccgaa cgtattaccc acgattatcc gaaagcaacc           60
ggtgcagaca aagacaaaat aagcacagta agcgattatt tcagaaacat ccgtgcgcat          120

```
tccatccacc ctcgtgtgtc ggtcggctac gacttcggcg gctggagaat agcggcagat    180
tatgccagtt acagaaaatg aacaacaat aaatattccg tcaacacaaa aaaggtgcaa    240
gaaaaccaag gcaccagaaa agacctgaag acggaaaatc aggaaaacgg cagcttccac    300
gccgcttctt ctctcggctt atccgccatt tacgatttca aactcaacga taaattcaaa    360
ccctatatcg gtgcgcgcgt cgcctacgga cacgtcagac acagcatcga ttcgaccaaa    420
aaaacaacag aggttgttac ctccacccat ggtggtgctg acacaaaacc tacgatttat    480
aatggggaaa gtacgcaaaa cgcctatcac gaaagccaca gcatccgccg cttgggtctt    540
ggtgtcgtcg ccggtgtcgg tttcgacatc acgcccaagc tgactttaga caccggatac    600
cgctaccaca actggggacg cttggaaaac acccgcttca aaacccacga agtctcattg    660
ggcatgcgct accgcttctg a                                             681
```

```
<210> SEQ ID NO 40
<211> LENGTH: 226
<212> TYPE: PRT
<213> ORGANISM: Neisseria meningitidis

<400> SEQUENCE: 40

Met Gln Ala Asp Leu Ala Tyr Ala Ala Glu Arg Ile Thr His Asp Tyr
  1               5                  10                  15

Pro Lys Ala Thr Gly Ala Asp Lys Asp Lys Ile Ser Thr Val Ser Asp
             20                  25                  30

Tyr Phe Arg Asn Ile Arg Ala His Ser Ile His Pro Arg Val Ser Val
         35                  40                  45

Gly Tyr Asp Phe Gly Gly Trp Arg Ile Ala Ala Asp Tyr Ala Ser Tyr
     50                  55                  60

Arg Lys Trp Asn Asn Lys Tyr Ser Val Asn Thr Lys Lys Val Gln
 65                  70                  75                  80

Glu Asn Gln Gly Thr Arg Lys Asp Leu Lys Thr Glu Asn Gln Glu Asn
                 85                  90                  95

Gly Ser Phe His Ala Ala Ser Ser Leu Gly Leu Ser Ala Ile Tyr Asp
            100                 105                 110

Phe Lys Leu Asn Asp Lys Phe Lys Pro Tyr Ile Gly Ala Arg Val Ala
        115                 120                 125

Tyr Gly His Val Arg His Ser Ile Asp Ser Thr Lys Lys Thr Thr Glu
    130                 135                 140

Val Val Thr Ser Thr His Gly Gly Ala Asp Thr Lys Pro Thr Ile Tyr
145                 150                 155                 160

Asn Gly Glu Ser Thr Gln Asn Ala Tyr His Glu Ser His Ser Ile Arg
                165                 170                 175

Arg Leu Gly Leu Gly Val Val Ala Gly Val Gly Phe Asp Ile Thr Pro
            180                 185                 190

Lys Leu Thr Leu Asp Thr Gly Tyr Arg Tyr His Asn Trp Gly Arg Leu
        195                 200                 205

Glu Asn Thr Arg Phe Lys Thr His Glu Val Ser Leu Gly Met Arg Tyr
    210                 215                 220

Arg Phe
225
```

```
<210> SEQ ID NO 41
<211> LENGTH: 1767
<212> TYPE: DNA
<213> ORGANISM: Neisseria meningitidis

<400> SEQUENCE: 41
```

```
atgaacaaaa taccgcat catttggaat agtgccctca atgcctgggt cgccgtatcc      60
gagctcacac gcaaccacac caaacgcgcc tccgcaaccg tggcgaccgc cgtattggcg    120
acactgttgt ttgcaacggt tcaggcgagt actaccgatg aagatgaaga agaagagtta   180
gaacccgtag tacgctctgc tctggtgttg caattcatga tcgataaaga aggcaatgga   240
gaaaacgaat ctacaggaaa ataggttgg agtatatatt acgacaatca caacactcta    300
cacggcgcaa ccgttaccct caaagccggc gacaacctga aaatcaaaca aaacggcaca   360
aacttcacct actcgctgaa aaagcccctc acaggtctga ccagtgttgg aactgaagaa   420
ttatcgtttg gcgcaaacgg caagaaagtc aacatcacaa gcgacaccaa aggcttgaat   480
tttgcgaaag aaacggctgg gacgaacggc gacaccacgg ttcatctgaa cggtattggt   540
tctactttaa ccgatacgct tgcgggttct tctgcttctc acgttgatgc gggtaaccaa   600
agtacacatt acactcgtgc agcaagtatt aaggatgtgt tgaatgcggg ttggaatatt   660
aagggtgtta aaactggctc aacaactggt caatcagaaa atgtcgattt cgtccgcact   720
tacgacacag tcgagttctt gagcgcagat acgaaaacaa cgactgttaa tgtggaaagc   780
aaagacaacg gcaagagaac cgaagttaaa atcggtgcga agacttctgt tatcaaagaa   840
aaagacggta agttggttac tggtaaaggc aaaggcgaga atggttcttc tacagacgaa   900
ggcgaaggct tagtgactgc aaaagaagtg attgatgcag taaacaaggc tggttggaga   960
atgaaaacaa caaccgctaa tggtcaaaca ggtcaagctg acaagtttga aaccgttaca  1020
tcaggcacaa atgtaacctt tgctagtggt aaaggtacaa ctgcgactgt aagtaaagat  1080
gctcaaggca acatcactgt taagtatgat gtaaatgtcg gcgatgccct aaacgtcaat  1140
cagctgcaaa acagcggttg gaatttggat tccaaagcgg ttgcaggttc ttcgggcaaa  1200
gtcatcagcg gcaatgtttc gccgagcaag ggaaagatgg atgaaaccgt caacattaat  1260
gccggcaaca catcgagat tacccgcaac ggtaaaaata tcgacatcgc cacttcgatg  1320
accccgcagt tttccagcgt ttcgctcggc gcggggcgg atgcgcccac tttgagcgtg  1380
gatggggacg cattgaatgt cggcagcaag aaggacaaca aacccgtccg cattaccaat  1440
gtcgccccgg gcgttaaaga gggggatgtt acaaacgtcg cacaacttaa aggcgtggcg  1500
caaaacttga caaccgcat cgacaatgtg gacggcaacg cgcgtgcggg catcgcccaa  1560
gcgattgcaa ccgcaggtct ggttcaggcg tatttgcccg gcaagagtat gatggcgatc  1620
ggcggcggca cttatcgcgg cgaagccggt tacgccatcg gctactccag tatttccgac  1680
ggcggaaatt ggattatcaa aggcacggct tccggcaatt cgcgcggcca tttcggtgct  1740
tccgcatctg tcggttatca gtggtaa                                      1767
```

<210> SEQ ID NO 42
<211> LENGTH: 588
<212> TYPE: PRT
<213> ORGANISM: Neisseria meningitidis

<400> SEQUENCE: 42

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
        35                  40                  45

Ala Ser Thr Thr Asp Glu Asp Glu Glu Glu Leu Glu Pro Val Val
    50                  55                  60

```
Arg Ser Ala Leu Val Leu Gln Phe Met Ile Asp Lys Glu Gly Asn Gly
 65                  70                  75                  80

Glu Asn Glu Ser Thr Gly Asn Ile Gly Trp Ser Ile Tyr Tyr Asp Asn
                 85                  90                  95

His Asn Thr Leu His Gly Ala Thr Val Thr Leu Lys Ala Gly Asp Asn
            100                 105                 110

Leu Lys Ile Lys Gln Asn Gly Thr Asn Phe Thr Tyr Ser Leu Lys Lys
        115                 120                 125

Ala Leu Thr Gly Leu Thr Ser Val Gly Thr Glu Glu Leu Ser Phe Gly
    130                 135                 140

Ala Asn Gly Lys Lys Val Asn Ile Thr Ser Asp Thr Lys Gly Leu Asn
145                 150                 155                 160

Phe Ala Lys Glu Thr Ala Gly Thr Asn Gly Asp Thr Val His Leu
                165                 170                 175

Asn Gly Ile Gly Ser Thr Leu Thr Asp Thr Leu Ala Gly Ser Ser Ala
            180                 185                 190

Ser His Val Asp Ala Gly Asn Gln Ser Thr His Tyr Thr Arg Ala Ala
        195                 200                 205

Ser Ile Lys Asp Val Leu Asn Ala Gly Trp Asn Ile Lys Gly Val Lys
    210                 215                 220

Thr Gly Ser Thr Thr Gly Gln Ser Glu Asn Val Asp Phe Val Arg Thr
225                 230                 235                 240

Tyr Asp Thr Val Glu Phe Leu Ser Ala Asp Thr Lys Thr Thr Thr Val
                245                 250                 255

Asn Val Glu Ser Lys Asp Asn Gly Lys Arg Thr Glu Val Lys Ile Gly
            260                 265                 270

Ala Lys Thr Ser Val Ile Lys Glu Lys Asp Gly Lys Leu Val Thr Gly
        275                 280                 285

Lys Gly Lys Gly Glu Asn Gly Ser Ser Thr Asp Glu Gly Glu Gly Leu
    290                 295                 300

Val Thr Ala Lys Glu Val Ile Asp Ala Val Asn Lys Ala Gly Trp Arg
305                 310                 315                 320

Met Lys Thr Thr Thr Ala Asn Gly Gln Thr Gly Gln Ala Asp Lys Phe
                325                 330                 335

Glu Thr Val Thr Ser Gly Thr Asn Val Thr Phe Ala Ser Gly Lys Gly
            340                 345                 350

Thr Thr Ala Thr Val Ser Lys Asp Ala Gln Gly Asn Ile Thr Val Lys
        355                 360                 365

Tyr Asp Val Asn Val Gly Asp Ala Leu Asn Val Asn Gln Leu Gln Asn
    370                 375                 380

Ser Gly Trp Asn Leu Asp Ser Lys Ala Val Ala Gly Ser Ser Gly Lys
385                 390                 395                 400

Val Ile Ser Gly Asn Val Ser Pro Ser Lys Gly Lys Met Asp Glu Thr
                405                 410                 415

Val Asn Ile Asn Ala Gly Asn Asn Ile Glu Ile Thr Arg Asn Gly Lys
            420                 425                 430

Asn Ile Asp Ile Ala Thr Ser Met Thr Pro Gln Phe Ser Ser Val Ser
        435                 440                 445

Leu Gly Ala Gly Ala Asp Ala Pro Thr Leu Ser Val Asp Gly Asp Ala
    450                 455                 460

Leu Asn Val Gly Ser Lys Lys Asp Asn Lys Pro Val Arg Ile Thr Asn
465                 470                 475                 480

Val Ala Pro Gly Val Lys Glu Gly Asp Val Thr Asn Val Ala Gln Leu
```

```
                      485                 490                 495
Lys Gly Val Ala Gln Asn Leu Asn Asn Arg Ile Asp Asn Val Asp Gly
                500                 505                 510

Asn Ala Arg Ala Gly Ile Ala Gln Ala Ile Ala Thr Ala Gly Leu Val
            515                 520                 525

Gln Ala Tyr Leu Pro Gly Lys Ser Met Met Ala Ile Gly Gly Gly Thr
        530                 535                 540

Tyr Arg Gly Glu Ala Gly Tyr Ala Ile Gly Tyr Ser Ser Ile Ser Asp
545                 550                 555                 560

Gly Gly Asn Trp Ile Ile Lys Gly Thr Ala Ser Gly Asn Ser Arg Gly
                565                 570                 575

His Phe Gly Ala Ser Ala Ser Val Gly Tyr Gln Trp
            580                 585
```

```
<210> SEQ ID NO 43
<211> LENGTH: 606
<212> TYPE: DNA
<213> ORGANISM: Neisseria meningitidis

<400> SEQUENCE: 43
atgattgaat ccatagaaaa accacaggaa tctatcagaa aaacagaaaa cccccaccgc        60
gtcattcccg cgaaagcggg aatccagaaa cgcaacgcaa caggaattta tcggaaaaaa       120
cagaaacctc accgccgtca ttcccgcaaa agctggaatc caaaaacgca acgcggcagg       180
actttatcgg aaaaaacaga accccaccg ccgtcattc cgcaaaagc gggaatccaa          240 aaacgcaacg caacaggaat ttatcggaaa aaacagaaac cccaccgacc gtcattcccg       300
caaaagcggg aatccagcaa ccgaaaaacc acaggaatct atcagcaaaa acagaaaccc       360
ccaccgaccg tcattcccgc gcaggcggga atccagaaac acaacgcggc aggactttat       420
cggaaaaaac agaaactcca ccgaccgtca ttcccgcaaa agctggaatc caaaaacgca       480
acgcaacagg aatttatcgg aaaaaacaga accccaccg ccgtcattcc cgcaaaagcg        540
ggaatccaga cccgtcggca cggaatctta ccggataaaa cagtttcctt agattccacg       600
tcctag                                                                  606
```

```
<210> SEQ ID NO 44
<211> LENGTH: 201
<212> TYPE: PRT
<213> ORGANISM: Neisseria meningitidis

<400> SEQUENCE: 44

Met Ile Glu Ser Ile Glu Lys Pro Gln Glu Ser Ile Arg Lys Asn Arg
  1               5                  10                  15

Asn Pro His Arg Val Ile Pro Ala Lys Ala Gly Ile Gln Lys Arg Asn
             20                  25                  30

Ala Thr Gly Ile Tyr Arg Lys Lys Gln Lys Pro His Arg Arg His Ser
         35                  40                  45

Arg Lys Ser Trp Asn Pro Lys Thr Gln Arg Gly Arg Thr Leu Ser Glu
     50                  55                  60

Lys Thr Glu Thr Pro Pro Thr Val Ile Pro Ala Lys Ala Gly Ile Gln
 65                  70                  75                  80

Lys Arg Asn Ala Thr Gly Ile Tyr Arg Lys Lys Gln Lys Pro His Arg
                 85                  90                  95

Pro Ser Phe Pro Gln Lys Arg Glu Ser Ser Asn Arg Lys Thr Thr Gly
            100                 105                 110

Ile Tyr Gln Gln Lys Gln Lys Pro Pro Thr Val Ile Pro Ala Gln
```

```
                115              120               125
Ala Gly Ile Gln Lys His Asn Ala Ala Gly Leu Tyr Arg Lys Gln
        130              135             140

Lys Leu His Arg Pro Ser Phe Pro Gln Lys Leu Glu Ser Lys Asn Ala
145                 150             155                 160

Thr Gln Gln Glu Phe Ile Gly Lys Asn Arg Asn Pro Thr Ala Val Ile
                165             170             175

Pro Ala Lys Ala Gly Ile Gln Thr Arg Arg His Gly Ile Leu Pro Asp
            180             185             190

Lys Thr Val Ser Leu Asp Ser Thr Ser
        195             200

<210> SEQ ID NO 45
<211> LENGTH: 1014
<212> TYPE: DNA
<213> ORGANISM: Neisseria meningitidis

<400> SEQUENCE: 45
atgattttct ccatcatcgt ccctatttac aatgtggaaa atacctccg ctgctgcgtg     60
gattccgtgc ttgccgaaaa ttttgccgat tatgaaatga ttttggtcga tgacggttcg    120
ccggatggct gcgggaagat ttgcgacgaa tatgcaggca aatatccgca tataaaagtg    180
attcatcaag aaacggcgg gctgtcggat gcccgcaacg ccgtatccg agcggcaaaa    240
ggcgattacc tgatcttttt ggacagcgac gactattggg ccgataccaa ccgttcaaaa    300
aacgcgggg ggggattct ctttgattta caacaacttg cagacaaaaa ggttgatttg     360
atcctgcatc cctcgtccct caattaccac gtcatcccca aggggcgga cttttcggat    420
aatgattttg tccgccattt tgaaacgttg gtggaggggc ggtactatat cgccaacgcg   480
tggacaaaaa tcgtcaggcg ggaaataatc atcaaaaaca atctgttttt cccaaaagga    540
tacattcacg aggattccc gtacagtttg caattggcgc gttttatcaa gacttttgcc     600
ttttacgata acccttttta ccagtaccgc gttctcggcg gctctatcag ccacaacatc    660
aaatacaaaa atttcagcga tgtgctgacg catctcgacc ggggtgtgga tttttagtc    720
gaaaacaaaa attccccat ctacggcggt ttgcaaaaat ttgtcttcga caatatcggc    780
tatctgaggt ctatattggt aaggctttat ttttccaaaa acattatcgt catctaccgg    840
aaatattttt catttaaaga aaaatgcaga aagatattcg gcgcgaaggc aatccgtccg   900
gtttttatcg ggaagaccgc attcatcata ggattgccga tattgcgcct gctcgtaccg    960
cctatgctgt acccggcaat caaggccgtt atcaaaaat tttttcgga ataa           1014

<210> SEQ ID NO 46
<211> LENGTH: 337
<212> TYPE: PRT
<213> ORGANISM: Neisseria meningitidis

<400> SEQUENCE: 46

Met Ile Phe Ser Ile Ile Val Pro Ile Tyr Asn Val Glu Lys Tyr Leu
 1               5                   10                  15

Arg Cys Cys Val Asp Ser Val Leu Ala Glu Asn Phe Ala Asp Tyr Glu
                20                  25                  30

Met Ile Leu Val Asp Asp Gly Ser Pro Asp Gly Cys Gly Lys Ile Cys
            35                  40                  45

Asp Glu Tyr Ala Gly Lys Tyr Pro His Ile Lys Val Ile His Gln Glu
        50                  55                  60

Asn Gly Gly Leu Ser Asp Ala Arg Asn Ala Gly Ile Arg Ala Ala Lys
```

```
                65                  70                  75                  80
Gly Asp Tyr Leu Ile Phe Leu Asp Ser Asp Tyr Trp Ala Asp Thr
                    85                  90                  95
Asn Arg Ser Lys Asn Ala Gly Gly Ile Leu Phe Asp Leu Gln Gln
                100                 105                 110
Leu Ala Asp Lys Lys Val Asp Leu Ile Leu His Pro Ser Leu Asn
            115                 120                 125
Tyr His Val Ile Pro Lys Gly Ala Asp Phe Ser Asp Asn Asp Phe Val
    130                 135                 140
Arg His Phe Glu Thr Leu Val Glu Gly Arg Tyr Tyr Ile Ala Asn Ala
145                 150                 155                 160
Trp Thr Lys Ile Val Arg Arg Glu Ile Ile Lys Asn Asn Leu Phe
                165                 170                 175
Phe Pro Lys Gly Tyr Ile His Glu Asp Phe Pro Tyr Ser Leu Gln Leu
                180                 185                 190
Ala Arg Phe Ile Lys Thr Phe Ala Phe Tyr Asp Asn Pro Phe Tyr Gln
            195                 200                 205
Tyr Arg Val Leu Gly Gly Ser Ile Ser His Asn Ile Lys Tyr Lys Asn
    210                 215                 220
Phe Ser Asp Val Leu Thr His Leu Asp Arg Gly Val Asp Phe Leu Val
225                 230                 235                 240
Glu Asn Lys Asn Ser Pro Ile Tyr Gly Gly Leu Gln Lys Phe Val Phe
                245                 250                 255
Asp Asn Ile Gly Tyr Leu Arg Ser Ile Leu Val Arg Leu Tyr Phe Ser
            260                 265                 270
Lys Asn Ile Ile Val Ile Tyr Arg Lys Tyr Phe Ser Phe Lys Glu Lys
    275                 280                 285
Cys Arg Lys Ile Phe Gly Ala Lys Ala Ile Arg Pro Val Phe Ile Gly
    290                 295                 300
Lys Thr Ala Phe Ile Ile Gly Leu Pro Ile Leu Arg Leu Leu Val Pro
305                 310                 315                 320
Pro Met Leu Tyr Pro Ala Ile Lys Ala Val Tyr Gln Lys Phe Phe Ser
                325                 330                 335
Glu

<210> SEQ ID NO 47
<211> LENGTH: 1590
<212> TYPE: DNA
<213> ORGANISM: Neisseria meningitidis
<220> FEATURE:
<221> NAME/KEY: misc_feature
<222> LOCATION: 1571, 1572, 1573, 1574, 1575
<223> OTHER INFORMATION: n = A,T,C or G

<400> SEQUENCE: 47
atgacatctg caaattttaa tattaacggt tttggagatg tgaaattaac accctattca      60
ccactcttgg gatataaagc ttgggattca tttattggtt ctattcaatc cttatctgat     120
ttaatctata atgtggataa caatagaaat aaaatgaaa ttactgttaa taatgctatc     180
caagctgcag atagcttttt aagcagtatt ggaagagata caaaataac aaatactgct     240 tctttacttg catccctcga taacattttt taaatttaa gaatgtatc tcgagatata     300 cgagaaacag gaaaatttaa acctaatgat attcaacaag caattggtga tatattcatt     360
gctgctggtg atggattaca atatataaaa caacaaacag aggcgatggc tcaaagcaaa     420
ttcttaccaa ctaaattaaa aactggttta aatgatgtcc ttaattctag aatgctaaaa     480
```

-continued

```
tcctctactg ttttacagca tgaattgaat tatttgggat ttaaaataaa ggattatgga    540
aacgagaggc ttggcgaatc tataatgaat atagatgatt ttacaccaag taagatagca    600
aacttttttg cggatcctga tacatacagc aatgtattag aagaagtatc taggtttata    660
tattccttag ttcctgatga tgcaaaccct tggaaagggg gcgaagatta tattggacga    720
gggataagtg aatggggaga gttactggaa aaatggtata acaagatttt ctcccttat    780
cttgaaaaag aatgggacca atttccgaaa tttgaagatt ggctgcctga attccctgaa    840
tgggcaagag agtggttgaa attagatccc aaacgttcag gcaaatatca tgtctacgac    900
ccctcgccc tagatctaga cggcgacggt atagaaaccg ttccaccaa aggctttgca    960
ggcagcttat ttgatcacac caacaacggt atccgcaccg ccaccggttg ggtttctgcc   1020
gatgacggtt tactcgtccg cgatttgaac ggcaacggca tcatcgacaa cggtgcggaa   1080
ctcttcggcg acaacaccaa actggcagac ggttcttttg ccaaacacgg ctatgcagct   1140
ttggccgaat tggattcaaa cggcgacaac atcatcaacg cggcagacgc cgcattccaa   1200
accctgcgtg tatggcagga tctcaatcag gacggcattt cccaaaccaa cgaactccgc   1260
acccttgaag aattgggtat tcaatctttg gatctcgcct ataaagatgt aaataaaaat   1320
ctcggtaacg gtaacacttt ggctcagcaa ggtagctaca ccaaaacaaa cggtacaacc   1380
gcaaaaatgg gggatttact tttagcagcc gacaatctgc acagccgctt caaagacaaa   1440
gtggaactca ctgccaaaca ggcaaaagcc gccaatcttg cgggcattgg tcgtctgcgc   1500
gatttgcgcg aagctgccgc attgtccggc gatttggcca atatgctgaa agcttattct   1560
gccgccgaaa nnnnncacac acttaattaa                                    1590
```

<210> SEQ ID NO 48
<211> LENGTH: 529
<212> TYPE: PRT
<213> ORGANISM: Neisseria meningitidis
<220> FEATURE:
<221> NAME/KEY: VARIANT
<222> LOCATION: 524, 525
<223> OTHER INFORMATION: Xaa = Any Amino Acid

<400> SEQUENCE: 48

```
Met Thr Ser Ala Asn Phe Asn Ile Asn Gly Phe Gly Asp Val Lys Leu
  1               5                  10                  15

Thr Pro Tyr Ser Pro Leu Leu Gly Tyr Lys Ala Trp Asp Ser Phe Ile
             20                  25                  30

Gly Ser Ile Gln Ser Leu Ser Asp Leu Ile Tyr Asn Val Asp Asn Asn
         35                  40                  45

Arg Asn Lys Met Glu Ile Thr Val Asn Asn Ala Ile Gln Ala Ala Asp
     50                  55                  60

Ser Phe Leu Ser Ser Ile Gly Arg Asp Asn Lys Ile Thr Asn Thr Ala
 65                  70                  75                  80

Ser Leu Leu Ala Ser Leu Asp Asn Ile Phe Leu Asn Leu Arg Asn Val
                 85                  90                  95

Ser Arg Asp Ile Arg Glu Thr Gly Lys Phe Lys Pro Asn Asp Ile Gln
            100                 105                 110

Gln Ala Ile Gly Asp Ile Phe Ile Ala Ala Gly Asp Gly Leu Gln Tyr
        115                 120                 125

Ile Lys Gln Gln Thr Glu Ala Met Ala Gln Ser Lys Phe Leu Pro Thr
    130                 135                 140

Lys Leu Lys Thr Gly Leu Asn Asp Val Leu Asn Ser Arg Met Leu Lys
145                 150                 155                 160
```

Ser Ser Thr Val Leu Gln His Glu Leu Asn Tyr Leu Gly Phe Lys Ile
            165                 170                 175

Lys Asp Tyr Gly Asn Glu Arg Leu Gly Glu Ser Ile Met Asn Ile Asp
            180                 185                 190

Asp Phe Thr Pro Ser Lys Ile Ala Asn Phe Phe Ala Asp Pro Asp Thr
            195                 200                 205

Tyr Ser Asn Val Leu Glu Glu Val Ser Arg Phe Ile Tyr Ser Leu Val
            210                 215                 220

Pro Asp Asp Ala Asn Pro Trp Lys Gly Gly Glu Asp Tyr Ile Gly Arg
225                 230                 235                 240

Gly Ile Ser Glu Trp Gly Glu Leu Leu Glu Lys Trp Tyr Lys Gln Asp
            245                 250                 255

Phe Leu Pro Tyr Leu Glu Lys Glu Trp Asp Gln Phe Pro Lys Phe Glu
            260                 265                 270

Asp Trp Leu Pro Glu Phe Pro Glu Trp Ala Arg Glu Trp Leu Lys Leu
            275                 280                 285

Asp Pro Lys Arg Ser Gly Lys Tyr His Val Tyr Asp Pro Leu Ala Leu
            290                 295                 300

Asp Leu Asp Gly Asp Gly Ile Glu Thr Val Ala Thr Lys Gly Phe Ala
305                 310                 315                 320

Gly Ser Leu Phe Asp His Thr Asn Asn Gly Ile Arg Thr Ala Thr Gly
            325                 330                 335

Trp Val Ser Ala Asp Asp Gly Leu Leu Val Arg Asp Leu Asn Gly Asn
            340                 345                 350

Gly Ile Ile Asp Asn Gly Ala Glu Leu Phe Gly Asp Asn Thr Lys Leu
            355                 360                 365

Ala Asp Gly Ser Phe Ala Lys His Gly Tyr Ala Ala Leu Ala Glu Leu
            370                 375                 380

Asp Ser Asn Gly Asp Asn Ile Ile Asn Ala Ala Asp Ala Ala Phe Gln
385                 390                 395                 400

Thr Leu Arg Val Trp Gln Asp Leu Asn Gln Asp Gly Ile Ser Gln Thr
            405                 410                 415

Asn Glu Leu Arg Thr Leu Glu Glu Leu Gly Ile Gln Ser Leu Asp Leu
            420                 425                 430

Ala Tyr Lys Asp Val Asn Lys Asn Leu Gly Asn Gly Asn Thr Leu Ala
            435                 440                 445

Gln Gln Gly Ser Tyr Thr Lys Thr Asn Gly Thr Thr Ala Lys Met Gly
            450                 455                 460

Asp Leu Leu Leu Ala Ala Asp Asn Leu His Ser Arg Phe Lys Asp Lys
465                 470                 475                 480

Val Glu Leu Thr Ala Lys Gln Ala Lys Ala Ala Asn Leu Ala Gly Ile
            485                 490                 495

Gly Arg Leu Arg Asp Leu Arg Glu Ala Ala Ala Leu Ser Gly Asp Leu
            500                 505                 510

Ala Asn Met Leu Lys Ala Tyr Ser Ala Ala Glu Xaa Xaa His Thr Leu
            515                 520                 525

Asn

<210> SEQ ID NO 49
<211> LENGTH: 2031
<212> TYPE: DNA
<213> ORGANISM: Neisseria meningitidis

<400> SEQUENCE: 49
ttgaggcgga atatcgcaac ttctgataag gatggcaatg attttccaaa tagcaaacaa    60

```
gcagaagaaa agctgtcgtt taaagaggaa gatatcctgt ttttatacgg ttccaaaaaa    120
gatcaacgtc agcagcttga agataaaatt catcaacgca atcctaatgt aaaaattagg    180
acatcagaaa atgaaaataa aaatatggt tataactttg tagatgcagg ttatgtatat     240
gtaaagggag aagatgaaat tgagaggact tcaaattaca agtattttac tcaccggttt    300
ggttatgacg ttttgtata ttattccgga gaacgtcctt cccaatcttt accgagttcg     360
ggaacggtgc aatattccgg caactggcaa tatatgaccg atgccatacg tcatcggaca    420
ggaaaagcag gagatcctag cgaagatttg ggttatctcg tttattacgg tcaaaatgtc    480
ggagcaactt cttatgctgc gactgccgac gaccgggagg gggagggaaa acatcctgcc    540
gaatatacgg ttgatttcga caaaaaaacc ctgaatggca agctgattaa aaatcagtat    600
gtgcaaaaga aggacgatga aaagaaaccg ctgaccattt acaacattac tgcaaaattg    660
gacggcaacc gctttaccgg cagtgccaag gtcaatcctg atttagcgaa aaaccatgcc    720
aagaaggagc atttgtttt ccataccgat gccgatcagc ggcttgaggg cggtttttc      780 ggcgataagg gggaagagct tgccggacgg tttatcagca cgacaacag cgtattcggc     840 gtattcgcag gcaaacaaaa aacagaggca gcaaacgcag cagatacaaa acttgccttg    900
ccgtctagaa aacacaccaa aatcttggat tctctaaaaa tttccgttga cgaggcaagt    960
gataacaatg cccgccagtt tgccatttcc tctatgcccg atcttggtca tcccgacaaa   1020
cttcttgtcg aagggcgtga aattcctttg gtaaaccaag aacaaaccat cgatcttgcc   1080
gacggcagga aaatgaccgt ccgtgcttgt tgcgattttc tgacctatgt gaaactcgga   1140
cggataaaaa ccgaccgccc ggcaagtaaa tcaaggcgg aagataaagg ggaggatgaa    1200
gagggtgcag gcgttgataa cggcgaagaa gacgaaatca gcgatgaaga cgaagtttcc   1260
gaagatgaaa gcgaagaaga cgaagaaatc gtcgaagaag aaaccgaaga agacgaaacc   1320
gaagaagacg aagaggggga agctgaagag gaagaagccg aagaagcaga gaaaactgaa   1380
gaaaaatcgc cggcagaagg caacggcgat tcaggcagca tcctgcctgc cccggaagcc   1440
cctaaaggca gggacatcga ccttttcctg aaaggtatcc gcacggcgga agccgacatt   1500
ccgcaaaccg gaaaagcaca ctataccggc acttgggaag cgcgtatcag caaacccatt   1560
caatgggata taaggcgga taaagcggca aaagcagagt ttaatgttga tttcggcgag    1620
aaatcgattt ccggaacgct gacggagaaa aatggtgtag aagctgcttt ctatattgaa   1680 aaggtgtga ttgagggcaa cggttttccac gcgacagcgc gcactcggga gaacggcatc    1740 gaccttttccg ggcagggttc gaccagatcg cagagcttca aagccgacaa tcttcttgta  1800
acgggcggct tttacggccc gaaggcgag gaattgggcg gtactatttt caataatgat    1860
gggaaatctc ttagtataac tgaaaatatt gaaaatgaag ttgaagttga agctgaagct   1920
gaagttgaag ttgaagctga tgttggcaaa cagttagaac ctgatgaagt taaacaccaa   1980
ttcggcgtgg tatttggtgc gaagaaagat aataagagg tggaaaaatg a             2031
```

<210> SEQ ID NO 50
<211> LENGTH: 676
<212> TYPE: PRT
<213> ORGANISM: Neisseria meningitidis

<400> SEQUENCE: 50

```
Met Arg Arg Asn Ile Ala Thr Ser Asp Lys Asp Gly Asn Asp Phe Pro
 1               5                  10                  15

Asn Ser Lys Gln Ala Glu Glu Lys Leu Ser Phe Lys Glu Glu Asp Ile
             20                  25                  30
```

```
Leu Phe Leu Tyr Gly Ser Lys Lys Asp Gln Arg Gln Gln Leu Glu Asp
            35                  40                  45

Lys Ile His Gln Arg Asn Pro Asn Val Lys Ile Arg Thr Ser Glu Asn
 50                  55                  60

Glu Asn Lys Lys Tyr Gly Tyr Asn Phe Val Asp Ala Gly Tyr Val Tyr
 65                  70                  75                  80

Val Lys Gly Glu Asp Glu Ile Glu Arg Thr Ser Asn Tyr Lys Tyr Phe
                     85                  90                  95

Thr His Arg Phe Gly Tyr Asp Gly Phe Val Tyr Tyr Ser Gly Glu Arg
                100                 105                 110

Pro Ser Gln Ser Leu Pro Ser Ser Gly Thr Val Gln Tyr Ser Gly Asn
            115                 120                 125

Trp Gln Tyr Met Thr Asp Ala Ile Arg His Arg Thr Gly Lys Ala Gly
            130                 135                 140

Asp Pro Ser Glu Asp Leu Gly Tyr Leu Val Tyr Tyr Gly Gln Asn Val
145                 150                 155                 160

Gly Ala Thr Ser Tyr Ala Ala Thr Ala Asp Asp Arg Glu Gly Glu Gly
                165                 170                 175

Lys His Pro Ala Glu Tyr Thr Val Asp Phe Asp Lys Lys Thr Leu Asn
            180                 185                 190

Gly Lys Leu Ile Lys Asn Gln Tyr Val Gln Lys Lys Asp Asp Glu Lys
            195                 200                 205

Lys Pro Leu Thr Ile Tyr Asn Ile Thr Ala Lys Leu Asp Gly Asn Arg
            210                 215                 220

Phe Thr Gly Ser Ala Lys Val Asn Pro Asp Leu Ala Lys Asn His Ala
225                 230                 235                 240

Lys Lys Glu His Leu Phe Phe His Thr Asp Ala Asp Gln Arg Leu Glu
                245                 250                 255

Gly Gly Phe Phe Gly Asp Lys Gly Glu Glu Leu Ala Gly Arg Phe Ile
            260                 265                 270

Ser Asn Asp Asn Ser Val Phe Gly Val Phe Ala Gly Lys Gln Lys Thr
            275                 280                 285

Glu Ala Ala Asn Ala Ala Asp Thr Lys Leu Ala Leu Pro Ser Arg Lys
290                 295                 300

His Thr Lys Ile Leu Asp Ser Leu Lys Ile Ser Val Asp Glu Ala Ser
305                 310                 315                 320

Asp Asn Asn Ala Arg Gln Phe Ala Ile Ser Ser Met Pro Asp Leu Gly
                325                 330                 335

His Pro Asp Lys Leu Leu Val Glu Gly Arg Glu Ile Pro Leu Val Asn
            340                 345                 350

Gln Glu Gln Thr Ile Asp Leu Ala Asp Gly Arg Lys Met Thr Val Arg
            355                 360                 365

Ala Cys Cys Asp Phe Leu Thr Tyr Val Lys Leu Gly Arg Ile Lys Thr
370                 375                 380

Asp Arg Pro Ala Ser Lys Ser Lys Ala Glu Asp Lys Gly Glu Asp Glu
385                 390                 395                 400

Glu Gly Ala Gly Val Asp Asn Gly Glu Glu Asp Ile Ser Asp Glu
                405                 410                 415

Asp Glu Val Ser Glu Asp Glu Ser Glu Glu Asp Glu Glu Ile Val Glu
            420                 425                 430

Glu Glu Thr Glu Glu Asp Glu Thr Glu Asp Glu Glu Gly Glu Ala
            435                 440                 445

Glu Glu Glu Glu Ala Glu Glu Ala Glu Glu Thr Glu Glu Lys Ser Pro
```

|    |    |    |    | 450 |    |    |    | 455 |    |    |    | 460 |    |    |
|----|----|----|----|-----|----|----|----|-----|----|----|----|-----|----|----|

Ala Glu Gly Asn Gly Asp Ser Gly Ser Ile Leu Pro Ala Pro Glu Ala
465                 470                 475                 480

Pro Lys Gly Arg Asp Ile Asp Leu Phe Leu Lys Gly Ile Arg Thr Ala
            485                 490                 495

Glu Ala Asp Ile Pro Gln Thr Gly Lys Ala His Tyr Thr Gly Thr Trp
        500                 505                 510

Glu Ala Arg Ile Ser Lys Pro Ile Gln Trp Asp Asn Lys Ala Asp Lys
    515                 520                 525

Ala Ala Lys Ala Glu Phe Asn Val Asp Phe Gly Glu Lys Ser Ile Ser
530                 535                 540

Gly Thr Leu Thr Glu Lys Asn Gly Val Glu Ala Ala Phe Tyr Ile Glu
545                 550                 555                 560

Lys Gly Val Ile Glu Gly Asn Gly Phe His Ala Thr Ala Arg Thr Arg
            565                 570                 575

Glu Asn Gly Ile Asp Leu Ser Gly Gln Gly Ser Thr Arg Ser Gln Ser
        580                 585                 590

Phe Lys Ala Asp Asn Leu Leu Val Thr Gly Gly Phe Tyr Gly Pro Lys
    595                 600                 605

Ala Glu Glu Leu Gly Gly Thr Ile Phe Asn Asn Asp Gly Lys Ser Leu
610                 615                 620

Ser Ile Thr Glu Asn Ile Glu Asn Glu Val Glu Val Glu Ala Glu Ala
625                 630                 635                 640

Glu Val Glu Val Glu Ala Asp Val Gly Lys Gln Leu Glu Pro Asp Glu
            645                 650                 655

Val Lys His Gln Phe Gly Val Val Phe Gly Ala Lys Lys Asp Asn Lys
        660                 665                 670

Glu Val Glu Lys
        675

<210> SEQ ID NO 51
<211> LENGTH: 612
<212> TYPE: DNA
<213> ORGANISM: Neisseria meningitidis
<220> FEATURE:
<221> NAME/KEY: misc_feature
<222> LOCATION: 589, 590, 591, 592, 593
<223> OTHER INFORMATION: n = A,T,C or G

<400> SEQUENCE: 51
gtgggaatcc agttttttga gtttcagtca ttcccgataa attgccttag cattgaatgt      60
ctagattccc gcctgcgcgg gaatgacgaa tccatccgta cggaaacctg caccacgtca     120
ttcccacgaa cctgcaccac gtcattccca cgaacctgca tccgtcatt cccacgaacc     180
tgcatcccgt cattcccacg agcctgcatc cgtcattcc cacgaacctg catcccgtca     240
ttcccacgaa cctgcatccc gtcattccca cgaacctgca tccgtcatt cccacgaacc     300
tgcatcccgt cattcccacg aacctgcatc cgtcattcc cacgaacctg catcccgtca     360
ttcccacgaa cctgcatccc gtcattccca cgaaagtggg aatccagttc gttcggtttc     420
gcttgtttta agtttcgggt aacttccact tcgtcattcc cgcgaacctg cattccgtca     480
ttcccacgaa agtgggaatc cagttcgttc ggtttcgctt gttttaagtt tcgggtaact     540
tccacttcgt cattcccgcg aacctacatt ccgtcattcc cacgaaagnn nnncacacac     600
ttaattaatt aa                                                         612

<210> SEQ ID NO 52

```
<211> LENGTH: 203
<212> TYPE: PRT
<213> ORGANISM: Neisseria meningitidis
<220> FEATURE:
<221> NAME/KEY: VARIANT
<222> LOCATION: 197, 198
<223> OTHER INFORMATION: Xaa = Any Amino Acid

<400> SEQUENCE: 52
```

Met Gly Ile Gln Phe Phe Glu Phe Gln Ser Phe Pro Ile Asn Cys Leu
 1               5                  10                  15

Ser Ile Glu Cys Leu Asp Ser Arg Leu Arg Gly Asn Asp Glu Ser Ile
            20                  25                  30

Arg Thr Glu Thr Cys Thr Thr Ser Phe Pro Arg Thr Cys Thr Thr Ser
        35                  40                  45

Phe Pro Arg Thr Cys Ile Pro Ser Phe Pro Arg Thr Cys Ile Pro Ser
    50                  55                  60

Phe Pro Arg Ala Cys Ile Pro Ser Phe Pro Arg Thr Cys Ile Pro Ser
65                  70                  75                  80

Phe Pro Arg Thr Cys Ile Pro Ser Phe Pro Arg Thr Cys Ile Pro Ser
                85                  90                  95

Phe Pro Arg Thr Cys Ile Pro Ser Phe Pro Arg Thr Cys Ile Pro Ser
            100                 105                 110

Phe Pro Arg Thr Cys Ile Pro Ser Phe Pro Arg Thr Cys Ile Pro Ser
        115                 120                 125

Phe Pro Arg Lys Trp Glu Ser Ser Phe Gly Phe Ala Cys Phe Lys
    130                 135                 140

Phe Arg Val Thr Ser Thr Ser Ser Phe Pro Arg Thr Cys Ile Pro Ser
145                 150                 155                 160

Phe Pro Arg Lys Trp Glu Ser Ser Phe Gly Phe Ala Cys Phe Lys
                165                 170                 175

Phe Arg Val Thr Ser Thr Ser Ser Phe Pro Arg Thr Tyr Ile Pro Ser
            180                 185                 190

Phe Pro Arg Lys Xaa Xaa Thr His Leu Ile Asn
        195                 200

```
<210> SEQ ID NO 53
<211> LENGTH: 1023
<212> TYPE: DNA
<213> ORGANISM: Neisseria meningitidis

<400> SEQUENCE: 53
atgctgacaa aaaggagtt tgagaagttt ttagacgagg tttgcaccgt attgaggcaa      60
gaggcaaaaa acgcaccttt caaatcccaa gatattttg aaaacagagt tcgtgcgctg     120
tgcattgcaa aaattcccgc ttatgctgac atagttatca atcctgaacc tgtgccgcaa    180
attttccccg atgttccaat aggggaatat ggcgtagaag tcaaattcac gctaaaagat    240
acttggcgca gcgtagcaaa cagtatccaa gagaaaaaca aagctgacgg tgtacagcat    300
atctatgtgg tattcggaaa atggggggc attcccgatg tgaaatggca actttacgaa     360
gatagcgtaa ttcatgtccg cacatcgcat gttccgcgct tgaggtaga aatagaatct     420 gatcgaccgt ctctgtttga gggtttcggt atttcctatg ctgaatttgc cgatttggat    480
atgcatgaaa aatgaaata tatccgaaaa tatgcccgta acaggctgaa agaaggcgag    540
cggttatggt ggatagaaga cattgacgca gtagacagcc atgatctgcc tttggaagtg    600
cgcctttaca cttccctgcc gcaggaagaa aaaatccgcc tccgagctga agcagcatta    660 gtctccccc gtattgtctg ctcaggcagg gcgaagcaca aatacgataa tgccgtcctg    720
```

-continued

```
tatctgatta cctatcgcgg tgtgctttgt catcaggcgc gggacttatt cagtgcgggc    780
agcgttgcca actcggcgga agactaccgt ggcggaaact atgtagaaaa atctttaaaa    840
ttgattgagc atgaaattga aaaagctgct ttggaaatgg atgatgctct aattgtcgaa    900
tattggggag aaagcgtccc gacagaaaaa cgcctagagt attggattaa gatgttggat    960
gatttggcag atggctggat accttctgaa tcgctattca atggtaggta taaagccaaa    1020
taa                                                                 1023
```

<210> SEQ ID NO 54
<211> LENGTH: 340
<212> TYPE: PRT
<213> ORGANISM: Neisseria meningitidis

<400> SEQUENCE: 54

| | | | | | | | | | | | | | | |
|---|---|---|---|---|---|---|---|---|---|---|---|---|---|---|
| Met | Leu | Thr | Lys | Lys | Glu | Phe | Glu | Lys | Phe | Leu | Asp | Glu | Val | Cys | Thr |
| 1 | | | | 5 | | | | | 10 | | | | | 15 | |
| Val | Leu | Arg | Gln | Glu | Ala | Lys | Asn | Ala | Pro | Phe | Lys | Ser | Gln | Asp | Ile |
| | | | 20 | | | | | 25 | | | | | 30 | | |
| Phe | Glu | Asn | Arg | Val | Arg | Ala | Leu | Cys | Ile | Ala | Lys | Ile | Pro | Ala | Tyr |
| | | 35 | | | | | 40 | | | | | 45 | | | |
| Ala | Asp | Ile | Val | Ile | Asn | Pro | Glu | Pro | Val | Pro | Gln | Ile | Phe | Pro | Asp |
| 50 | | | | | 55 | | | | | 60 | | | | | |
| Val | Pro | Ile | Gly | Glu | Tyr | Gly | Val | Glu | Val | Lys | Phe | Thr | Leu | Lys | Asp |
| 65 | | | | | 70 | | | | | 75 | | | | | 80 |
| Thr | Trp | Arg | Ser | Val | Ala | Asn | Ser | Ile | Gln | Lys | Asn | Lys | Ala | Asp | |
| | | | | 85 | | | | | 90 | | | | | 95 | |
| Gly | Val | Gln | His | Ile | Tyr | Val | Val | Phe | Gly | Lys | Met | Gly | Ile | Pro | |
| | | | 100 | | | | | 105 | | | | | 110 | | |
| Asp | Val | Lys | Trp | Gln | Leu | Tyr | Glu | Asp | Ser | Val | Ile | His | Val | Arg | Thr |
| | | 115 | | | | | 120 | | | | | 125 | | | |
| Ser | His | Val | Pro | Arg | Phe | Glu | Val | Glu | Ile | Glu | Ser | Asp | Arg | Pro | Ser |
| 130 | | | | | 135 | | | | | 140 | | | | | |
| Leu | Phe | Glu | Gly | Phe | Gly | Ile | Ser | Tyr | Ala | Glu | Phe | Ala | Asp | Leu | Asp |
| 145 | | | | | 150 | | | | | 155 | | | | | 160 |
| Met | His | Glu | Lys | Met | Glu | Tyr | Ile | Arg | Lys | Tyr | Ala | Arg | Asn | Arg | Leu |
| | | | | 165 | | | | | 170 | | | | | 175 | |
| Lys | Glu | Gly | Glu | Arg | Leu | Trp | Trp | Ile | Glu | Asp | Ile | Asp | Ala | Val | Asp |
| | | | 180 | | | | | 185 | | | | | 190 | | |
| Ser | His | Asp | Leu | Pro | Leu | Glu | Val | Arg | Leu | Tyr | Thr | Ser | Leu | Pro | Gln |
| | | 195 | | | | | 200 | | | | | 205 | | | |
| Glu | Glu | Lys | Ile | Arg | Leu | Arg | Ala | Glu | Ala | Ala | Leu | Val | Ser | Pro | Arg |
| 210 | | | | | 215 | | | | | 220 | | | | | |
| Ile | Val | Cys | Ser | Gly | Arg | Ala | Lys | His | Lys | Tyr | Asp | Asn | Ala | Val | Leu |
| 225 | | | | | 230 | | | | | 235 | | | | | 240 |
| Tyr | Leu | Ile | Thr | Tyr | Arg | Gly | Val | Leu | Cys | His | Gln | Ala | Arg | Asp | Leu |
| | | | | 245 | | | | | 250 | | | | | 255 | |
| Phe | Ser | Ala | Gly | Ser | Val | Ala | Asn | Ser | Ala | Glu | Asp | Tyr | Arg | Gly | Gly |
| | | | 260 | | | | | 265 | | | | | 270 | | |
| Asn | Tyr | Val | Glu | Lys | Ser | Leu | Lys | Leu | Ile | Glu | His | Glu | Ile | Glu | Lys |
| | | 275 | | | | | 280 | | | | | 285 | | | |
| Ala | Ala | Leu | Glu | Met | Asp | Asp | Ala | Leu | Ile | Val | Glu | Tyr | Trp | Gly | Glu |
| | 290 | | | | | 295 | | | | | 300 | | | | |
| Ser | Val | Pro | Thr | Glu | Lys | Arg | Leu | Glu | Tyr | Trp | Ile | Lys | Met | Leu | Asp |
| 305 | | | | | 310 | | | | | 315 | | | | | 320 |

```
Asp Leu Ala Asp Gly Trp Ile Pro Ser Glu Ser Leu Phe Asn Gly Arg
            325                 330                 335

Tyr Lys Ala Lys
            340

<210> SEQ ID NO 55
<211> LENGTH: 1131
<212> TYPE: DNA
<213> ORGANISM: Neisseria meningitidis
<220> FEATURE:
<221> NAME/KEY: misc_feature
<222> LOCATION: 1112, 1113, 1114, 1115, 1116
<223> OTHER INFORMATION: n = A,T,C or G

<400> SEQUENCE: 55
atggtgattt ccaaccccg cgaacttgaa aaactcaaag accggattcc caatctgatc      60
aacatcatcc gcgtcgccat cgtttttccg ctgatgatta tgcacatcct cgggctggaa    120
accggcagcc gtgcgaacct gcacgcttcg tggacggcgt gggcgtttta tgtttggctc    180
gccattgcct gctggctgat tttcttttcc atcatccatc cgcattggca atggcaggct    240
ttgagaatac cgagtttcag cgcggtggcg gacatcacga tgatcggcgt gctgacctac    300
ctgttcggcg catcgactc cggcttcggc atcctgattc tgcccttcgt cgtctgctcc    360
tgcctgctca gctacgggcg ctaccccctg ctctattcca gctacgccgc catcctgctg    420
atattcaacg ccattgccga cggcgatatc aatatgtatc cgctgatttt ggatgcaaaa    480
accgtcacca cacccttcgt cctcgtgacc ggctcctatt cgtcgccat gattgcctcg    540 ctgtcggtca gatacatcga ccgtgccggc aaacttgccc atgaaaacca cgccgcctac    600
cgccgcatca ggggcttgaa ccaaatcgtg ctcaaccgcg ttcaggaagc ggtcgtcatc    660
atcaacgtcg agtatcagac cgtactgttc aataaaaagg caaagatct gctccccacg    720 cttgaaatcg acagcatac cgccctgttc gaccctatta ccgttttatg gacaaggcc    780 ccttcgcgta ctttcgaacg caatatcgac acgcccgccc tgaccgcccg catccgcgcc    840
gtgccgatga caaagagca gaacaagctg ctcatcctct acatccgccc gcaaagcgaa    900
attcaggcag aagccctgtc cgtcaaactt gccgcgctcg gacaactgac cgccaacatc    960
gcccacgaaa tccgcaaccc catgtccgcc atccgccatg caaacgacct gttgcgcgaa   1020
aatatggaag cggggcggc agatccgttc aacgccaaat tgtgcaaaat catcgacggc   1080
aacgtctgcc gtatcgacaa aatgctcgaa gnnnnncaca cacttaatta a           1131

<210> SEQ ID NO 56
<211> LENGTH: 376
<212> TYPE: PRT
<213> ORGANISM: Neisseria meningitidis
<220> FEATURE:
<221> NAME/KEY: VARIANT
<222> LOCATION: 371, 372
<223> OTHER INFORMATION: Xaa = Any Amino Acid

<400> SEQUENCE: 56

Met Val Ile Ser Asn Pro Arg Glu Leu Glu Lys Leu Lys Asp Arg Ile
  1               5                  10                  15

Pro Asn Leu Ile Asn Ile Ile Arg Val Ala Ile Val Phe Pro Leu Met
             20                  25                  30

Ile Met His Ile Leu Gly Leu Glu Thr Gly Ser Arg Ala Asn Leu His
         35                  40                  45

Ala Ser Trp Thr Ala Trp Ala Phe Tyr Val Trp Leu Ala Ile Ala Cys
     50                  55                  60
```

```
Trp Leu Ile Phe Phe Ser Ile Ile His Pro His Trp Gln Trp Gln Ala
 65                  70                  75                  80

Leu Arg Ile Pro Ser Phe Ser Ala Val Ala Asp Ile Thr Met Ile Gly
             85                  90                  95

Val Leu Thr Tyr Leu Phe Gly Gly Ile Asp Ser Gly Phe Gly Ile Leu
            100                 105                 110

Ile Leu Pro Phe Val Val Cys Ser Cys Leu Leu Ser Tyr Gly Arg Tyr
        115                 120                 125

Pro Leu Leu Tyr Ser Ser Tyr Ala Ala Ile Leu Leu Ile Phe Asn Ala
        130                 135                 140

Ile Ala Asp Gly Asp Ile Asn Met Tyr Pro Leu Ile Leu Asp Ala Lys
145                 150                 155                 160

Thr Val Thr Asn Thr Phe Val Leu Val Thr Gly Ser Tyr Phe Val Ala
                165                 170                 175

Met Ile Ala Ser Leu Ser Val Arg Tyr Ile Asp Arg Ala Gly Lys Leu
            180                 185                 190

Ala His Glu Asn His Ala Ala Tyr Arg Arg Ile Arg Gly Leu Asn Gln
        195                 200                 205

Ile Val Leu Asn Arg Val Gln Glu Ala Val Val Ile Ile Asn Val Glu
    210                 215                 220

Tyr Gln Thr Val Leu Phe Asn Lys Lys Ala Lys Asp Leu Leu Pro Thr
225                 230                 235                 240

Leu Glu Ile Gly Gln His Thr Ala Leu Phe Asp Pro Ile Thr Val Leu
                245                 250                 255

Trp Asp Lys Ala Pro Ser Arg Thr Phe Glu Arg Asn Ile Asp Thr Pro
            260                 265                 270

Ala Leu Thr Ala Arg Ile Arg Ala Val Pro Met Asn Lys Glu Gln Asn
        275                 280                 285

Lys Leu Leu Ile Leu Tyr Ile Arg Pro Gln Ser Glu Ile Gln Ala Glu
290                 295                 300

Ala Leu Ser Val Lys Leu Ala Ala Leu Gly Gln Leu Thr Ala Asn Ile
305                 310                 315                 320

Ala His Glu Ile Arg Asn Pro Met Ser Ala Ile Arg His Ala Asn Asp
                325                 330                 335

Leu Leu Arg Glu Asn Met Glu Ala Gly Ala Ala Asp Pro Phe Asn Ala
            340                 345                 350

Lys Leu Cys Lys Ile Ile Asp Gly Asn Val Cys Arg Ile Asp Lys Met
        355                 360                 365

Leu Glu Xaa Xaa His Thr Leu Asn
        370                 375

<210> SEQ ID NO 57
<211> LENGTH: 1041
<212> TYPE: DNA
<213> ORGANISM: Neisseria meningitidis
<220> FEATURE:
<221> NAME/KEY: misc_feature
<222> LOCATION: 8, 9, 10, 11, 12
<223> OTHER INFORMATION: n = A,T,C or G

<400> SEQUENCE: 57
gtgtgtgnnn nnaacacctt cgtcctcgtg accggctcct atttcgtcgc catgattgcc     60
tcgctgtcgg tcagatacat cgaccgtgcc ggcaaacttg cccatgaaaa ccacgccgcc    120
taccgccgca tcgggggctt gaaccaaatc gtgctcaacc gcgttcagga agcggtcgtc    180
atcatcaacg tcgagtatca gaccgtactg ttcaataaaa aggcaaaaga tctgctcccc    240
```

```
acgcttgaaa tcggacagca taccgccctg ttcgacccta ttaccgtttt atgggacaag    300
gccccttcgc gtactttcga acgcaatatc gacacgcccg ccctgaccgc cgcatccgc    360
gccgtgccga tgaacaaaga gcagaacaag ctgctcatcc tctacatccg cccgcaaagc    420
gaaattcagg cagaagccct gtccgtcaaa cttgccgcgc tcggacaact gaccgccaac    480
atcgcccacg aaatccgcaa ccccatgtcc gccatccgcc atgcaaacga cctgttgcgc    540
gaaaatatgg aagcgggggc ggcagatccg ttcaacgcca aattgtgcaa aatcatcgac    600
ggcaacgtct gccgtatcga caaaatgctc gaagatattt cctcgctcaa caagcgcaac    660
aaaaccgaac gcgaaaccat cggcctgata ccgttttggg aagaattcaa acaagagttc    720
ctgctcggcc atcccgatgc cgccggctgc atccgcctag atatgcaggg caatcacctg    780
actgccatt tcgatcctgc ccacctgcgg caaattatgt ggaacctcgc caacaacgcg    840
tggcggcaca gccgcaaaca gcccggctcg atttccgtca ccatccgccc cgcgcaaaaa    900
aacaccgtct gtatcctctt tgccgaccgc ccgaagtgca ggaacacctg ttcgaaccct    960
tttacaccac ggcggaaaac ggcaccggcc tcgggctgta tgtcgcccgc gaactggcgc   1020
acgccaattt cggcgatttg a                                            1041
```

<210> SEQ ID NO 58
<211> LENGTH: 346
<212> TYPE: PRT
<213> ORGANISM: Neisseria meningitidis
<220> FEATURE:
<221> NAME/KEY: VARIANT
<222> LOCATION: 3, 4
<223> OTHER INFORMATION: Xaa = Any Amino Acid

<400> SEQUENCE: 58

Met Cys Xaa Xaa Asn Thr Phe Val Leu Val Thr Gly Ser Tyr Phe Val
1               5                   10                  15

Ala Met Ile Ala Ser Leu Ser Val Arg Tyr Ile Asp Arg Ala Gly Lys
            20                  25                  30

Leu Ala His Glu Asn His Ala Ala Tyr Arg Arg Ile Arg Gly Leu Asn
        35                  40                  45

Gln Ile Val Leu Asn Arg Val Gln Glu Ala Val Val Ile Ile Asn Val
    50                  55                  60

Glu Tyr Gln Thr Val Leu Phe Asn Lys Lys Ala Lys Asp Leu Leu Pro
65                  70                  75                  80

Thr Leu Glu Ile Gly Gln His Thr Ala Leu Phe Asp Pro Ile Thr Val
                85                  90                  95

Leu Trp Asp Lys Ala Pro Ser Arg Thr Phe Glu Arg Asn Ile Asp Thr
            100                 105                 110

Pro Ala Leu Thr Ala Arg Ile Arg Ala Val Pro Met Asn Lys Glu Gln
        115                 120                 125

Asn Lys Leu Leu Ile Leu Tyr Ile Arg Pro Gln Ser Glu Ile Gln Ala
    130                 135                 140

Glu Ala Leu Ser Val Lys Leu Ala Ala Leu Gly Gln Leu Thr Ala Asn
145                 150                 155                 160

Ile Ala His Glu Ile Arg Asn Pro Met Ser Ala Ile Arg His Ala Asn
                165                 170                 175

Asp Leu Leu Arg Glu Asn Met Glu Ala Gly Ala Ala Asp Pro Phe Asn
            180                 185                 190

Ala Lys Leu Cys Lys Ile Ile Asp Gly Asn Val Cys Arg Ile Asp Lys
        195                 200                 205

```
Met Leu Glu Asp Ile Ser Ser Leu Asn Lys Arg Asn Lys Thr Glu Arg
        210                 215                 220
Glu Thr Ile Gly Leu Ile Pro Phe Trp Glu Glu Phe Lys Gln Glu Phe
225                 230                 235                 240
Leu Leu Gly His Pro Asp Ala Ala Gly Cys Ile Arg Leu Asp Met Gln
                245                 250                 255
Gly Asn His Leu Thr Ala Tyr Phe Asp Pro Ala His Leu Arg Gln Ile
            260                 265                 270
Met Trp Asn Leu Ala Asn Asn Ala Trp Arg His Ser Arg Lys Gln Pro
        275                 280                 285
Gly Ser Ile Ser Val Thr Ile Arg Pro Ala Gln Lys Asn Thr Val Cys
    290                 295                 300
Ile Leu Phe Ala Asp Arg Pro Lys Cys Arg Asn Thr Cys Ser Asn Pro
305                 310                 315                 320
Phe Thr Pro Arg Arg Lys Thr Ala Pro Ala Ser Gly Cys Met Ser Pro
                325                 330                 335
Ala Asn Trp Arg Thr Pro Ile Ser Ala Ile
                340                 345

<210> SEQ ID NO 59
<211> LENGTH: 3081
<212> TYPE: DNA
<213> ORGANISM: Neisseria meningitidis

<400> SEQUENCE: 59
atgaataaaa ctttaaaaag gcgggttttc cgccataccg cgctttatgc cgccatcttg      60
atgttttccc ataccggcgg ggggggggg gcgatggcgc aaacccatca atacgctatt     120
atcatgaacg agcgaaagca gcccgaggta aagtcgaatg tgccatcttc aataaaggac     180
aaagacagga aacgcgaata tactcattat aagtacaaaa caggaggagg ctctgtctca     240
ttcaacaata gcgatgagct tgtttctcaa caaagcggta ctgccgtttt tggcacagcc     300
acctacctgc cgccctacgg caaggtttcc ggttttgatg acaaaaggct gaaagagcgc     360
ggcaatgccg ttaattggat tcatacgacc cacccagggt tgataggcta cagctacgcc     420
ggtgtcgtat gcagagacag cacaggctgt cccaaacttg tctataaaac ccgattttcc     480
ttcgataatc ccgacttggc aaaaacagga ggcgggctgg ataggcacac agagccaagc     540
cgcgacaatt cgcccattta caattgaag gatcatccat ggttgggcgt gtctttcaat     600
ttgggcagcg agaataccgt caaaaatggc aactcattca acaaattgat atcttctttt     660
agtgaaaaca ataataatca aaccatcgtc tctacgacag aaagccaccc tatttccctt     720
ggcgacgggc agcgcgaaca taccgccgtg gtctattatc tgaacgccaa actgcacctg     780
ctggacaaaa aagggattaa agatatcacc gacaaaacag tgcagttggg tgtcttgaag     840
ccgagcatcg atgtgcggaa aggtgccggc tggctaagtt tttgggctag ttgggacatt     900
aaagataccg ggcagattcc agtcaagctc ggcctgcagc aagtcaaagc aggccgctgc     960
atcaataaac cgaaccccaa tcccaaagcc aagcccttt ccccgcact gactgccccc    1020 gcgctgtggt tcggacctgt gcaaaatggt aagatggaga tgtattccgc ttcggtttct    1080 acctacccg acagttcgag cagccgcatc ttccttcaaa atctgaaaag aaaaaacgac    1140
cccaacaaac ccggccgcta ttccctcgca gacttgagcg cgtcggagat taaaagtaaa    1200
gagccgactt tcacagggcg gcaaaccgtc atccgattgg ataaaggcgt acatcagatc    1260
aaacttaaag gcaatgaggt cgaaggtttt aaggaaaaca acggcaacga cactttcggc    1320
attgttagtg aagggagctt catgcctgat gacagcgagt ggaaaaaagt gctgctgcct    1380
```

```
tggacggttc gtgctttcaa tgatgacggt caatttaaca cagtcaacaa agaagaaaac   1440
aacggcaagc caaatacag tcaaaaatac cgcagccgca acaacggcaa gcacgagcgc    1500
aatttgggcg acatcgtcaa cagccccatc gtggcggtcg gcgagtattt ggctacttcc   1560
gccaacgacg ggatggtgca tatcttcaaa aaaagcggcg gggatgaccg caactatagt   1620
ctgaagctca gttatatccc gggcacgatg ccgcgcaagg atattcaaag ccaagactcc   1680
acccttgcca aagagctgcg cgcctttgcc gaaaaaagct atgtgggcga ccgctacggc   1740
gtggacggcg gctttgtctt gcgccaagtc gaatggaaag gcaaaaccg cgtgttatg    1800 ttcggcgcga tgggctttgg cggcagaggt gcatacgcct tggatttgac caaagccgaa   1860
aacggtgacc cgaccgccgt ttccctgttt gatgtcaaac atgacaataa tggcaagaat   1920
agcaataata gcgtgcaatt aggctacacc gtcggcacgc cgcaaatcgg caaaacccac   1980
aacggcaaat acgccgcctt cctcgcctct ggttatgcga ctaaagacat taacaacggc   2040
gacaataaaa ccgcgctgta tgtgtatgat ttggaaagca caacggtac gccgattgca    2100 aaaatcgaag tacccaacgg caagggcggg cttcgtcccc ccacgctggt ggataaagat   2160
ttggacggca cggttgatat cgccatgcc ggcgatcgcg gcggcagtat gtaccgcttt     2220
gatttaagcg gcaacaaccc gaccagttgg tctgcacgcg ccattttcag cggcaacaaa   2280
ccgattactt ccgcgcccgc catttcccaa ctgaaagaca aacgcgtggt catcttcggc    2340
acgggcagtg atttgagtga ggaggatgtg gacagcaaag aaatccaaca cgtttacggt   2400 attttgaca atgaaacaga cacgggtacg gcgaaagacg gcagggcaa cgggctgctc     2460 gagcaagtgc ttagtgagga aaataaaacc ttattcctga ccgattacaa gcgatccgac   2520
ggatcgggca gtaaggggtg ggtagtgaag ctgaaggaag gacagcgcgt taccgtcaaa   2580
ccgaccgtgg tattgcgtac cgcctttgta accatccgca aatataacga cggcggctgc   2640
ggcgcggaaa ccgccatttt gggcatcaat accgccgacg gcggcaagct gaccaagaaa   2700
agcgcgcgcc cgattgtgcc ggacaccaat acggctatcg cgcaatattc cggccataag   2760
aaaggcacca acggcaaatc catccctata ggttgtatgc aaaaaggcaa tgaaatcgtc   2820
tgcccgaacg gatatgttta cgacaaaccg gttaatgtgc gttatctgga tgaaaagaaa   2880
acagacggat tttcaacaac ggcagacggc gatgcgggcg cagcggtat agaccccgcc    2940 ggcaagcgtg ccggcaaaaa caaccgctgc ttctcccaaa aaggggtgcg caccctgctg   3000
atgaacgatt tggacagctt ggacattacc ggcccgatgt gcggtatgaa acgaatcagc   3060
tggcgtgaag tcttctactg a                                            3081
```

<210> SEQ ID NO 60
<211> LENGTH: 1026
<212> TYPE: PRT
<213> ORGANISM: Neisseria meningitidis

<400> SEQUENCE: 60

```
Met Asn Lys Thr Leu Lys Arg Arg Val Phe Arg His Thr Ala Leu Tyr
 1               5                  10                  15

Ala Ala Ile Leu Met Phe Ser His Thr Gly Gly Gly Gly Ala Met
                20                  25                  30

Ala Gln Thr His Gln Tyr Ala Ile Ile Met Asn Glu Arg Lys Gln Pro
            35                  40                  45

Glu Val Lys Ser Asn Val Pro Ser Ser Ile Lys Asp Lys Asp Arg Lys
        50                  55                  60

Arg Glu Tyr Thr His Tyr Lys Tyr Lys Thr Gly Gly Gly Ser Val Ser
```

```
                65                  70                  75                  80
Phe Asn Asn Ser Asp Glu Leu Val Ser Gln Gln Ser Gly Thr Ala Val
                    85                  90                  95

Phe Gly Thr Ala Thr Tyr Leu Pro Pro Tyr Gly Lys Val Ser Gly Phe
               100                 105                 110

Asp Asp Lys Arg Leu Lys Glu Arg Gly Asn Ala Val Asn Trp Ile His
               115                 120                 125

Thr Thr His Pro Gly Leu Ile Gly Tyr Ser Tyr Ala Gly Val Val Cys
           130                 135                 140

Arg Asp Ser Thr Gly Cys Pro Lys Leu Val Tyr Lys Thr Arg Phe Ser
145                 150                 155                 160

Phe Asp Asn Pro Asp Leu Ala Lys Thr Gly Gly Leu Asp Arg His
               165                 170                 175

Thr Glu Pro Ser Arg Asp Asn Ser Pro Ile Tyr Lys Leu Lys Asp His
           180                 185                 190

Pro Trp Leu Gly Val Ser Phe Asn Leu Gly Ser Glu Asn Thr Val Lys
           195                 200                 205

Asn Gly Asn Ser Phe Asn Lys Leu Ile Ser Ser Phe Ser Glu Asn Asn
           210                 215                 220

Asn Asn Gln Thr Ile Val Ser Thr Thr Glu Ser His Pro Ile Ser Leu
225                 230                 235                 240

Gly Asp Gly Gln Arg Glu His Thr Ala Val Val Tyr Tyr Leu Asn Ala
               245                 250                 255

Lys Leu His Leu Leu Asp Lys Lys Gly Ile Lys Asp Ile Thr Asp Lys
               260                 265                 270

Thr Val Gln Leu Gly Val Leu Lys Pro Ser Ile Asp Val Arg Lys Gly
           275                 280                 285

Ala Gly Trp Leu Ser Phe Trp Ala Ser Trp Asp Ile Lys Asp Thr Gly
           290                 295                 300

Gln Ile Pro Val Lys Leu Gly Leu Gln Gln Val Lys Ala Gly Arg Cys
305                 310                 315                 320

Ile Asn Lys Pro Asn Pro Asn Pro Lys Ala Gln Ala Leu Ser Pro Ala
               325                 330                 335

Leu Thr Ala Pro Ala Leu Trp Phe Gly Pro Val Gln Asn Gly Lys Met
               340                 345                 350

Glu Met Tyr Ser Ala Ser Val Ser Thr Tyr Pro Asp Ser Ser Ser Ser
           355                 360                 365

Arg Ile Phe Leu Gln Asn Leu Lys Arg Lys Asn Asp Pro Asn Lys Pro
           370                 375                 380

Gly Arg Tyr Ser Leu Ala Asp Leu Ser Ala Ser Glu Ile Lys Ser Lys
385                 390                 395                 400

Glu Pro Thr Phe Thr Gly Arg Gln Thr Val Ile Arg Leu Asp Lys Gly
               405                 410                 415

Val His Gln Ile Lys Leu Lys Gly Asn Glu Val Glu Gly Phe Lys Gly
               420                 425                 430

Asn Asn Gly Asn Asp Thr Phe Gly Ile Val Ser Glu Gly Ser Phe Met
           435                 440                 445

Pro Asp Asp Ser Glu Trp Lys Lys Val Leu Leu Pro Trp Thr Val Arg
           450                 455                 460

Ala Phe Asn Asp Asp Gly Gln Phe Asn Thr Val Asn Lys Glu Glu Asn
465                 470                 475                 480

Asn Gly Lys Pro Lys Tyr Ser Gln Lys Tyr Arg Ser Arg Asn Asn Gly
               485                 490                 495
```

```
Lys His Glu Arg Asn Leu Gly Asp Ile Val Asn Ser Pro Ile Val Ala
                500                 505                 510

Val Gly Glu Tyr Leu Ala Thr Ser Ala Asn Asp Gly Met Val His Ile
            515                 520                 525

Phe Lys Lys Ser Gly Gly Asp Asp Arg Asn Tyr Ser Leu Lys Leu Ser
        530                 535                 540

Tyr Ile Pro Gly Thr Met Pro Arg Lys Asp Ile Gln Ser Gln Asp Ser
545                 550                 555                 560

Thr Leu Ala Lys Glu Leu Arg Ala Phe Ala Glu Lys Ser Tyr Val Gly
                565                 570                 575

Asp Arg Tyr Gly Val Asp Gly Phe Val Leu Arg Gln Val Glu Trp
            580                 585                 590

Lys Gly Gln Asn Arg Val Phe Met Phe Gly Ala Met Gly Phe Gly Gly
        595                 600                 605

Arg Gly Ala Tyr Ala Leu Asp Leu Thr Lys Ala Glu Asn Gly Asp Pro
        610                 615                 620

Thr Ala Val Ser Leu Phe Asp Val Lys His Asp Asn Asn Gly Lys Asn
625                 630                 635                 640

Ser Asn Asn Ser Val Gln Leu Gly Tyr Thr Val Gly Thr Pro Gln Ile
                645                 650                 655

Gly Lys Thr His Asn Gly Lys Tyr Ala Ala Phe Leu Ala Ser Gly Tyr
            660                 665                 670

Ala Thr Lys Asp Ile Asn Asn Gly Asp Asn Lys Thr Ala Leu Tyr Val
        675                 680                 685

Tyr Asp Leu Glu Ser Asn Asn Gly Thr Pro Ile Ala Lys Ile Glu Val
        690                 695                 700

Pro Asn Gly Lys Gly Gly Leu Ser Ser Pro Thr Leu Val Asp Lys Asp
705                 710                 715                 720

Leu Asp Gly Thr Val Asp Ile Ala Tyr Ala Gly Asp Arg Gly Gly Ser
                725                 730                 735

Met Tyr Arg Phe Asp Leu Ser Gly Asn Asn Pro Thr Ser Trp Ser Ala
            740                 745                 750

Arg Ala Ile Phe Ser Gly Asn Lys Pro Ile Thr Ser Ala Pro Ala Ile
        755                 760                 765

Ser Gln Leu Lys Asp Lys Arg Val Val Ile Phe Gly Thr Gly Ser Asp
        770                 775                 780

Leu Ser Glu Glu Asp Val Asp Ser Lys Glu Ile Gln His Val Tyr Gly
785                 790                 795                 800

Ile Phe Asp Asn Glu Thr Asp Thr Gly Thr Ala Lys Asp Gly Gln Gly
                805                 810                 815

Asn Gly Leu Leu Glu Gln Val Leu Ser Glu Glu Asn Lys Thr Leu Phe
            820                 825                 830

Leu Thr Asp Tyr Lys Arg Ser Asp Gly Ser Gly Ser Lys Gly Trp Val
        835                 840                 845

Val Lys Leu Lys Glu Gly Gln Arg Val Thr Val Lys Pro Thr Val Val
        850                 855                 860

Leu Arg Thr Ala Phe Val Thr Ile Arg Lys Tyr Asn Asp Gly Gly Cys
865                 870                 875                 880

Gly Ala Glu Thr Ala Ile Leu Gly Ile Asn Thr Ala Asp Gly Gly Lys
                885                 890                 895

Leu Thr Lys Lys Ser Ala Arg Pro Ile Val Pro Asp Thr Asn Thr Ala
            900                 905                 910

Ile Ala Gln Tyr Ser Gly His Lys Lys Gly Thr Asn Gly Lys Ser Ile
        915                 920                 925
```

Pro Ile Gly Cys Met Gln Lys Gly Asn Glu Ile Val Cys Pro Asn Gly
                930                 935                 940

Tyr Val Tyr Asp Lys Pro Val Asn Val Arg Tyr Leu Asp Glu Lys Lys
945                 950                 955                 960

Thr Asp Gly Phe Ser Thr Thr Ala Asp Gly Asp Ala Gly Gly Ser Gly
                965                 970                 975

Ile Asp Pro Ala Gly Lys Arg Ala Gly Lys Asn Asn Arg Cys Phe Ser
                980                 985                 990

Gln Lys Gly Val Arg Thr Leu Leu Met Asn Asp Leu Asp Ser Leu Asp
                995                 1000                1005

Ile Thr Gly Pro Met Cys Gly Met Lys Arg Ile Ser Trp Arg Glu Val
                1010                1015                1020

Phe Tyr
1025

<210> SEQ ID NO 61
<211> LENGTH: 1002
<212> TYPE: DNA
<213> ORGANISM: Neisseria meningitidis

<400> SEQUENCE: 61
ttgcctgtaa acaaaatgcc gtctgaaccg ccgttcgggc gtcatttgat ttttgcttct      60
ttgacctgcc tcattgatgc agtatgcaaa aaaagatacc gcaaccaaaa cgtttatata    120
ttatctattc tgtgtatgac taggagtaaa cctgtgaacc gaactacctt ctgctgcctt    180
tctctgaccg ccgccctgat tctgaccgcc tgcagcagcg gaggcggcgg aagcggaggc    240
ggcggtgtcg ccgccgacat cggcgcgggg cttgccgatg cactaaccgc accgctcgac    300
cataaagaca aaggtttgaa atccctgaca ttggaagact ccatttccca aaacggaaca    360
ctgaccctgt cggcacaagg tgcggaaaga actttcaaag ccggcgacaa agacaacagt    420
ctcaacacag gcaaactgaa gaacgacaaa atcagccgct tcgactttat ccgtcaaatc    480
gaagtggacg ggcagctcat taccttggag agcggagagt tccaagtgta caaacaaagc    540
cattccgcct taaccgccct tcagaccgag caagtacaag actcggagca ttccgggaag    600
atggttgcga acgccagttt cagaatcggc gacatagtgg cgaacatac atcttttggc    660 aagcttccca agacgtcat ggcgacatat cgcgggacgg cgttcggttc agacgatgcc    720
ggcggaaaac tgacctacac catagatttc gccgccaagc agggacacgg caaaatcgaa    780
catttgaaat cgccagaact caatgttgac ctggccgccg ccgatatcaa gccggatgaa    840
aaacaccatg ccgtcatcag cggttccgtc ctttacaacc aagccgagaa aggcagttac    900
tctctaggca tctttggcgg gcaagcccag gaagttgccg gcagcgcgga agtggaaacc    960
gcaaacggca tacgccatat cggtcttgcc gccaagcaat aa                      1002

<210> SEQ ID NO 62
<211> LENGTH: 333
<212> TYPE: PRT
<213> ORGANISM: Neisseria meningitidis

<400> SEQUENCE: 62

Met Pro Val Asn Lys Met Pro Ser Glu Pro Pro Phe Gly Arg His Leu
1               5                   10                  15

Ile Phe Ala Ser Leu Thr Cys Leu Ile Asp Ala Val Cys Lys Lys Arg
                20                  25                  30

Tyr Arg Asn Gln Asn Val Tyr Ile Leu Ser Ile Leu Cys Met Thr Arg
                35                  40                  45

Ser Lys Pro Val Asn Arg Thr Thr Phe Cys Cys Leu Ser Leu Thr Ala
            50                  55                  60

Ala Leu Ile Leu Thr Ala Cys Ser Ser Gly Gly Gly Ser Gly Gly
 65                  70                  75                  80

Gly Gly Val Ala Ala Asp Ile Gly Ala Gly Leu Ala Asp Ala Leu Thr
                 85                  90                  95

Ala Pro Leu Asp His Lys Asp Lys Gly Leu Lys Ser Leu Thr Leu Glu
            100                 105                 110

Asp Ser Ile Ser Gln Asn Gly Thr Leu Thr Leu Ser Ala Gln Gly Ala
            115                 120                 125

Glu Arg Thr Phe Lys Ala Gly Asp Lys Asp Asn Ser Leu Asn Thr Gly
            130                 135                 140

Lys Leu Lys Asn Asp Lys Ile Ser Arg Phe Asp Phe Ile Arg Gln Ile
145                 150                 155                 160

Glu Val Asp Gly Gln Leu Ile Thr Leu Glu Ser Gly Glu Phe Gln Val
                165                 170                 175

Tyr Lys Gln Ser His Ser Ala Leu Thr Ala Leu Gln Thr Glu Gln Val
            180                 185                 190

Gln Asp Ser Glu His Ser Gly Lys Met Val Ala Lys Arg Gln Phe Arg
            195                 200                 205

Ile Gly Asp Ile Val Gly Glu His Thr Ser Phe Gly Lys Leu Pro Lys
            210                 215                 220

Asp Val Met Ala Thr Tyr Arg Gly Thr Ala Phe Gly Ser Asp Asp Ala
225                 230                 235                 240

Gly Gly Lys Leu Thr Tyr Thr Ile Asp Phe Ala Ala Lys Gln Gly His
                245                 250                 255

Gly Lys Ile Glu His Leu Lys Ser Pro Glu Leu Asn Val Asp Leu Ala
            260                 265                 270

Ala Ala Asp Ile Lys Pro Asp Glu Lys His His Ala Val Ile Ser Gly
            275                 280                 285

Ser Val Leu Tyr Asn Gln Ala Glu Lys Gly Ser Tyr Ser Leu Gly Ile
            290                 295                 300

Phe Gly Gly Gln Ala Gln Glu Val Ala Gly Ser Ala Glu Val Glu Thr
305                 310                 315                 320

Ala Asn Gly Ile Arg His Ile Gly Leu Ala Ala Lys Gln
                325                 330

<210> SEQ ID NO 63
<211> LENGTH: 690
<212> TYPE: DNA
<213> ORGANISM: Neisseria meningitidis

<400> SEQUENCE: 63
gtgggcgaga tggaaaaaga cgcggatatt gccgcgatgg gttcctattt ggagattttg      60
gcggaagaaa acaataaaag cgtgcttgcc gccattgccc gaaacggcga aatttggaaa     120
aaccccctga cccatcagga aatcacgtct gccttccccc tccgcaaccc catacacaac     180
aacacgatga ttatgcggcg cagcgtcatt gacggcggtt tgcggttcga tcccgcctat     240
atccacgccg aagactataa gttttggtac gaagccggca aattgggcag gctggcgaat     300 tacccccgaag ccttggtcaa ataccgtttc atcaagacc agacttcttc caaacacaac     360
ctgcaacagc gtaagacggc gtggaaaatc aagaagaaa tcagggcggg gtattggaag     420
gcggcaggca taaccgtcgg gtcggactgc ctgaattacg gcttttgaa atcaacggca     480 tatgcgttgc acgaaaaagc cttgtccgga caggatatcg gatacctccg cctgttcctg     540

```
tacgaatatt tcttgtcgtt ggaaaagtat tctttgaccg atttactgga ttttctgaca    600
gaccgcgtga tgaggaagct gtttgccgca ccgcaatata ggaaaatcct gaaaaaaatg    660
ttacgccctt ggaaataccg gggctattga                                     690
```

<210> SEQ ID NO 64
<211> LENGTH: 229
<212> TYPE: PRT
<213> ORGANISM: Neisseria meningitidis

<400> SEQUENCE: 64

```
Met Gly Glu Met Glu Lys Asp Ala Asp Ile Ala Ala Met Gly Ser Tyr
 1               5                  10                  15

Leu Glu Ile Leu Ala Glu Glu Asn Asn Lys Ser Val Leu Ala Ala Ile
             20                  25                  30

Ala Arg Asn Gly Glu Ile Trp Lys Asn Pro Leu Thr His Gln Glu Ile
         35                  40                  45

Thr Ser Ala Phe Pro Leu Arg Asn Pro Ile His Asn Asn Thr Met Ile
     50                  55                  60

Met Arg Arg Ser Val Ile Asp Gly Gly Leu Arg Phe Asp Pro Ala Tyr
 65                  70                  75                  80

Ile His Ala Glu Asp Tyr Lys Phe Trp Tyr Glu Ala Gly Lys Leu Gly
                 85                  90                  95

Arg Leu Ala Asn Tyr Pro Glu Ala Leu Val Lys Tyr Arg Phe His Gln
            100                 105                 110

Asp Gln Thr Ser Ser Lys His Asn Leu Gln Gln Arg Lys Thr Ala Trp
        115                 120                 125

Lys Ile Lys Glu Glu Ile Arg Ala Gly Tyr Trp Lys Ala Ala Gly Ile
    130                 135                 140

Thr Val Gly Ser Asp Cys Leu Asn Tyr Gly Leu Leu Lys Ser Thr Ala
145                 150                 155                 160

Tyr Ala Leu His Glu Lys Ala Leu Ser Gly Gln Asp Ile Gly Tyr Leu
                165                 170                 175

Arg Leu Phe Leu Tyr Glu Tyr Phe Leu Ser Leu Glu Lys Tyr Ser Leu
            180                 185                 190

Thr Asp Leu Leu Asp Phe Leu Thr Asp Arg Val Met Arg Lys Leu Phe
        195                 200                 205

Ala Ala Pro Gln Tyr Arg Lys Ile Leu Lys Lys Met Leu Arg Pro Trp
    210                 215                 220

Lys Tyr Arg Gly Tyr
225
```

<210> SEQ ID NO 65
<211> LENGTH: 627
<212> TYPE: DNA
<213> ORGANISM: Neisseria meningitidis

<400> SEQUENCE: 65

```
atgacgcaag aacgtttacc cgaattttc gaccgcgccc cgacgctgac cgtacaagac     60
ccgcttgccg cattcctcgg cgcggccgaa acggcatcc tcacttaccg ctacgccgat    120
gccgtgcgcc tgtgcggaca ttcctgcccg accgtcgcgg gcgcgtacct gatggttatc    180
aaaggtctga agcccttta cggcgaagag ctgcccgaac gcggcggcat cgaagccgcc    240
atgcagggag cgcgcgacga aggcacggtc ggcgtaaccg catccgtcgt ccaactcctc    300
accggcgcag cccccgaaac cggcttcgga ggcatcggaa tacagggacg cttcgcccgc    360
```

```
cgcaacctct tatcctttgg tgcaggcgaa atcaacggca cactcgcgct ccgccgccgc    420
gacaccggca aaaccgtcgc cgtcagcctc aacgccgccc tgcaacccct tcgcaccgcaa   480 atgcgcgaca tcatgcccaa agccgtcagc ggcagcgcaa gtaccgacga actcaaacac    540
ttcggacaac tctggcaggc acgcgttaaa gcattttga ccgaatcggc ggacgacccg     600
cagttcgtca tcgtccgcga agtgtga                                        627
```

```
<210> SEQ ID NO 66
<211> LENGTH: 208
<212> TYPE: PRT
<213> ORGANISM: Neisseria meningitidis

<400> SEQUENCE: 66

Met Thr Gln Glu Arg Leu Pro Glu Phe Phe Asp Arg Ala Pro Thr Leu
1               5                   10                  15

Thr Val Gln Asp Pro Leu Ala Ala Phe Leu Gly Ala Ala Glu Asn Gly
            20                  25                  30

Ile Leu Thr Tyr Arg Tyr Ala Asp Ala Val Arg Leu Cys Gly His Ser
        35                  40                  45

Cys Pro Thr Val Ala Gly Ala Tyr Leu Met Val Ile Lys Gly Leu Lys
    50                  55                  60

Ala Leu Tyr Gly Glu Glu Leu Pro Glu Arg Gly Gly Ile Glu Ala Ala
65                  70                  75                  80

Met Gln Gly Ala Arg Asp Glu Gly Thr Val Gly Val Thr Ala Ser Val
                85                  90                  95

Val Gln Leu Leu Thr Gly Ala Ala Pro Glu Thr Gly Phe Gly Gly Ile
            100                 105                 110

Gly Ile Gln Gly Arg Phe Ala Arg Arg Asn Leu Leu Ser Phe Gly Ala
        115                 120                 125

Gly Glu Ile Asn Gly Thr Leu Ala Leu Arg Arg Arg Asp Thr Gly Lys
    130                 135                 140

Thr Val Ala Val Ser Leu Asn Ala Ala Leu Gln Pro Phe Ala Pro Gln
145                 150                 155                 160

Met Arg Asp Ile Met Pro Lys Ala Val Ser Gly Ser Ala Ser Thr Asp
                165                 170                 175

Glu Leu Lys His Phe Gly Gln Leu Trp Gln Ala Arg Val Lys Ala Phe
            180                 185                 190

Leu Thr Glu Ser Ala Asp Asp Pro Gln Phe Val Ile Val Arg Glu Val
        195                 200                 205
```

```
<210> SEQ ID NO 67
<211> LENGTH: 1431
<212> TYPE: DNA
<213> ORGANISM: Neisseria meningitidis
<220> FEATURE:
<221> NAME/KEY: misc_feature
<222> LOCATION: 6, 7, 8, 9, 10
<223> OTHER INFORMATION: n = A,T,C or G

<400> SEQUENCE: 67
gtgtgnnnnn cgaacggttt ggatgcccgt ttacgcgatg atatgcaggc aaaacactac    60
gaaccgggtg gtaaatacca tctgtttggt aatgctcgcg gcagtgttaa aaatcgggtt   120
tacgccgtcc aaacatttga tgcaactgcg gtcggcccca tactgcctat tacacacgaa   180
cggacaggat ttgaaggtgt tatcggctat gaaacccatt tttcagggca cggacatgaa   240
gtacacagtc cgttcgataa tcatgattca agaagcactt ctgatttcag cggcggtgta   300
gacggtggtt ttactgttta ccaacttcat cggacagggt cggaaatcca tccggaggat   360
```

```
ggatatgacg gaccgcaagg cagcgattat ccgcccccg gaggagcaag ggatatatac    420
agctactatg tcaaaggaac ttctacaaaa acaaagataa acactgttcc gcaagcccca    480
ttttcagacc gttggctaaa agaaaatgcc ggtgccgcct ctggttttct cagccgtgcg    540
gatgaagcag gaaaactgat atgggaaaac gaccccaatc aaaattggtg gggtaaccgt    600
atggatgata ttcgcggcat catccaaggt gcagccaatc ctttttctaac gggttttcag    660 ggattgggag ttggggcaat tacagacagt gcggtaaacc cggtaaccta tgcggcagca    720
cggaaaactt tacagggtat tcacaattta ggaaatttaa gtccggaagc acaacttgcg    780
gccgcaaccg cattacaaga cagtgctttt gcggtaaaag acagtatcaa ctctgccaga    840
caatgggctg atgcccatcc gaataaact gcaacagccc aaactgccct ttccgtagca    900
gaggccgcag gtacggtttg ggcggtaaaa aagtagaaac ttaacccgac taaatgggat    960
tgggttaaaa ataccgatta taaaacacct gctgcccgac ctatgcagac tttagatggg   1020
gaaatggccg gtgggaataa accgcctaaa tctataacgt ctggaggaaa agccaatgct   1080
gcaacttatc ctcaattagt taatcaatta actgggcaaa acttaaaaaa cattgcggct   1140
caagatccaa gattgagtct agctcttcat aagagtgaaa aaaattttcc aataggaact   1200
gcaacttatg aagaggcaga taggctaggt aaaatttggg ttggtgaggg tgcaagacaa   1260
actagtggag gcggatggtt aagtatagat ggcactcgac aatatcggcc accaacagaa   1320
aaaaattcac aatttgcaac tacaggtatt caagcaaatt ttgaaactta ctattgat     1380 tcaaatggaa aaaggaataa aattaaaaat ggacatttaa atattaggta a            1431
```

<210> SEQ ID NO 68  
<211> LENGTH: 476  
<212> TYPE: PRT  
<213> ORGANISM: Neisseria meningitidis  
<220> FEATURE:  
<221> NAME/KEY: VARIANT  
<222> LOCATION: 2, 3, 4  
<223> OTHER INFORMATION: Xaa = Any Amino Acid

<400> SEQUENCE: 68

```
Met Xaa Xaa Xaa Asn Gly Leu Asp Ala Arg Leu Arg Asp Asp Met Gln
 1               5                  10                  15

Ala Lys His Tyr Glu Pro Gly Gly Lys Tyr His Leu Phe Gly Asn Ala
             20                  25                  30

Arg Gly Ser Val Lys Asn Arg Val Tyr Ala Val Gln Thr Phe Asp Ala
         35                  40                  45

Thr Ala Val Gly Pro Ile Leu Pro Ile Thr His Glu Arg Thr Gly Phe
     50                  55                  60

Glu Gly Val Ile Gly Tyr Glu Thr His Phe Ser Gly His Gly His Glu
 65                  70                  75                  80

Val His Ser Pro Phe Asp Asn His Asp Ser Arg Ser Thr Ser Asp Phe
                 85                  90                  95

Ser Gly Gly Val Asp Gly Gly Phe Thr Val Tyr Gln Leu His Arg Thr
            100                 105                 110

Gly Ser Glu Ile His Pro Glu Asp Gly Tyr Asp Gly Pro Gln Gly Ser
        115                 120                 125

Asp Tyr Pro Pro Pro Gly Gly Ala Arg Asp Ile Tyr Ser Tyr Tyr Val
    130                 135                 140

Lys Gly Thr Ser Thr Lys Thr Lys Ile Asn Thr Val Pro Gln Ala Pro
145                 150                 155                 160

Phe Ser Asp Arg Trp Leu Lys Glu Asn Ala Gly Ala Ala Ser Gly Phe
```

```
                    165                 170                 175
Leu Ser Arg Ala Asp Glu Ala Gly Lys Leu Ile Trp Glu Asn Asp Pro
            180                 185                 190

Asn Gln Asn Trp Trp Gly Asn Arg Met Asp Asp Ile Arg Gly Ile Ile
        195                 200                 205

Gln Gly Ala Ala Asn Pro Phe Leu Thr Gly Phe Gln Gly Leu Gly Val
    210                 215                 220

Gly Ala Ile Thr Asp Ser Ala Val Asn Pro Val Thr Tyr Ala Ala Ala
225                 230                 235                 240

Arg Lys Thr Leu Gln Gly Ile His Asn Leu Gly Asn Leu Ser Pro Glu
                245                 250                 255

Ala Gln Leu Ala Ala Ala Thr Ala Leu Gln Asp Ser Ala Phe Ala Val
            260                 265                 270

Lys Asp Ser Ile Asn Ser Ala Arg Gln Trp Ala Asp Ala His Pro Asn
        275                 280                 285

Ile Thr Ala Thr Ala Gln Thr Ala Leu Ser Val Ala Glu Ala Ala Gly
    290                 295                 300

Thr Val Trp Gly Gly Lys Lys Val Glu Leu Asn Pro Thr Lys Trp Asp
305                 310                 315                 320

Trp Val Lys Asn Thr Asp Tyr Lys Thr Pro Ala Ala Arg Pro Met Gln
                325                 330                 335

Thr Leu Asp Gly Glu Met Ala Gly Gly Asn Lys Pro Pro Lys Ser Ile
            340                 345                 350

Thr Ser Gly Gly Lys Ala Asn Ala Ala Thr Tyr Pro Gln Leu Val Asn
        355                 360                 365

Gln Leu Thr Gly Gln Asn Leu Lys Asn Ile Ala Ala Gln Asp Pro Arg
    370                 375                 380

Leu Ser Leu Ala Leu His Lys Ser Glu Lys Asn Phe Pro Ile Gly Thr
385                 390                 395                 400

Ala Thr Tyr Glu Glu Ala Asp Arg Leu Gly Lys Ile Trp Val Gly Glu
                405                 410                 415

Gly Ala Arg Gln Thr Ser Gly Gly Gly Trp Leu Ser Ile Asp Gly Thr
            420                 425                 430

Arg Gln Tyr Arg Pro Pro Thr Glu Lys Asn Ser Gln Phe Ala Thr Thr
        435                 440                 445

Gly Ile Gln Ala Asn Phe Glu Thr Tyr Thr Ile Asp Ser Asn Gly Lys
    450                 455                 460

Arg Asn Lys Ile Lys Asn Gly His Leu Asn Ile Arg
465                 470                 475

<210> SEQ ID NO 69
<211> LENGTH: 690
<212> TYPE: DNA
<213> ORGANISM: Neisseria meningitidis
<220> FEATURE:
<221> NAME/KEY: misc_feature
<222> LOCATION: 675, 676, 677, 678, 679
<223> OTHER INFORMATION: n = A,T,C or G

<400> SEQUENCE: 69
gtgggcatca atgccaatcc taactgtgct gatgaagcag gaaaactgat atgggaaaac      60
gaccccaata aaaattggtg ggctaaccgt atgatgata ttcgcggcat cgtccaaggt     120
gcggttaatc cttttttaat ggggttttcaa ggagtaggga ttggggcaat tacagacagt    180
gcagtaagcc cggtcacaga tacagccgcg cagcagactc tacaaggtat taatcattta    240
ggaaatttaa gtcccgaagc acaacttgcg gctgcaaccg cattacaaga cagtgctttt    300
```

```
gcggtaaaag acggtatcaa ttccgccaga caatgggctg atgcccatcc gaatataact    360
gcaacagccc aaactgccct tgccgtagca gaggccgcag gtacggtttg cgcggtaaa     420 aaagtaaacc ttaacccgac caagtgggat tgggttaaaa ataccggcta taaaacacct    480
gctgcccgac ctatgcagac tttagatggg gagatggcag ggggaatag accgcctaaa    540 tctataacgt ccaacagcaa agcagatgct tccacacaac cgtctttaca agcgcaacta    600
attggagaac aaattagtag tgggcatgct tataacaagc atgtcataag acaacaagaa    660
tttacggatt taaannnnnc acacacttaa                                    690
```

<210> SEQ ID NO 70
<211> LENGTH: 229
<212> TYPE: PRT
<213> ORGANISM: Neisseria meningitidis
<220> FEATURE:
<221> NAME/KEY: VARIANT
<222> LOCATION: 225, 226, 227
<223> OTHER INFORMATION: Xaa = Any Amino Acid

<400> SEQUENCE: 70

```
Met Gly Ile Asn Ala Asn Pro Asn Cys Ala Asp Glu Ala Gly Lys Leu
 1               5                  10                  15

Ile Trp Glu Asn Asp Pro Asn Lys Asn Trp Trp Ala Asn Arg Met Asp
            20                  25                  30

Asp Ile Arg Gly Ile Val Gln Gly Ala Val Asn Pro Phe Leu Met Gly
        35                  40                  45

Phe Gln Gly Val Gly Ile Gly Ala Ile Thr Asp Ser Ala Val Ser Pro
    50                  55                  60

Val Thr Asp Thr Ala Ala Gln Gln Thr Leu Gln Gly Ile Asn His Leu
65                  70                  75                  80

Gly Asn Leu Ser Pro Glu Ala Gln Leu Ala Ala Thr Ala Leu Gln
                85                  90                  95

Asp Ser Ala Phe Ala Val Lys Asp Gly Ile Asn Ser Ala Arg Gln Trp
            100                 105                 110

Ala Asp Ala His Pro Asn Ile Thr Ala Thr Ala Gln Thr Ala Leu Ala
        115                 120                 125

Val Ala Glu Ala Ala Gly Thr Val Trp Arg Gly Lys Lys Val Asn Leu
    130                 135                 140

Asn Pro Thr Lys Trp Asp Trp Val Lys Asn Thr Gly Tyr Lys Thr Pro
145                 150                 155                 160

Ala Ala Arg Pro Met Gln Thr Leu Asp Gly Glu Met Ala Gly Gly Asn
                165                 170                 175

Arg Pro Pro Lys Ser Ile Thr Ser Asn Ser Lys Ala Asp Ala Ser Thr
            180                 185                 190

Gln Pro Ser Leu Gln Ala Gln Leu Ile Gly Glu Gln Ile Ser Ser Gly
        195                 200                 205

His Ala Tyr Asn Lys His Val Ile Arg Gln Gln Glu Phe Thr Asp Leu
    210                 215                 220

Xaa Xaa Xaa His Thr
225
```

<210> SEQ ID NO 71
<211> LENGTH: 1299
<212> TYPE: DNA
<213> ORGANISM: Neisseria meningitidis

<400> SEQUENCE: 71

```
atgaagggga tgatgatgtt tgaacgcagt gtgattgcaa tggcttgtat ttttgccctt    60
tcagcctgtg gggcggcgg tggcggatcg cccgatgtta atcggcgga cacgctgtca   120
aaaccggccg ctcctgttgt tgctgaaaaa gagacagagg taaagaaga tgcgccacag   180
gcaggttctc aaggacaggg tgcgccatcc acacaaggca gccaagatat ggcggcagtt   240
tcggcagaaa atacaggcaa tggcggtgcg gcaacaacgg acaaacccaa aaatgaagac   300
gagggaccgc aaaatgatat gctgcaaaat tccgccgaat ccgcaaatca acagggaac   360
aaccaacccg ccgattcttc agattccgcc ccgcgtcaa accctgcacc tgcgaatggc   420
ggtagcaatt ttggaagggt tgatttggct aatggcgttt tgattgatgg ccgtcgcaa   480
aatataacgt tgacccactg taaaggcgat tcttgtaatg gtgataattt attggatgaa   540
gaagcaccgt caaaatcaga atttgaaaat ttaaatgagt ctgaacgaat tgagaaatat   600
aagaaagatg ggaaaagcga taaatttact aatttggttg cgacagcagt tcaagctaat   660
ggaactaaca aatatgtcat catttataaa gacaagtccg cttcatcttc atttgcgcga   720
ttcaggcgtt ctgcacggtc gaggaggtcg cttcctgccg agatgccgct aatccccgtc   780
aatcaggcgg atacgctgat tgtcgatggg gaagcggtca gcctgacggg gcattccggc   840
aatatcttcg cgcccgaagg gaattaccgg tatctgactt acggggcgga aaaattgccc   900
ggcggatcgt atgccctccg tgtgcaaggc gaaccggcaa aggcgaaat gcttgctggc   960
acggccgtgt acaacggcga agtgctgcat tttcatacgg aaaacggccg tccgtacccg  1020
actagaggca ggtttgccgc aaaagtcgat ttcggcagca atctgtgga cggcattatc  1080
gacagcggcg atgatttgca tatgggtacg caaaaattca agccgccat cgatggaaac  1140
ggctttaagg ggacttggac ggaaaatggc ggcggggatg tttccggaag gttttatggc  1200
ccggccggcg aggaagtggc ggggaaatac agctatcgcc cgacagatgc ggaaaagggc  1260
ggattcggcg tgtttgccgg caaaaaagag caggattga                         1299
```

<210> SEQ ID NO 72
<211> LENGTH: 432
<212> TYPE: PRT
<213> ORGANISM: Neisseria meningitidis

<400> SEQUENCE: 72

```
Met Lys Gly Met Met Phe Glu Arg Ser Val Ile Ala Met Ala Cys
1               5                   10                  15

Ile Phe Ala Leu Ser Ala Cys Gly Gly Gly Gly Gly Ser Pro Asp
                20                  25                  30

Val Lys Ser Ala Asp Thr Leu Ser Lys Pro Ala Ala Pro Val Val Ala
            35                  40                  45

Glu Lys Glu Thr Glu Val Lys Glu Asp Ala Pro Gln Ala Gly Ser Gln
        50                  55                  60

Gly Gln Gly Ala Pro Ser Thr Gln Gly Ser Gln Asp Met Ala Ala Val
65                  70                  75                  80

Ser Ala Glu Asn Thr Gly Asn Gly Gly Ala Ala Thr Thr Asp Lys Pro
                85                  90                  95

Lys Asn Glu Asp Glu Gly Pro Gln Asn Asp Met Leu Gln Asn Ser Ala
            100                 105                 110

Glu Ser Ala Asn Gln Thr Gly Asn Asn Gln Pro Ala Asp Ser Ser Asp
        115                 120                 125

Ser Ala Pro Ala Ser Asn Pro Ala Pro Ala Asn Gly Gly Ser Asn Phe
    130                 135                 140

Gly Arg Val Asp Leu Ala Asn Gly Val Leu Ile Asp Gly Pro Ser Gln
```

```
                145                 150                 155                 160
Asn Ile Thr Leu Thr His Cys Lys Gly Asp Ser Cys Asn Gly Asp Asn
                    165                 170                 175

Leu Leu Asp Glu Glu Ala Pro Ser Lys Ser Glu Phe Glu Asn Leu Asn
                180                 185                 190

Glu Ser Glu Arg Ile Glu Lys Tyr Lys Lys Asp Gly Lys Ser Asp Lys
            195                 200                 205

Phe Thr Asn Leu Val Ala Thr Ala Val Gln Ala Asn Gly Thr Asn Lys
        210                 215                 220

Tyr Val Ile Ile Tyr Lys Asp Lys Ser Ala Ser Ser Phe Ala Arg
225                 230                 235                 240

Phe Arg Arg Ser Ala Arg Ser Arg Arg Ser Leu Pro Ala Glu Met Pro
                245                 250                 255

Leu Ile Pro Val Asn Gln Ala Asp Thr Leu Ile Val Asp Gly Glu Ala
                260                 265                 270

Val Ser Leu Thr Gly His Ser Gly Asn Ile Phe Ala Pro Glu Gly Asn
            275                 280                 285

Tyr Arg Tyr Leu Thr Tyr Gly Ala Glu Lys Leu Pro Gly Gly Ser Tyr
        290                 295                 300

Ala Leu Arg Val Gln Gly Glu Pro Ala Lys Gly Glu Met Leu Ala Gly
305                 310                 315                 320

Thr Ala Val Tyr Asn Gly Glu Val Leu His Phe His Thr Glu Asn Gly
                325                 330                 335

Arg Pro Tyr Pro Thr Arg Gly Arg Phe Ala Ala Lys Val Asp Phe Gly
                340                 345                 350

Ser Lys Ser Val Asp Gly Ile Ile Asp Ser Gly Asp Asp Leu His Met
            355                 360                 365

Gly Thr Gln Lys Phe Lys Ala Ala Ile Asp Gly Asn Gly Phe Lys Gly
        370                 375                 380

Thr Trp Thr Glu Asn Gly Gly Asp Val Ser Gly Arg Phe Tyr Gly
385                 390                 395                 400

Pro Ala Gly Glu Glu Val Ala Gly Lys Tyr Ser Tyr Arg Pro Thr Asp
                405                 410                 415

Ala Glu Lys Gly Gly Phe Gly Val Phe Ala Gly Lys Lys Glu Gln Asp
                420                 425                 430

<210> SEQ ID NO 73
<211> LENGTH: 2430
<212> TYPE: DNA
<213> ORGANISM: Neisseria meningitidis

<400> SEQUENCE: 73
atgcggttct caaggtttga gcccaaaggt cgtctgaaac aacaaatacg gtttcagacg      60
acctttcttt caacaagcca ccacggcaat cagacaaaag cagcacatcg ccacatccat     120
gtcggcagta cggccggcac aaccaccatc cgcagcggcg gggataccac cctcaaaggt     180
gcgcagctca tcggcaaagg catacaggca gatacgcgca acctgcatat agaaagtgta     240
caagatactg aaacctctca gagcaaacag caaaacggca atgtccaagt tactgtcggt     300
tacggattca gtgcaagcgg cagttacagc caaagcaaag tcaaagcaga ccatgcctcc     360
gtaaccgagc aaagcggtat ttatgccgga gaagacggct atcaaatcaa ggtcggaaac     420
catacagacc tcaagggcgg tatcatcacc tccggcaaga gtgccgaaga caaggaaaa     480 aaccttttc agacgccac ccttactgcc agcgacattc aaaaccacag ccgctacgaa     540
ggcagaagct tcggcatagg cggcagtttc gacctgaacg gcggctggga cggcacggtt     600
```

```
accgacaaac aaggcaggcc taccgacagg ataagcctgg cagccggcta cggcagcgac    660
agcgacagtc aaagcagcat cacaaaaagc ggcatcaaca cccgcaacat acacatcacc    720
gacgaagcgg acaacttgc ccgaacaggc aggactgcaa agaaaccga agcgcgtatc     780 tacaccggca tcgacaccga actgcggat caacacacag gccgtctgaa aaacagcttc    840
gacaaagacg cggtcgccaa agagatcaac ctgcaaaggg aagtaacgaa ggagttcggc    900
agaaacgccg cccaagccgt agcggccgtt gccgacaaac tcggtaatac ccaaagttac    960
gaacggtatc aggaagcccg aaccctgctg gaggccgaac tgcaaaacac ggacagcaaa   1020
gccgaaaaag ccgccatccg cgcatccctc ggccaagtaa acgcctatct tgccgaaaac   1080
caaagccgct acgacacctg gaaagaaggc ggcataggca ggagcatact gcacggggcg   1140
gcaggcggac tgacgaccgg aagcctcggc ggcatactgg ccggcagcgg cacttcccett   1200 gctgcaccat atttggacaa agcggcggaa acctcggtc cggcgggcaa agcggcggtc    1260
aacgcactgg gcggggcggt catcggctat gcggcgggcg ggaatgtcgg tacggcggca    1320 gtggggcga atgtcgattg aacaataggc agctgcatc cgaaagaaac acaaatcctt    1380
aacaaactgt caaaggcaa atcggctgaa gaacagtacc gcctaaaagc cgctgcatgt    1440
gcattaaccc ggtgcgcgga aggcgtacct gacttcgacc ctctttataa aggactaaaa   1500
aacctccaag atgccggtaa acagtttgta gcggaacaaa acgtattgat gcggacggat    1560
gcatttaaat atggaacatg gaacagcctg aatgatatac gcagcagtta cgaccgtgct    1620
gccaccaaaa ttaagggtgc gggcaatatg ggattgggtg caacgacttt tgtcggttcg    1680
ggtgctatag gcggaggtct gtgcagtacc gggattggct gtgcggccgg tggacttatt    1740
gcaacggcag gtatgaccgg tggttataca caggcctcag aaggaagccg gcaattgttt    1800
ggcacttacc agtccgattt tggtaaaaaa gttgtcctat ctttgggtac accaatagaa    1860
tacgaatcgc cgttagtatc tgatgcgaaa aatctagccg tatggggatt ggaaacgctg    1920
attacgcgca aattgggaaa cttggcaacg ggtgtgaaaa cttccttgac tccgaaaact    1980
gctgacgtac agcgaaatat cctgtcccaa tccgaagtcg gtatcaagtg gggcaagggg    2040
attgaaggac agggaatgcc ttgggaggat tatgtcggta agggcttgtc tgccaatgca    2100
aggttaccta aaaatttaa acatttgat tattttgatc gtggtacagg cacggcaatc     2160
agtgccaaaa ctctggatac gcaaactacg gcacgcctgt ccaaacccga acagctttac    2220
agtaccatga aagggtacat cgataagacg gcaaatttca aaagttatga attatcagaa    2280
gtaccgttaa gggcagacat gatcaaacag cgcgaaatcc atctggccat acccgcacaa    2340
actaataagg agcaaagatt gcagttgcaa cgtgtggtag agtatggcaa aagtcaaaac    2400
attacagtca aaattacgga gatcgaataa                                    2430
```

<210> SEQ ID NO 74  
<211> LENGTH: 809  
<212> TYPE: PRT  
<213> ORGANISM: Neisseria meningitidis

<400> SEQUENCE: 74

```
Met Arg Phe Ser Arg Phe Glu Pro Lys Gly Arg Leu Lys Gln Gln Ile
 1               5                  10                  15

Arg Phe Gln Thr Thr Phe Leu Ser Thr Ser His His Gly Asn Gln Thr
            20                  25                  30

Lys Ala Ala His Arg His Ile His Val Gly Ser Thr Ala Gly Thr Thr
        35                  40                  45
```

```
Thr Ile Arg Ser Gly Gly Asp Thr Thr Leu Lys Gly Ala Gln Leu Ile
 50                  55                  60

Gly Lys Gly Ile Gln Ala Asp Thr Arg Asn Leu His Ile Glu Ser Val
 65                  70                  75                  80

Gln Asp Thr Glu Thr Ser Gln Ser Lys Gln Gln Asn Gly Asn Val Gln
                 85                  90                  95

Val Thr Val Gly Tyr Gly Phe Ser Ala Ser Gly Ser Tyr Ser Gln Ser
                100                 105                 110

Lys Val Lys Ala Asp His Ala Ser Val Thr Glu Gln Ser Gly Ile Tyr
                115                 120                 125

Ala Gly Glu Asp Gly Tyr Gln Ile Lys Val Gly Asn His Thr Asp Leu
            130                 135                 140

Lys Gly Ile Ile Thr Ser Gly Lys Ser Ala Glu Asp Lys Gly Lys
145                 150                 155                 160

Asn Leu Phe Gln Thr Ala Thr Leu Thr Ala Ser Asp Ile Gln Asn His
                165                 170                 175

Ser Arg Tyr Glu Gly Arg Ser Phe Gly Ile Gly Ser Phe Asp Leu
            180                 185                 190

Asn Gly Gly Trp Asp Gly Thr Val Thr Asp Lys Gln Gly Arg Pro Thr
            195                 200                 205

Asp Arg Ile Ser Leu Ala Ala Gly Tyr Gly Ser Asp Ser Asp Ser Gln
            210                 215                 220

Ser Ser Ile Thr Lys Ser Gly Ile Asn Thr Arg Asn Ile His Ile Thr
225                 230                 235                 240

Asp Glu Ala Gly Gln Leu Ala Arg Thr Gly Arg Thr Ala Lys Glu Thr
                245                 250                 255

Glu Ala Arg Ile Tyr Thr Gly Ile Asp Thr Glu Thr Ala Asp Gln His
                260                 265                 270

Thr Gly Arg Leu Lys Asn Ser Phe Asp Lys Asp Ala Val Ala Lys Glu
            275                 280                 285

Ile Asn Leu Gln Arg Glu Val Thr Lys Glu Phe Gly Arg Asn Ala Ala
            290                 295                 300

Gln Ala Val Ala Ala Val Ala Asp Lys Leu Gly Asn Thr Gln Ser Tyr
305                 310                 315                 320

Glu Arg Tyr Gln Glu Ala Arg Thr Leu Leu Glu Ala Glu Leu Gln Asn
                325                 330                 335

Thr Asp Ser Lys Ala Glu Lys Ala Ala Ile Arg Ala Ser Leu Gly Gln
                340                 345                 350

Val Asn Ala Tyr Leu Ala Glu Asn Gln Ser Arg Tyr Asp Thr Trp Lys
            355                 360                 365

Glu Gly Gly Ile Gly Arg Ser Ile Leu His Gly Ala Ala Gly Gly Leu
            370                 375                 380

Thr Thr Gly Ser Leu Gly Gly Ile Leu Ala Gly Ser Gly Thr Ser Leu
385                 390                 395                 400

Ala Ala Pro Tyr Leu Asp Lys Ala Ala Glu Asn Leu Gly Pro Ala Gly
                405                 410                 415

Lys Ala Ala Val Asn Ala Leu Gly Gly Ala Val Ile Gly Tyr Ala Ala
                420                 425                 430

Gly Gly Asn Val Gly Thr Ala Ala Val Gly Ala Asn Val Asp Trp Asn
            435                 440                 445

Asn Arg Gln Leu His Pro Lys Glu Thr Gln Ile Leu Asn Lys Leu Ser
            450                 455                 460

Lys Gly Lys Ser Ala Glu Glu Gln Tyr Arg Leu Lys Ala Ala Ala Cys
465                 470                 475                 480
```

| | | | | | | | | | | |
|---|---|---|---|---|---|---|---|---|---|---|
Ala Leu Thr Arg Cys Ala Glu Gly Val Pro Asp Phe Asp Pro Leu Tyr
            485                 490                 495

Lys Gly Leu Lys Asn Leu Gln Asp Ala Gly Lys Gln Phe Val Ala Glu
        500                 505                 510

Gln Asn Val Leu Met Arg Thr Asp Ala Phe Lys Tyr Gly Thr Trp Asn
        515                 520                 525

Ser Leu Asn Asp Ile Arg Ser Ser Tyr Asp Arg Ala Ala Thr Lys Ile
    530                 535                 540

Lys Gly Ala Gly Asn Met Gly Leu Gly Ala Thr Thr Phe Val Gly Ser
545                 550                 555                 560

Gly Ala Ile Gly Gly Leu Cys Ser Thr Gly Ile Gly Cys Ala Ala
                565                 570                 575

Gly Gly Leu Ile Ala Thr Ala Gly Met Thr Gly Tyr Thr Gln Ala
            580                 585                 590

Ser Glu Gly Ser Arg Gln Leu Phe Gly Thr Tyr Gln Ser Asp Phe Gly
        595                 600                 605

Lys Lys Val Val Leu Ser Leu Gly Thr Pro Ile Glu Tyr Glu Ser Pro
    610                 615                 620

Leu Val Ser Asp Ala Lys Asn Leu Ala Val Trp Gly Leu Glu Thr Leu
625                 630                 635                 640

Ile Thr Arg Lys Leu Gly Asn Leu Ala Thr Gly Val Lys Thr Ser Leu
                645                 650                 655

Thr Pro Lys Thr Ala Asp Val Gln Arg Asn Ile Leu Ser Gln Ser Glu
            660                 665                 670

Val Gly Ile Lys Trp Gly Lys Gly Ile Glu Gly Gln Gly Met Pro Trp
        675                 680                 685

Glu Asp Tyr Val Gly Lys Gly Leu Ser Ala Asn Ala Arg Leu Pro Lys
    690                 695                 700

Asn Phe Lys Thr Phe Asp Tyr Phe Asp Arg Gly Thr Gly Thr Ala Ile
705                 710                 715                 720

Ser Ala Lys Thr Leu Asp Thr Gln Thr Thr Ala Arg Leu Ser Lys Pro
                725                 730                 735

Glu Gln Leu Tyr Ser Thr Met Lys Gly Tyr Ile Asp Lys Thr Ala Asn
            740                 745                 750

Phe Lys Ser Tyr Glu Leu Ser Glu Val Pro Leu Arg Ala Asp Met Ile
        755                 760                 765

Lys Gln Arg Glu Ile His Leu Ala Ile Pro Ala Gln Thr Asn Lys Glu
    770                 775                 780

Gln Arg Leu Gln Leu Gln Arg Val Val Glu Tyr Gly Lys Ser Gln Asn
785                 790                 795                 800

Ile Thr Val Lys Ile Thr Glu Ile Glu
                805

```
<210> SEQ ID NO 75
<211> LENGTH: 2352
<212> TYPE: DNA
<213> ORGANISM: Neisseria meningitidis
<220> FEATURE:
<221> NAME/KEY: misc_feature
<222> LOCATION: 8, 9, 10, 11, 12
<223> OTHER INFORMATION: n = A,T,C or G

<400> SEQUENCE: 75
gtgtgtgnnn nngataaacg cagctataaa accggtaagt ggtacaaact aaaacatgtt      60
actgaaatca aagagcataa aaacgccaaa gccgacccgg tgagcctcag tgcgtcacaa     120
```

-continued

```
ggtattgaaa tcaaatccgg cggcaatatc ggtgcccacg ccaccttgtt tgatgcaccc      180
cgcggctccg ttaaaatcga agccggacgt gggctggttc tctatgccgt ggaagatctc      240
aactacgaca aacttgacac ccgtaccaag cgcaaattta tcggcattac ctacgacaag      300
gtgcacgaca ccaccaccca caccatgaaa accgccctgc cctcaagggt agttgcagaa      360
tcggccaacc tgcaatcagg ctgggacgcc aaactgcaag gcacccagtt tgaaaccacg      420
ctgggcggcg cagccatccg tgcaggtgta ggcgatcagg cacgagcaga tgccaagatt      480
attcttgaag gcatcaaaag tagtgtgcgc actgaaacag taagcagtag caaatctgcc      540
ctctggcaga aacaggccgg acgcggcagc aatatcgaaa ccttgcaact gccaagtttc      600
acaggctccg ttgcgcccgt actctctgcc cccggcggct atatcgttga tattccgaaa      660
ggcaatctga aaccgaaat cgaaaagctg ccaaacagc ccgaatacgc ctacctgaaa        720
cagcttcaga cggccaagaa cgtcgattgg aaacaggtgc agcttgtcta cgacaagtgg      780
gactataaag ccgaaggcct gaccggagcc ggagccgcca ttatcgcact ggccgttacc      840
gtggtcacct caggcgcagg aaccggagcc gtattgggat aaacggtgc ggccgccgcc        900
gcaaccgatg cagcattcgc ctctttggcc agccaggctt ccgtatcgtt catcaacaac      960
aaaggcaata tcggtaacac cctgaaagag ctgggcagaa gcagcacggt gaaaaatctg      1020
gtggttgccg ccgctaccgc aggcgtagcc gacaaaatcg cgcttcggc attgaacaat       1080
gtcagcgata agcagtggat caacaacctg accgtcaacc tggccaatgc gggcagtgcc      1140
gcactgatta ataccgctgt caacggcggc agcctgaaag acaatctgga agcgaatatc      1200
cttgcggctt tggtgaatac tgcgcatgga gaggcagcaa gtaaaatcaa acaattggat      1260
cagcactaca tagtccacaa gattgcccat gccatagcgg gctgtgcggc agcggcggcg      1320
aataagggca agtgtcagga tggcgcgata ggcgctgcag tcggtgagat tgttggtgag      1380
gctttggtta agaatactga tttcagtcgt atgagtgcga ccgaaatcga aaatctaaa       1440
gcgaagatta ctgcctattc aaaactggtt gccggcactg cgtctgccgt tgtaggcggg      1500
gatgtgaata cagcggcgaa tgcggcacag atagcggtgg agaataatac tttgtatcct      1560
agatgcgttg gtgcaaagtg tgatgaattt caaaaggaac aacaaaaatg gatacgtgaa      1620
aatcctgaag aatatcgaga agttttgctt cttcagacag gatttattcc aattatcggt      1680
gatatacaga gttttgtaca agcacagacc gctgccgatc acctgtttgc tttgctgggt      1740
gtggttccgg gtatcggtga atcgatacag gcctataaag tagcgaaagc ggcaaaaaat      1800
ttacaaggca tgaaaaaagc cttgacaag gcagcaaccg ttgccactgc acagggctat       1860
gtcagtaaaa ccaaaatcaa aatcggtcaa actgaattaa gggttactgc agcaactgac      1920
aaacaattgc tgaaagctat tggcgaagga agggacacga caggtaaaat gaccgagcag      1980
ttatttgact cttttagctaa acaaaatggc ttcagagtgc tttcgggcgg caaatacggc      2040
ggaaataacg gttttgatca tgtatggcag gctgccgatg gtagtgttgt tttgattgta      2100
gaaagtaagc agattaggaa cggtacggta cagctgaatc cgaatggtgc gggtggatat      2160
acgcagatga gtcgtgaatg gattaaacaa gttgtaaaaa gtttacctga tggtagtcct      2220
gctaaggcag ttgtcttaaa agcaaatcag aacggcaaat taaaaacggc aatagcaggc      2280
gttgatcgtc aaacaggtaa ggccgttatt ctttctgtca agttccttc taaaaccaat       2340
ataaggagat aa                                                          2352
```

<210> SEQ ID NO 76
<211> LENGTH: 783
<212> TYPE: PRT

<213> ORGANISM: Neisseria meningitidis
<220> FEATURE:
<221> NAME/KEY: VARIANT
<222> LOCATION: 3, 4
<223> OTHER INFORMATION: Xaa = Any Amino Acid

<400> SEQUENCE: 76

```
Met Cys Xaa Xaa Asp Lys Arg Ser Tyr Lys Thr Gly Lys Trp Tyr Lys
 1               5                  10                  15

Leu Lys His Val Thr Glu Ile Lys Glu His Lys Asn Ala Lys Ala Asp
            20                  25                  30

Pro Val Ser Leu Ser Ala Ser Gln Gly Ile Glu Ile Lys Ser Gly Gly
        35                  40                  45

Asn Ile Gly Ala His Ala Thr Leu Phe Asp Ala Pro Arg Gly Ser Val
    50                  55                  60

Lys Ile Glu Ala Gly Arg Gly Leu Val Leu Tyr Ala Val Glu Asp Leu
65                  70                  75                  80

Asn Tyr Asp Lys Leu Asp Thr Arg Thr Lys Arg Lys Phe Ile Gly Ile
                85                  90                  95

Thr Tyr Asp Lys Val His Asp Thr Thr Thr His Thr Met Lys Thr Ala
            100                 105                 110

Leu Pro Ser Arg Val Val Ala Glu Ser Ala Asn Leu Gln Ser Gly Trp
        115                 120                 125

Asp Ala Lys Leu Gln Gly Thr Gln Phe Glu Thr Thr Leu Gly Gly Ala
    130                 135                 140

Ala Ile Arg Ala Gly Val Gly Asp Gln Ala Arg Ala Asp Ala Lys Ile
145                 150                 155                 160

Ile Leu Glu Gly Ile Lys Ser Ser Val Arg Thr Glu Thr Val Ser Ser
                165                 170                 175

Ser Lys Ser Ala Leu Trp Gln Lys Gln Ala Gly Arg Gly Ser Asn Ile
            180                 185                 190

Glu Thr Leu Gln Leu Pro Ser Phe Thr Gly Ser Val Ala Pro Val Leu
        195                 200                 205

Ser Ala Pro Gly Gly Tyr Ile Val Asp Ile Pro Lys Gly Asn Leu Lys
    210                 215                 220

Thr Glu Ile Glu Lys Leu Ala Lys Gln Pro Glu Tyr Ala Tyr Leu Lys
225                 230                 235                 240

Gln Leu Gln Thr Ala Lys Asn Val Asp Trp Lys Gln Val Gln Leu Val
                245                 250                 255

Tyr Asp Lys Trp Asp Tyr Lys Ala Glu Gly Leu Thr Gly Ala Gly Ala
            260                 265                 270

Ala Ile Ile Ala Leu Ala Val Thr Val Val Thr Ser Gly Ala Gly Thr
        275                 280                 285

Gly Ala Val Leu Gly Leu Asn Gly Ala Ala Ala Ala Ala Thr Asp Ala
    290                 295                 300

Ala Phe Ala Ser Leu Ala Ser Gln Ala Ser Val Ser Phe Ile Asn Asn
305                 310                 315                 320

Lys Gly Asn Ile Gly Asn Thr Leu Lys Glu Leu Gly Arg Ser Ser Thr
                325                 330                 335

Val Lys Asn Leu Val Val Ala Ala Ala Thr Ala Gly Val Ala Asp Lys
            340                 345                 350

Ile Gly Ala Ser Ala Leu Asn Asn Val Ser Asp Lys Gln Trp Ile Asn
        355                 360                 365

Asn Leu Thr Val Asn Leu Ala Asn Ala Gly Ser Ala Ala Leu Ile Asn
    370                 375                 380
```

```
Thr Ala Val Asn Gly Gly Ser Leu Lys Asp Asn Leu Glu Ala Asn Ile
385                 390                 395                 400

Leu Ala Ala Leu Val Asn Thr Ala His Gly Glu Ala Ser Lys Ile
            405                 410                 415

Lys Gln Leu Asp Gln His Tyr Ile Val His Lys Ile Ala His Ala Ile
        420                 425                 430

Ala Gly Cys Ala Ala Ala Ala Asn Lys Gly Lys Cys Gln Asp Gly
        435                 440                 445

Ala Ile Gly Ala Ala Val Gly Glu Ile Val Gly Glu Ala Leu Val Lys
    450                 455                 460

Asn Thr Asp Phe Ser Arg Met Ser Ala Thr Glu Ile Glu Lys Ser Lys
465                 470                 475                 480

Ala Lys Ile Thr Ala Tyr Ser Lys Leu Val Ala Gly Thr Ala Ser Ala
            485                 490                 495

Val Val Gly Gly Asp Val Asn Thr Ala Ala Asn Ala Ala Gln Ile Ala
                500                 505                 510

Val Glu Asn Asn Thr Leu Tyr Pro Arg Cys Val Gly Ala Lys Cys Asp
            515                 520                 525

Glu Phe Gln Lys Glu Gln Gln Lys Trp Ile Arg Glu Asn Pro Glu Glu
530                 535                 540

Tyr Arg Glu Val Leu Leu Leu Gln Thr Gly Phe Ile Pro Ile Ile Gly
545                 550                 555                 560

Asp Ile Gln Ser Phe Val Gln Ala Gln Thr Ala Ala Asp His Leu Phe
                565                 570                 575

Ala Leu Leu Gly Val Val Pro Gly Ile Gly Glu Ser Ile Gln Ala Tyr
            580                 585                 590

Lys Val Ala Lys Ala Ala Lys Asn Leu Gln Gly Met Lys Lys Ala Leu
        595                 600                 605

Asp Lys Ala Ala Thr Val Ala Thr Ala Gln Gly Tyr Val Ser Lys Thr
    610                 615                 620

Lys Ile Lys Ile Gly Gln Thr Glu Leu Arg Val Thr Ala Ala Thr Asp
625                 630                 635                 640

Lys Gln Leu Leu Lys Ala Ile Gly Glu Gly Arg Asp Thr Thr Gly Lys
            645                 650                 655

Met Thr Glu Gln Leu Phe Asp Ser Leu Ala Lys Gln Asn Gly Phe Arg
        660                 665                 670

Val Leu Ser Gly Gly Lys Tyr Gly Gly Asn Asn Gly Phe Asp His Val
    675                 680                 685

Trp Gln Ala Ala Asp Gly Ser Val Val Leu Ile Val Glu Ser Lys Gln
690                 695                 700

Ile Arg Asn Gly Thr Val Gln Leu Asn Pro Asn Gly Ala Gly Gly Tyr
705                 710                 715                 720

Thr Gln Met Ser Arg Glu Trp Ile Lys Gln Val Val Lys Ser Leu Pro
            725                 730                 735

Asp Gly Ser Pro Ala Lys Ala Val Leu Lys Ala Asn Gln Asn Gly
        740                 745                 750

Lys Leu Lys Thr Ala Ile Ala Gly Val Asp Arg Gln Thr Gly Lys Ala
    755                 760                 765

Val Ile Leu Ser Val Lys Val Pro Ser Lys Thr Asn Ile Arg Arg
770                 775                 780

<210> SEQ ID NO 77
<211> LENGTH: 903
<212> TYPE: DNA
<213> ORGANISM: Neisseria meningitidis
```

-continued

```
<220> FEATURE:
<221> NAME/KEY: misc_feature
<222> LOCATION: 880, 881, 882, 883, 884
<223> OTHER INFORMATION: n = A,T,C or G

<400> SEQUENCE: 77
gtgagcatta gcgcgccgta tgccaatgaa acagccgca tcctgctgag caccacggat      60
atcagttcgg aaaacggcaa atcaaactg caatcctacg gcgaccagtt ctactacgcc     120
ggacagggtg agctctacac cttcgataaa cgcagctata aaaccggtaa gtggtacaaa    180
ctaaaacatg ttactgaaat caaagagcat aaaaacgcca agccgaccc ggtgagcctc     240 agtgcgtcac aaggtattga aatcaaatcc ggcggcaata tcggtgccca cgccaccttg    300
tttgatgcac cccgcggctc cgttaaaatc gaagccggac gtgggctggt tctctatgcc    360
gtggaagatc tcaactacga caaacttgac acccgtacca agcgcaaatt tatcggcatt    420
acctacgaca aggtgcacga caccaccacc cacaccatga aaccgccct gccctcaagg     480 gtagttgcag aatcggccaa cctgcaatca ggctgggacg ccaaactgca aggcacccag    540
tttgaaacca cgctgggcgg cgcagccatc cgtgcaggtg taggcgatca ggcacgagca    600
gatgccaaga ttattcttga aggcatcaaa agtagtgtgc gcactgaaac agtaagcagt    660
agcaaatctg ccctctggca gaaacaggcc ggacgcggca gcaatatcga aaccttgcaa    720
ctgccaagtt tcacaggctc cgttgcgccc gtactctctg ccccggcgg ctatatcgtt     780 gatattccga aaggcaatct gaaaaccgaa atcgaaaagc tggccaaaca gcccgaatac    840
gcctacctga acagcttca gacggccaag aacgtcgatn nnncacaca cttaattaat     900 taa                                                                  903

<210> SEQ ID NO 78
<211> LENGTH: 300
<212> TYPE: PRT
<213> ORGANISM: Neisseria meningitidis
<220> FEATURE:
<221> NAME/KEY: VARIANT
<222> LOCATION: 294, 295
<223> OTHER INFORMATION: Xaa = Any Amino Acid

<400> SEQUENCE: 78

Met Ser Ile Ser Ala Pro Tyr Ala Asn Glu Asn Ser Arg Ile Leu Leu
  1               5                  10                  15

Ser Thr Thr Asp Ile Ser Ser Glu Asn Gly Lys Ile Lys Leu Gln Ser
             20                  25                  30

Tyr Gly Asp Gln Phe Tyr Tyr Ala Gly Gln Gly Glu Tyr Leu Thr Phe
         35                  40                  45

Asp Lys Arg Ser Tyr Lys Thr Gly Lys Trp Tyr Lys Leu Lys His Val
     50                  55                  60

Thr Glu Ile Lys Glu His Lys Asn Ala Lys Ala Asp Pro Val Ser Leu
 65                  70                  75                  80

Ser Ala Ser Gln Gly Ile Glu Ile Lys Ser Gly Gly Asn Ile Gly Ala
                 85                  90                  95

His Ala Thr Leu Phe Asp Ala Pro Arg Gly Ser Val Lys Ile Glu Ala
            100                 105                 110

Gly Arg Gly Leu Val Leu Tyr Ala Val Glu Asp Leu Asn Tyr Asp Lys
        115                 120                 125

Leu Asp Thr Arg Thr Lys Arg Lys Phe Ile Gly Ile Thr Tyr Asp Lys
    130                 135                 140

Val His Asp Thr Thr His Thr Met Lys Thr Ala Leu Pro Ser Arg
145                 150                 155                 160
```

```
Val Val Ala Glu Ser Ala Asn Leu Gln Ser Gly Trp Asp Ala Lys Leu
            165                 170                 175

Gln Gly Thr Gln Phe Glu Thr Thr Leu Gly Gly Ala Ala Ile Arg Ala
            180                 185                 190

Gly Val Gly Asp Gln Ala Arg Ala Asp Ala Lys Ile Ile Leu Glu Gly
        195                 200                 205

Ile Lys Ser Ser Val Arg Thr Glu Thr Val Ser Ser Ser Lys Ser Ala
        210                 215                 220

Leu Trp Gln Lys Gln Ala Gly Arg Gly Ser Asn Ile Glu Thr Leu Gln
225                 230                 235                 240

Leu Pro Ser Phe Thr Gly Ser Val Ala Pro Val Leu Ser Ala Pro Gly
            245                 250                 255

Gly Tyr Ile Val Asp Ile Pro Lys Gly Asn Leu Lys Thr Glu Ile Glu
            260                 265                 270

Lys Leu Ala Lys Gln Pro Glu Tyr Ala Tyr Leu Lys Gln Leu Gln Thr
            275                 280                 285

Ala Lys Asn Val Asp Xaa Xaa Thr His Leu Ile Asn
            290                 295                 300
```